US011060102B2

(12) United States Patent
Gray et al.

(10) Patent No.: US 11,060,102 B2
(45) Date of Patent: Jul. 13, 2021

(54) INCREASING PLANT GROWTH AND YIELD BY USING A PSAN SEQUENCE

(71) Applicant: Benson Hill Biosystems, Inc., Research Triangle Park, NC (US)

(72) Inventors: Benjamin Neil Gray, Chapel Hill, NC (US); Henry D. Priest, Hazelwood, MO (US)

(73) Assignee: BENSON HILL, INC., St. Louis, MO (US)

( * ) Notice: Subject to any disclaimer, the term of this patent is extended or adjusted under 35 U.S.C. 154(b) by 0 days.

(21) Appl. No.: 16/311,389

(22) PCT Filed: Jun. 14, 2017

(86) PCT No.: PCT/IB2017/053547
§ 371 (c)(1),
(2) Date: Dec. 19, 2018

(87) PCT Pub. No.: WO2017/221115
PCT Pub. Date: Dec. 28, 2017

(65) Prior Publication Data
US 2019/0233839 A1    Aug. 1, 2019

Related U.S. Application Data

(60) Provisional application No. 62/353,866, filed on Jun. 23, 2016.

(51) Int. Cl.
*C12N 15/82* (2006.01)
*C07K 14/415* (2006.01)

(52) U.S. Cl.
CPC ........ *C12N 15/8261* (2013.01); *C07K 14/415* (2013.01); *C12N 15/8223* (2013.01); *C12N 15/8269* (2013.01); *Y02A 40/146* (2018.01)

(58) Field of Classification Search
None
See application file for complete search history.

(56) References Cited

U.S. PATENT DOCUMENTS

| | | | |
|---|---|---|---|
| 2002/0160378 A1* | 10/2002 | Harper | C07K 14/415 435/6.14 |
| 2006/0143729 A1* | 6/2006 | Alexandrov | C07K 14/415 800/278 |
| 2013/0167263 A1 | 6/2013 | Liu et al. | |

FOREIGN PATENT DOCUMENTS

| | | |
|---|---|---|
| DE | 199 40 270 A1 | 3/2001 |
| WO | WO 2010/034652 A1 | 4/2010 |
| WO | WO 2016/007640 A1 | 1/2016 |

OTHER PUBLICATIONS

Amunts et al, 2007, Nature, 447:58-63.*
Haldrup, A., et al., "The interaction between plastocyanin and photosystem I is inefficient in transgenic *Arabidopsis* plants lacking the PSI-N subunit of photosystem I," *The Plant Journal*, 1999, vol. 17(6), pp. 689-698.

* cited by examiner

*Primary Examiner* — Jason Deveau Rosen
(74) *Attorney, Agent, or Firm* — Womble Bond Dickinson (US) LLP

(57) ABSTRACT

Compositions and methods for improving plant growth are provided herein. Polynucleotides encoding photosystem I reaction center subunit N (PSAN) proteins, polypeptides encompassing PSAN proteins, and expression constructs for expressing genes of interest whose expression may improve agronomic properties including but not limited to crop yield, biotic and abiotic stress tolerance, and early vigor, plants comprising the polynucleotides, polypeptides, and expression constructs, and methods of producing transgenic plants are also provided.

6 Claims, No Drawings

Specification includes a Sequence Listing.

SEQUENCE LISTING

```
<160> NUMBER OF SEQ ID NOS: 100

<210> SEQ ID NO 1
<211> LENGTH: 372
<212> TYPE: DNA
<213> ORGANISM: Zea mays
<220> FEATURE:
<221> NAME/KEY: misc_feature
<222> LOCATION: (1)..(372)
<223> OTHER INFORMATION: PsaN

<400> SEQUENCE: 1
atggatccaa tcacacgccc ggcggcgcca tccttccata ggccagcggt cgccaccgcg      60
aaacacctcc accaggcggc cgccacactg gccaggcgca atggcgtgtc ccgccgctgc     120
ctgctcaccc tcctgatgag caccgcggcc atcccaggcg gcagcgaaag ccgcaaagcc     180
ctcctccaag aatacctgaa gaaatccaag gaaaataagg aaaagaacga taagaacgc      240 ctggacgact acaacaaacg caattacagg gattatttcg gcctcatcga ggggcaagtg     300
cgcgagaaga ccgaagaaga gaggaccgag agcgaaaaga ggattctgga atggctggac     360
aagaacaggt ga                                                         372

<210> SEQ ID NO 2
<211> LENGTH: 123
<212> TYPE: PRT
<213> ORGANISM: Zea mays
<220> FEATURE:
<221> NAME/KEY: MISC_FEATURE
<222> LOCATION: (1)..(123)
<223> OTHER INFORMATION: PsaN

<400> SEQUENCE: 2

Met Asp Pro Ile Thr Arg Pro Ala Ala Pro Ser Phe His Arg Pro Ala
1               5                   10                  15

Val Ala Thr Ala Lys His Leu His Gln Ala Ala Thr Leu Ala Arg
            20                  25                  30

Arg Asn Gly Val Ser Arg Arg Cys Leu Leu Thr Leu Leu Met Ser Thr
        35                  40                  45

Ala Ala Ile Pro Gly Gly Ser Glu Ser Arg Lys Ala Leu Leu Gln Glu
    50                  55                  60

Tyr Leu Lys Lys Ser Lys Glu Asn Lys Glu Lys Asn Asp Lys Glu Arg
65                  70                  75                  80

Leu Asp Asp Tyr Asn Lys Arg Asn Tyr Arg Asp Tyr Phe Gly Leu Ile
                85                  90                  95

Glu Gly Gln Val Arg Glu Lys Thr Glu Glu Glu Arg Thr Glu Ser Glu
            100                 105                 110

Lys Arg Ile Leu Glu Trp Leu Asp Lys Asn Arg
        115                 120
```

<210> SEQ ID NO 3
<211> LENGTH: 780
<212> TYPE: DNA
<213> ORGANISM: Cauliflower Mosaic Virus
<220> FEATURE:
<221> NAME/KEY: promoter
<222> LOCATION: (1)..(780)
<223> OTHER INFORMATION: 2X35S_Promoter

<400> SEQUENCE: 3

```
atggtggagc acgacactct cgtctactcc aagaatatca aagatacagt ctcagaagac    60
caaagggcta ttgagacttt tcaacaaagg gtaatatcgg gaaacctcct cggattccat   120
tgcccagcta tctgtcactt catcaaaagg acagtagaaa aggaaggtgg cacctacaaa   180
tgccatcatt gcgataaagg aaaggctatc gttcaagatg cctctgccga cagtggtccc   240
aaagatggac ccccacccac gaggagcatc gtggaaaaag aagacgttcc aaccacgtct   300
tcaaagcaag tggattgatg tgaacatggt ggagcacgac actctcgtct actccaagaa   360
tatcaaagat acagtctcag aagaccaaag ggctattgag acttttcaac aaagggtaat   420
atcgggaaac ctcctcggat tccattgccc agctatctgt cacttcatca aaaggacagt   480
agaaaaggaa ggtggcacct acaaatgcca tcattgcgat aaaggaaagg ctatcgttca   540
agatgcctct gccgacagtg gtcccaaaga tggaccccca cccacgagga gcatcgtgga   600
aaaagaagac gttccaacca cgtcttcaaa gcaagtggat tgatgtgata tctccactga   660
cgtaagggat gacgcacaat cccactatcc ttcgcaagac ccttcctcta tataaggaag   720
ttcatttcat ttggagagga cacgctgaaa tcaccagtct ctctctacaa atctatctct   780
```

<210> SEQ ID NO 4
<211> LENGTH: 209
<212> TYPE: DNA
<213> ORGANISM: Cauliflower Mosaic Virus
<220> FEATURE:
<221> NAME/KEY: misc_feature
<222> LOCATION: (1)..(209)
<223> OTHER INFORMATION: 35S_PolyA

<400> SEQUENCE: 4

```
gatctgtcga tcgacaagct cgagtttctc cataataatg tgtgagtagt tcccagataa    60
gggaattagg gttcctatag ggtttcgctc atgtgttgag catataagaa acccttagta   120
tgtatttgta tttgtaaaat acttctatca ataaaatttc taattcctaa aaccaaaatc   180
cagtactaaa atccagatcc cccgaatta                                      209
```

<210> SEQ ID NO 5
<211> LENGTH: 741
<212> TYPE: DNA
<213> ORGANISM: Sorghum bicolor
<220> FEATURE:
<221> NAME/KEY: promoter
<222> LOCATION: (1)..(741)
<223> OTHER INFORMATION: 4xRGCGR_Promoter
<220> FEATURE:
<221> NAME/KEY: misc_feature
<222> LOCATION: (1)..(252)
<223> OTHER INFORMATION: 4xRGCGR_Repeats
<220> FEATURE:
<221> NAME/KEY: 5'UTR
<222> LOCATION: (253)..(741)
<223> OTHER INFORMATION: SbCA_5'UTR

<400> SEQUENCE: 5

```
gaagcgagtg gcgcgctggc ggatgaggcg gcgagtggcc cggatgcacc ggcgcaggcg    60
```

```
agcgaagcga gtggcgcgct ggcggatgag gcggcgagtg gcccggatgc accggcgcag      120
gcgagcgaag cgagtggcgc gctggcggat gaggcggcga gtggcccgga tgcaccggcg      180
caggcgagcg aagcgagtgg cgcgctggcg gatgaggcgg cgagtggccc ggatgcaccg      240
gcgcaggcga gccgcacgcc gccgcccgcc gcggcgctcg cgcgcgcacc gctgccgcct      300
gccgccacac aatgcgagcg cgcgcgcaca cacacacaca ccacccgggc gggggggctg      360
tagtagtaac ggccttgtct tgtcggcacg cgcgcgtccg tgtgtataag gaggcaggcc      420
cgcgacaacg ataagcggca ctcgcacgat caatgtacac attgcccgtc cgcgccacca      480
catccagcat cgtcgccagc ctcgccaccc ccgcgccgtc ctcctcctcc ggctccggct      540
ccggccgccc caggcccagg ctcatccgga acgcccccgt cttcgccgcc ccgccaccg      600 tcgtgtaaac gggacggcgg gcagctgagg agtcaaacga gagagatcga gagaaagaaa      660
gggagggcat ccaccagccg ccggcgataa gaggggagga gagagaggcc agagaagagg      720
aggagaagaa gaagaaatcg a                                                741

<210> SEQ ID NO 6
<211> LENGTH: 287
<212> TYPE: DNA
<213> ORGANISM: Zea mays
<220> FEATURE:
<221> NAME/KEY: 3'UTR
<222> LOCATION: (1)..(287)
<223> OTHER INFORMATION: CA_3'UTR

<400> SEQUENCE: 6
gttcaaaact agggctacgg caattctacc ggcccgccga ctcctgcatc atcataaata       60
tatatactat actatactac tacgtaccta ccgatatgca cccgagcaat gtgaatgcgt      120
cgagtactat atatctgttt tctgcatcta catatatata ccggatcaat cgcccaatgt      180
gaatgtaata agcaatatca ttttctacca cttttcattc ctaacgctga gcttttatg      240 tactatatct tatatgatga ataataatat gaccgccttg tgatcta                   287

<210> SEQ ID NO 7
<211> LENGTH: 121
<212> TYPE: PRT
<213> ORGANISM: Sorghum bicolor
<220> FEATURE:
<221> NAME/KEY: MISC_FEATURE
<222> LOCATION: (1)..(121)
<223> OTHER INFORMATION: PsaN

<400> SEQUENCE: 7

Met Asp Pro Ile Thr Arg Pro Val Ala Ser Ser Phe His Arg Ser
1               5                   10                  15

Ala Ala Lys His Leu His Arg Ala Val Thr Ser Ala Gln Arg Asn Gly
            20                  25                  30

Val Ser Arg Arg Cys Leu Leu Thr Leu Leu Thr Ser Thr Ala Ala Ile
        35                  40                  45

Pro Pro Gly Gly Ser Glu Ser Arg Lys Ala Leu Leu Gln Glu Tyr Leu
    50                  55                  60

Lys Lys Ser Glu Glu Asn Lys Glu Lys Asn Asp Lys Glu Arg Leu Asp
65                  70                  75                  80

Asp Tyr Tyr Lys Arg Asn Tyr Lys Asp Tyr Phe Gly Leu Ile Glu Gly
                85                  90                  95

Pro Ala Arg Glu Lys Lys Glu Glu Glu Arg Thr Glu Ser Glu Lys Arg
            100                 105                 110
```

Ile Leu Glu Trp Leu Asp Lys Asn Lys
        115                 120

<210> SEQ ID NO 8
<211> LENGTH: 129
<212> TYPE: PRT
<213> ORGANISM: Oryza brachyantha
<220> FEATURE:
<221> NAME/KEY: MISC_FEATURE
<222> LOCATION: (1)..(129)
<223> OTHER INFORMATION: PsaN

<400> SEQUENCE: 8

Met Ala Gln Pro Ser Gly Lys Pro Val Asp Thr Val Arg Arg Pro Cys
1               5                   10                  15

Thr Ala Ala Ser Ala Ser Arg Arg Ser Ala Ala Lys Asn Leu Gln Pro
            20                  25                  30

Leu Ala Thr Leu Pro Arg Lys Asn Gly Ile Thr Arg Arg Gly Leu Leu
        35                  40                  45

Thr Leu Leu Ala Ser Thr Ala Ala Ile Pro Glu Ala Ser Glu Ser Arg
    50                  55                  60

Lys Ala Leu Leu Gln Glu Tyr Leu Asn Lys Ser Lys Glu Asn Lys Glu
65                  70                  75                  80

Lys Asn Asp Lys Glu Arg Leu Asp Asp Tyr Tyr Lys Arg Asn Tyr Lys
                85                  90                  95

Asp Tyr Phe Gly Leu Ile Glu Gly Pro Ala Arg Gln Lys Thr Glu Glu
            100                 105                 110

Glu Leu Thr Glu Ser Glu Lys Arg Ile Leu Glu Trp Leu Asp Lys Asn
        115                 120                 125

Lys

<210> SEQ ID NO 9
<211> LENGTH: 129
<212> TYPE: PRT
<213> ORGANISM: Oryza sativa
<220> FEATURE:
<221> NAME/KEY: MISC_FEATURE
<222> LOCATION: (1)..(129)
<223> OTHER INFORMATION: PsaN

<400> SEQUENCE: 9

Met Ala Gln Pro Gln Gly Lys Leu Val Asp Thr Ile Arg Arg Pro Phe
1               5                   10                  15

Thr Ala Ala Ser Thr Phe His Arg Ser Ala Thr Arg His Leu Gln Pro
            20                  25                  30

Leu Ala Met Leu Ala Gln Arg Asn Gly Ile Ser Arg Arg Gly Leu Leu
        35                  40                  45

Thr Phe Leu Thr Ser Thr Ala Ala Ile Pro Glu Ala Gly Glu Ser Arg
    50                  55                  60

Lys Ala Leu Leu Gln Glu Tyr Leu Lys Lys Ser Lys Glu Asn Lys Glu
65                  70                  75                  80

Lys Asn Asp Lys Glu Arg Leu Asp Asp Tyr Tyr Lys Arg Asn Tyr Arg
                85                  90                  95

Asp Tyr Phe Gly Leu Ile Glu Gly Pro Ala Arg Gln Lys Asn Glu Asp
            100                 105                 110

Glu Leu Thr Glu Ser Glu Lys Gly Ile Leu Glu Trp Leu Asp Lys Asn
        115                 120                 125

Lys

<210> SEQ ID NO 10
<211> LENGTH: 331
<212> TYPE: PRT
<213> ORGANISM: Aegilops tauschii
<220> FEATURE:
<221> NAME/KEY: MISC_FEATURE
<222> LOCATION: (1)..(331)
<223> OTHER INFORMATION: PsaN

<400> SEQUENCE: 10

Met Ala Gln Pro Gln Gly Lys Leu Met Asp Thr Ile Arg Arg Pro Val
1               5                   10                  15

Ala Ala Ala Ser Ser Leu His His Ser Ala Ala Lys His Leu Val Thr
            20                  25                  30

Leu Ala Gln Arg Asn Gly Val Asn Arg Arg Cys Leu Leu Thr Leu Leu
        35                  40                  45

Val Ser Ala Ala Ala Ile Pro Glu Ala Gly Glu Ser Arg Lys Ala Leu
    50                  55                  60

Leu Gln Asp Tyr Val Lys Arg Ser Lys Glu Asn Lys Glu Lys Asn Asp
65                  70                  75                  80

Lys Glu Arg Arg Asp Ala Val Tyr Lys Arg Asn Tyr Lys Asp Tyr Phe
                85                  90                  95

Gly Phe Met Glu Gly Pro Val Arg Glu Lys Pro Ala Glu Glu Leu Thr
            100                 105                 110

Glu Ser Glu Lys Gly Ile Leu Ala Trp Leu Asp Lys Asn Lys Ile Ser
        115                 120                 125

Ser Tyr His Ile Ile Ser Ser Ser Asn Leu Pro Cys Arg Lys Ser
    130                 135                 140

Arg Glu His Thr Gly Glu Gln Thr His Leu Ile Pro Trp Leu Ser Leu
145                 150                 155                 160

Gln Arg Asn Gly Val Asn Arg Arg Cys Leu Leu Thr Leu Leu Ala Ser
                165                 170                 175

Ala Ala Ala Ile Pro Glu Ala Ser Glu Ser Arg Lys Ala Leu Leu Gln
            180                 185                 190

Asp Tyr Val Lys Arg Ser Lys Glu Asn Lys Glu Lys Asn Asp Lys Glu
        195                 200                 205

Arg Leu Asp Asp Phe Tyr Lys Arg Asn Tyr Lys Asp Tyr Phe Gly Phe
    210                 215                 220

Met Glu Gly Ser Lys Asn Met Ala Pro Ser Pro Arg Thr Ala Gly Ser
225                 230                 235                 240

Gly Met Ile Leu Arg Arg Asn Asp Gly Ser Val Ile Phe Ala Ala Tyr
                245                 250                 255

Arg His Leu Phe Phe Cys Asp Asn Ala Leu Glu Ala Glu Leu His Ala
            260                 265                 270

Ile Ser Gly Asp Ser Ile Gly Phe Leu Asn Ser Leu Asp Leu Leu Ala
        275                 280                 285

Tyr Gly His Leu Ile Leu Glu Ile Arg Val Leu Trp Ser Val Leu Gly
    290                 295                 300

Arg Glu Phe Val Pro Met Lys Ile Tyr Arg Asp Gln Asn Arg Val Ala
305                 310                 315                 320

Asp His Gly Arg Thr Val Tyr Asn Arg Ala Cys
                325                 330

<210> SEQ ID NO 11
<211> LENGTH: 129

<212> TYPE: PRT
<213> ORGANISM: Setaria italica
<220> FEATURE:
<221> NAME/KEY: MISC_FEATURE
<222> LOCATION: (1)..(129)
<223> OTHER INFORMATION: PsaN

<400> SEQUENCE: 11

Met Ala Trp Pro Gln Gly Lys Leu Met Asp Pro Ile Arg Ser Pro Ile
1               5                   10                  15

Ala Ala Thr Ser Ser Phe His Gln Ser Ala Val Lys His Leu Gln Gln
            20                  25                  30

Gly Val Ile Leu Ala His Arg Asn Gly Ile Ser Arg Arg Cys Leu Leu
        35                  40                  45

Thr Leu Leu Thr Ser Thr Ala Ala Ile Pro Asp Ser Ser Glu Ser Arg
    50                  55                  60

Lys Ala Leu Leu Gln Glu Tyr Leu Lys Lys Ser Lys Glu Asn Lys Glu
65                  70                  75                  80

Lys Asn Asp Lys Glu Arg Leu Asp Asp Tyr Tyr Lys Arg Asn Tyr Lys
                85                  90                  95

Asp Tyr Phe Gly Leu Ile Glu Gly Pro Ala Arg Glu Lys Lys Glu Glu
            100                 105                 110

Glu Arg Thr Glu Ser Glu Lys Arg Ile Leu Glu Trp Leu Asp Lys Asn
        115                 120                 125

Lys

<210> SEQ ID NO 12
<211> LENGTH: 129
<212> TYPE: PRT
<213> ORGANISM: Brachypodium distachyon
<220> FEATURE:
<221> NAME/KEY: MISC_FEATURE
<222> LOCATION: (1)..(129)
<223> OTHER INFORMATION: PsaN

<400> SEQUENCE: 12

Met Ala His Pro Leu Gly Lys Pro Met Asp Thr Ile Arg Arg Pro Val
1               5                   10                  15

Thr Ala Ala Ser Ser Phe His Gln Ser Ala Thr Lys His Leu Gln Pro
            20                  25                  30

Leu Val Thr Leu Ala Gln Arg Asn Gly Val Ser Arg Arg Cys Leu Leu
        35                  40                  45

Thr Leu Leu Ala Ser Ala Ala Ala Ile Pro Glu Ala Ser Glu Ser Arg
    50                  55                  60

Lys Ala Leu Leu Gln Glu Tyr Val Lys Lys Ser Lys Glu Asn Lys Glu
65                  70                  75                  80

Lys Asn Asp Lys Glu Arg Met Asp Asp Asn Tyr Lys Arg Asn Tyr Lys
                85                  90                  95

Asp Tyr Phe Gly Phe Met Glu Gly Pro Val Arg Glu Lys Lys Ala Glu
            100                 105                 110

Asp Leu Thr Glu Ser Glu Lys Gly Ile Leu Ala Trp Leu Asp Arg Asn
        115                 120                 125

Lys

<210> SEQ ID NO 13
<211> LENGTH: 126
<212> TYPE: PRT
<213> ORGANISM: Musa acuminata
<220> FEATURE:

```
<221> NAME/KEY: MISC_FEATURE
<222> LOCATION: (1)..(126)
<223> OTHER INFORMATION: PsaN

<400> SEQUENCE: 13
```

Met Ala Leu Lys Ile Gly Ala Leu Ser Thr Met Asn Arg Gln Phe Pro
1               5                   10                  15

Ser Ser Ala Ala Ala Ser Leu Val Leu Pro Arg Pro Val Thr Lys Ser
            20                  25                  30

Ala Tyr Arg Asn Asp Ile Gly Arg Arg Gly Leu Leu Thr Leu Leu Ile
        35                  40                  45

Ser Thr Ala Thr Val Pro Glu Val Thr Asp Pro Lys Lys Ala Leu Leu
50                  55                  60

Gln Glu Tyr Leu Lys Arg Ser Lys Glu Asn Lys Ala Lys Asn Asp Lys
65                  70                  75                  80

Glu Arg Leu Asp Asp Tyr Tyr Lys Arg Asn Tyr Lys Asp Tyr Phe Glu
                85                  90                  95

Phe Ile Glu Gly Ser Leu Lys Asp Lys Asn Glu Glu Leu Leu Ser Glu
            100                 105                 110

Ser Glu Lys Asp Ile Ile Lys Trp Leu Gln Lys Asn Arg Lys
        115                 120                 125

```
<210> SEQ ID NO 14
<211> LENGTH: 125
<212> TYPE: PRT
<213> ORGANISM: Elaeis guineensis
<220> FEATURE:
<221> NAME/KEY: MISC_FEATURE
<222> LOCATION: (1)..(125)
<223> OTHER INFORMATION: PsaN

<400> SEQUENCE: 14
```

Met Ala Leu Pro Arg Gly Thr Leu Pro Pro Lys Asn Arg Pro Ala Ala
1               5                   10                  15

Ser Pro Glu Arg Val Ile His Ser Leu Arg His Leu Val Lys Leu Val
            20                  25                  30

Gln Val Lys Glu Val Arg Arg Arg Ser Leu Leu Pro Leu Leu Val Ser
        35                  40                  45

Thr Ala Thr Leu Pro Gln Gly Asn Asp Ser Lys Asn Ala Leu Leu Gln
50                  55                  60

Glu Tyr Leu Lys Arg Ser Lys Glu Asn Lys Ala Arg Asn Asp Lys Glu
65                  70                  75                  80

Arg Leu Asp Asp Tyr Tyr Lys Arg Asn Tyr Lys Asp Tyr Phe Glu Phe
                85                  90                  95

Phe Glu Gly Ser Ala Arg Glu Lys Lys Glu Glu Leu Leu Ser Glu Ser
            100                 105                 110

Glu Arg Ala Ile Arg Ala Trp Leu Glu Lys Asn Lys Lys
        115                 120                 125

```
<210> SEQ ID NO 15
<211> LENGTH: 129
<212> TYPE: PRT
<213> ORGANISM: Brachypodium distachyon
<220> FEATURE:
<221> NAME/KEY: MISC_FEATURE
<222> LOCATION: (1)..(129)
<223> OTHER INFORMATION: PsaN

<400> SEQUENCE: 15
```

Met Ala Gln Pro Pro Gly Lys Leu Met Asp Thr Ile Arg Ser Pro Val

-continued

```
                1               5                      10                    15
            Thr Ala Ser Leu Leu His Gln Ser Ala Ala Lys His Leu Gln Pro
                            20                  25                  30
            Leu Val Thr Leu Ala Gln Arg Asn Gly Thr Gly Arg Arg Tyr Leu Leu
                            35                  40                  45
            Thr Leu Leu Ala Ser Ala Ala Ile Pro Glu Ala Gly Glu Ser Arg
             50                  55                  60
            Lys Ala Leu Leu Gln Asp Tyr Val Lys Ser Lys Glu Asn Lys Glu
             65                  70                  75                  80
            Lys Asn Asp Lys Glu Arg Leu Asp Asp Tyr Tyr Lys Arg Asn Tyr Gln
                            85                  90                  95
            Asp Tyr Phe Gly Phe Met Glu Gly Ser Val Arg Glu Lys Lys Glu Glu
                            100                 105                 110
            Glu Leu Thr Glu Ser Gly Lys Gly Ile Leu Ala Trp Leu Asp Lys Asn
                            115                 120                 125
            Lys
```

```
<210> SEQ ID NO 16
<211> LENGTH: 124
<212> TYPE: PRT
<213> ORGANISM: Phoenix dactylifera
<220> FEATURE:
<221> NAME/KEY: MISC_FEATURE
<222> LOCATION: (1)..(124)
<223> OTHER INFORMATION: PsaN

<400> SEQUENCE: 16
```

```
            Met Ala Leu Pro Trp Gly Thr Leu Pro Leu Lys Asn Lys Pro Ala Ala
             1               5                  10                  15
            Ser Ser Glu Gly Glu Ile His Cys Leu Arg Thr Phe Val Lys Leu Val
                            20                  25                  30
            Gln Val Lys Val Val Arg Arg Ser Leu Leu Pro Leu Leu Val Ser Thr
                            35                  40                  45
            Ala Thr Leu Pro Gln Gly Asn Asp Ser Lys Lys Asp Leu Leu Gln Glu
             50                  55                  60
            Tyr Leu Lys Arg Ser Lys Glu Asn Lys Ala Arg Asn Asp Lys Glu Arg
             65                  70                  75                  80
            Leu Asp Asp Tyr Tyr Lys Arg Asn Tyr Lys Asp Tyr Phe Glu Leu Ile
                            85                  90                  95
            Glu Gly Ser Ala Arg Asp Lys Lys Glu Glu Leu Leu Ser Glu Ser Glu
                            100                 105                 110
            Arg Gly Ile Arg Ala Trp Leu Glu Lys Asn Lys Lys
                            115                 120
```

```
<210> SEQ ID NO 17
<211> LENGTH: 121
<212> TYPE: PRT
<213> ORGANISM: Capsicum annuum
<220> FEATURE:
<221> NAME/KEY: MISC_FEATURE
<222> LOCATION: (1)..(121)
<223> OTHER INFORMATION: PsaN

<400> SEQUENCE: 17
```

```
            Met Ala Leu Thr Ile Gly Asn Cys Thr Asn Ser Phe Ser Arg Phe Tyr
             1               5                  10                  15
            Val Gln Ala Ile Asp Asn Thr Lys Glu Ile Lys Val Thr Thr Lys Lys
                            20                  25                  30
```

-continued

```
Glu Thr Arg Gln Gly Arg Arg Gly Leu Leu Phe Ser Thr Ile Val Ala
         35                  40                  45

Ile Val Gln Val Asn Asp Ser Gln Asn Glu Leu Leu Lys Arg Tyr Leu
 50                  55                  60

Lys Lys Ser Glu Glu Asn Lys Ala Lys Asn Asp Lys Glu Arg Leu Asp
 65                  70                  75                  80

Asn Tyr Tyr Lys Arg Asn Tyr Arg Asp Tyr Phe Gly Tyr Leu Glu Gly
                 85                  90                  95

Thr Leu Lys Gln Lys Gln Glu Glu Leu Thr Glu Ser Glu Lys Gly
            100                 105                 110

Ile Leu Asn Trp Leu Glu Lys Asn Lys
            115                 120

<210> SEQ ID NO 18
<211> LENGTH: 436
<212> TYPE: PRT
<213> ORGANISM: Triticum urartu
<220> FEATURE:
<221> NAME/KEY: MISC_FEATURE
<222> LOCATION: (1)..(436)
<223> OTHER INFORMATION: PsaN
<220> FEATURE:
<221> NAME/KEY: MISC_FEATURE
<222> LOCATION: (219)..(336)
<223> OTHER INFORMATION: PsaN

<400> SEQUENCE: 18

Met Phe Leu Thr Arg Gly Pro Leu Pro Leu Ala Pro Leu Trp Glu Arg
 1               5                  10                  15

Phe Phe Arg Gly His Glu Gly Arg Tyr Ser Val Tyr Val His Ala Leu
                 20                  25                  30

Pro Ser Tyr Arg Ala Asn Phe Thr Lys Asp Ser Val Phe Tyr His Arg
             35                  40                  45

Gln Ile Pro Ser Lys Val Ala Glu Trp Gly Gln Met Thr Met Cys Asp
 50                  55                  60

Ala Glu Arg Arg Leu Leu Ala Asn Ala Leu Leu Asp Ile Ser Asn Glu
 65                  70                  75                  80

Trp Phe Val Leu Val Ser Glu Ser Cys Ile Pro Ile Phe Asp Phe Asn
                 85                  90                  95

Thr Thr Tyr Asp Tyr Phe Gln Asn Ser Ser Gln Ser Phe Val Met Val
            100                 105                 110

Phe Asp Asp Pro Gly Pro Tyr Gly Arg Gly Arg Tyr Asn Tyr Asn Met
            115                 120                 125

Thr Pro Glu Val Glu Ile Glu Gln Trp Arg Lys Gly Ser Gln Trp Phe
130                 135                 140

Glu Val Asp Arg Asp Leu Ala Ile Glu Ile Arg Asp Thr Arg Tyr
145                 150                 155                 160

Tyr Pro Lys Phe Lys Glu Phe Cys Arg Pro His Cys Ala Pro Leu Met
                165                 170                 175

Tyr Tyr Gln Thr Leu Cys Trp Lys Asn Val Glu Ile Lys Ala Arg Lys
            180                 185                 190

Ile Ile Gln Thr Cys Gly Pro Lys Ile Lys Ile Lys Cys Arg Tyr Gln
        195                 200                 205

Glu Ser Lys Asn Val Asn Gly Ser Lys Leu Met Asp Thr Ile Arg Arg
    210                 215                 220

Pro Val Ala Ala Ala Ser Ser Leu His His Ser Ala Ala Lys His Leu
225                 230                 235                 240
```

```
Ala Ile Leu Ala His Arg Asn Gly Val Asn Arg Tyr Leu Leu Thr
                245                 250                 255

Leu Leu Ala Ser Ala Ala Ile Pro Glu Ala Gly Glu Ser Arg Lys
            260                 265                 270

Ala Leu Leu Gln Asp Tyr Val Lys Ser Lys Glu Asn Lys Glu Lys
            275                 280                 285

Asn Asp Lys Glu Arg Arg Asp Ala Val Tyr Lys Arg Asn Tyr Lys Asp
    290                 295                 300

Tyr Phe Gly Phe Met Glu Gly Pro Val Arg Glu Lys Pro Ala Glu Glu
305                 310                 315                 320

Leu Thr Glu Ser Glu Lys Gly Ile Leu Ala Trp Leu Asp Lys Asn Lys
            325                 330                 335

Gly Met Glu Leu Thr Glu Gly Ala Ser Ser Leu Tyr Trp His Pro Pro
            340                 345                 350

Gln Pro Tyr Pro Arg Leu Ala Asn Leu Glu Arg Arg Tyr Cys Lys Ile
            355                 360                 365

Thr Gly Ser Ala Cys Ile Trp Val Asp Tyr Val Lys Arg Ser Lys Glu
            370                 375                 380

Asn Lys Glu Lys Asn Asp Lys Glu Arg Leu Asp Asp Phe Tyr Lys Arg
385                 390                 395                 400

Asn Tyr Lys Asp Tyr Phe Gly Phe Met Glu Gly Ser Val Arg Glu Lys
                405                 410                 415

Pro Val Glu Glu Leu Thr Glu Ser Glu Lys Gly Ile Leu Ala Trp Leu
            420                 425                 430

Asp Lys Asn Lys
        435

<210> SEQ ID NO 19
<211> LENGTH: 147
<212> TYPE: PRT
<213> ORGANISM: Theobroma cacao
<220> FEATURE:
<221> NAME/KEY: MISC_FEATURE
<222> LOCATION: (1)..(147)
<223> OTHER INFORMATION: PsaN

<400> SEQUENCE: 19

Met Ser Ser Met Ala Gln Ser Val Leu Met Ala Leu Thr Val Thr Val
1               5                   10                  15

Asn Gln Phe Ala Ser Ser Asn Val His Ala Val His Arg Lys Gln Gly
            20                  25                  30

Lys Ser Pro Pro Thr Thr Ser Lys Pro Lys Pro Ser Thr Thr Thr
        35                  40                  45

Pro Ile Thr Ala Gly Ala Ala Thr Ser Asp Thr Ile Gly Ile Gly Arg
    50                  55                  60

Arg Gly Leu Ile Leu Ser Ala Val Ala Ala Pro Gln Leu Asn Asp
65              70                  75                  80

Ser Arg Thr Glu Leu Leu Lys Lys Tyr Leu Lys Ser Glu Glu Asn
            85                  90                  95

Lys Ala Lys Asn Asp Lys Glu Arg Gln Asp Asn Tyr Tyr Lys Arg Asn
            100                 105                 110

Tyr Lys Asp Tyr Phe Glu Phe Val Glu Gly Thr Leu Lys Gly Lys Ser
            115                 120                 125

Glu Glu Gln Leu Thr Glu Ser Glu Lys Gly Ile Leu Asp Trp Leu Lys
    130                 135                 140

Ala Asn Lys
```

<210> SEQ ID NO 20
<211> LENGTH: 129
<212> TYPE: PRT
<213> ORGANISM: Capsella rubella
<220> FEATURE:
<221> NAME/KEY: MISC_FEATURE
<222> LOCATION: (1)..(129)
<223> OTHER INFORMATION: PsaN

<400> SEQUENCE: 20

Met Ser Ser Ile Gly Gln Ser Ile Leu Met Ala Leu Thr Val Thr Val
1               5                   10                  15

Asn Lys Tyr Ala Ser Ser Val Gln Ser Val Arg Arg Asn Glu Ser
            20                  25                  30

Lys Arg Asp Ser Leu Thr Thr Gln Thr Ala Asp Leu Gly Arg Arg Asn
        35                  40                  45

Val Ile Phe Ser Ser Thr Ser Phe Ile Ala Ala Leu Thr Thr Ser
    50                  55                  60

Asp Gln Leu Leu Gln Lys Tyr Leu Lys Lys Ser Glu Glu Asn Lys Ser
65                  70                  75                  80

Lys Asn Asp Lys Glu Arg Leu Asp Ser Tyr Tyr Lys Arg Asn Tyr Arg
                85                  90                  95

Asp Tyr Phe Glu Phe Val Glu Gly Ser Thr Lys Gly Lys Thr Glu Ala
            100                 105                 110

Glu Leu Ser Glu Ser Glu Lys Gln Ile Leu Glu Trp Leu Lys Ala Asn
        115                 120                 125

Lys

<210> SEQ ID NO 21
<211> LENGTH: 129
<212> TYPE: PRT
<213> ORGANISM: Arabidopsis thaliana
<220> FEATURE:
<221> NAME/KEY: MISC_FEATURE
<222> LOCATION: (1)..(129)
<223> OTHER INFORMATION: PsaN

<400> SEQUENCE: 21

Met Ser Ser Ile Ser Gln Ser Ile Leu Met Ala Leu Thr Val Thr Val
1               5                   10                  15

Asn Lys Tyr Ala Ser Ser Asn Val Gln Ala Val Arg Arg Asn Asp Thr
            20                  25                  30

Lys Arg His Ser Leu Thr Ala Pro Pro Ala Asp Leu Gly Arg Arg Asn
        35                  40                  45

Ile Leu Phe Ser Ser Thr Ser Phe Ile Ala Ala Ala Leu Thr Ser Ser
    50                  55                  60

Asp Gln Leu Leu Gln Lys Tyr Leu Lys Lys Thr Glu Glu Asn Lys Ala
65                  70                  75                  80

Lys Asn Asp Lys Glu Arg Leu Asp Ser Phe Tyr Lys Arg Asn Tyr Lys
                85                  90                  95

Asp Tyr Phe Glu Phe Val Glu Gly Ser Ile Lys Gly Lys Thr Glu Ala
            100                 105                 110

Glu Leu Ser Glu Ser Glu Lys Arg Ile Leu Glu Trp Leu Lys Ala Asn
        115                 120                 125

Lys

-continued

```
<210> SEQ ID NO 22
<211> LENGTH: 129
<212> TYPE: PRT
<213> ORGANISM: Arabidopsis lyrata
<220> FEATURE:
<221> NAME/KEY: MISC_FEATURE
<222> LOCATION: (1)..(129)
<223> OTHER INFORMATION: PsaN

<400> SEQUENCE: 22
```

Met Ser Ser Ile Ser Gln Ser Ile Leu Met Ala Leu Thr Val Thr Val
1               5                   10                  15

Asn Lys Tyr Ala Ser Ser Asn Val Gln Ala Val Arg Arg Asn Asp Thr
            20                  25                  30

Lys Arg Asp Ser Leu Thr Ala Pro Val Ala Asp Leu Gly Arg Arg Asn
        35                  40                  45

Ile Leu Phe Ser Ser Thr Ser Phe Ile Ala Thr Ala Leu Thr Ser Ser
    50                  55                  60

Asp Gln Leu Leu Gln Lys Tyr Leu Lys Thr Glu Glu Asn Lys Ala
65                  70                  75                  80

Lys Asn Asp Lys Glu Arg Leu Asp Ser Phe Tyr Lys Arg Asn Tyr Lys
                85                  90                  95

Asp Tyr Phe Glu Phe Val Glu Gly Ser Ile Lys Gly Lys Thr Glu Ala
            100                 105                 110

Glu Leu Ser Glu Ser Gly Lys Arg Ile Leu Glu Trp Leu Lys Ala Asn
        115                 120                 125

Lys

```
<210> SEQ ID NO 23
<211> LENGTH: 126
<212> TYPE: PRT
<213> ORGANISM: Spinacia oleracea
<220> FEATURE:
<221> NAME/KEY: MISC_FEATURE
<222> LOCATION: (1)..(126)
<223> OTHER INFORMATION: PsaN

<400> SEQUENCE: 23
```

Met Ala Leu Ala Ser Tyr Cys Cys Arg Phe Val Pro Asp Asn Val Gln
1               5                   10                  15

Glu Leu Leu Asn Asn Lys Gly Lys Thr Val Thr Arg Asn Val Thr Ser
            20                  25                  30

Asp Ile Ser Gly Arg Arg Arg Leu Leu Ile Ser Ser Thr Ala Ala Ser
        35                  40                  45

Leu Leu Ala Val Ala Thr Thr Glu Ala Asn Asp Ser Gln Thr Ala Leu
    50                  55                  60

Leu Gln Lys Tyr Leu Lys Lys Ser Glu Glu Asn Lys Glu Lys Asn Asp
65                  70                  75                  80

Lys Ala Arg Met Asp Asp Tyr Tyr Lys Arg Asn Tyr Lys Asp Tyr Phe
                85                  90                  95

Gly Phe Val Glu Gly Pro Leu Arg Ser Lys Asp Lys Asp Gln Leu Ser
            100                 105                 110

Asp Ser Glu Arg Gly Ile Leu Glu Trp Leu Asp Lys Asn Lys
        115                 120                 125

```
<210> SEQ ID NO 24
<211> LENGTH: 129
<212> TYPE: PRT
<213> ORGANISM: Camelina sativa
<220> FEATURE:
```

<221> NAME/KEY: MISC_FEATURE
<222> LOCATION: (1)..(129)
<223> OTHER INFORMATION: PsaN

<400> SEQUENCE: 24

Met Ser Ser Val Gly Gln Ser Ile Leu Met Ala Leu Thr Val Thr Val
1               5                   10                  15

Asn Lys Tyr Ala Ser Tyr Asn Val Pro Ser Val Arg Arg Asn Asp Thr
            20                  25                  30

Lys Arg Asp Ser Leu Ala Ala Arg Thr Ala Asp Leu Gly Arg Arg Asn
        35                  40                  45

Val Leu Phe Ser Ser Ser Phe Ile Ala Ala Leu Thr Thr Ser
    50                  55                  60

Asp Gln Leu Leu Gln Lys Tyr Leu Lys Thr Glu Glu Asn Lys Ala
65              70                  75                  80

Lys Asn Asp Lys Glu Arg Leu Asp Gly Tyr Tyr Lys Arg Asn Tyr Lys
            85                  90                  95

Asp Tyr Phe Glu Phe Val Glu Gly Ser Ile Lys Gly Lys Thr Glu Ala
            100                 105                 110

Glu Leu Ser Glu Ser Glu Lys Arg Ile Leu Glu Trp Leu Lys Ala Asn
        115                 120                 125

Lys

<210> SEQ ID NO 25
<211> LENGTH: 126
<212> TYPE: PRT
<213> ORGANISM: Arachis duranensis
<220> FEATURE:
<221> NAME/KEY: MISC_FEATURE
<222> LOCATION: (1)..(126)
<223> OTHER INFORMATION: PsaN

<400> SEQUENCE: 25

Met Leu Met Ala Leu Thr Val Thr Ile Asn Lys Tyr Ala Ser Ser Asn
1               5                   10                  15

Leu Gln Ala Leu His Lys Thr Gln Gln Arg Lys Pro Pro Ser Thr Leu
            20                  25                  30

Thr Thr Ile Thr Asn Asn Val Gln Leu Gly Arg Arg Ser Leu Ile Leu
        35                  40                  45

Ser Thr Leu Ile Ala Thr Thr Gln Val Pro Glu Ser Arg Thr Gln Leu
    50                  55                  60

Leu Gln Lys Tyr Leu Lys Lys Ser Glu Glu Asn Lys Asp Lys Asn Asp
65              70                  75                  80

Lys Glu Arg Leu Glu Ser Tyr Tyr Lys Arg Asn Tyr Lys Asp Tyr Phe
            85                  90                  95

Asp Leu Met Glu Gly Thr Leu Arg Ala Lys Asn Asp Glu Gln Leu Ser
            100                 105                 110

Asp Thr Glu Lys Gly Ile Leu Asp Trp Leu Gln Arg Asn Lys
        115                 120                 125

<210> SEQ ID NO 26
<211> LENGTH: 126
<212> TYPE: PRT
<213> ORGANISM: Arachis ipaensis
<220> FEATURE:
<221> NAME/KEY: MISC_FEATURE
<222> LOCATION: (1)..(126)
<223> OTHER INFORMATION: PsaN

<400> SEQUENCE: 26

```
Met Leu Met Ala Leu Thr Val Ala Ile Asn Lys Tyr Ala Ser Ser Asn
1               5                   10                  15

Leu Gln Ala Leu His Lys Thr Gln Gln Arg Lys Pro Pro Ser Thr Leu
                20                  25                  30

Thr Thr Ile Thr Asn Asn Val Glu Leu Gly Arg Arg Ser Leu Ile Leu
            35                  40                  45

Ser Thr Leu Ile Ala Thr Thr Gln Val Pro Glu Ser Arg Thr Gln Leu
        50                  55                  60

Leu Gln Lys Tyr Leu Lys Lys Ser Glu Glu Asn Lys Asp Lys Asn Asp
65                  70                  75                  80

Lys Glu Arg Leu Glu Ser Tyr Tyr Lys Arg Asn Tyr Lys Asp Tyr Phe
                85                  90                  95

Asp Leu Met Glu Gly Thr Leu Arg Ala Lys Asn Asp Glu Gln Leu Ser
            100                 105                 110

Asp Thr Glu Lys Gly Ile Leu Asp Trp Leu Gln Arg Asn Lys
        115                 120                 125
```

<210> SEQ ID NO 27
<211> LENGTH: 129
<212> TYPE: PRT
<213> ORGANISM: Camelina sativa
<220> FEATURE:
<221> NAME/KEY: MISC_FEATURE
<222> LOCATION: (1)..(129)
<223> OTHER INFORMATION: PsaN

<400> SEQUENCE: 27

```
Met Ser Ser Val Gly Gln Ser Ile Leu Met Ala Leu Thr Val Thr Val
1               5                   10                  15

Asn Lys Tyr Ala Ser Ser Asn Val Gln Ser Val Arg Arg Asn Asp Thr
                20                  25                  30

Lys Arg Asp Ser Leu Ala Ala Arg Thr Ala Asp Leu Gly Arg Arg Asn
            35                  40                  45

Val Leu Phe Ser Ser Ser Phe Ile Ala Ala Ala Leu Thr Thr Ser
        50                  55                  60

Asp Gln Leu Leu Gln Lys Tyr Leu Lys Lys Thr Glu Glu Asn Lys Ala
65                  70                  75                  80

Lys Asn Asp Lys Glu Arg Leu Asp Gly Tyr Tyr Lys Arg Asn Tyr Lys
                85                  90                  95

Asp Tyr Phe Glu Phe Val Glu Gly Ser Ile Lys Gly Lys Thr Glu Ala
            100                 105                 110

Glu Leu Ser Glu Ser Glu Lys Arg Ile Leu Glu Trp Leu Lys Ala Asn
        115                 120                 125

Lys
```

<210> SEQ ID NO 28
<211> LENGTH: 133
<212> TYPE: PRT
<213> ORGANISM: Vigna angularis
<220> FEATURE:
<221> NAME/KEY: MISC_FEATURE
<222> LOCATION: (1)..(133)
<223> OTHER INFORMATION: PsaN

<400> SEQUENCE: 28

```
Met Ser Ser Ile Gly Gln Ser Ile Leu Met Ala Leu Thr Val Thr Leu
1               5                   10                  15

Asn Lys Tyr Ala Ser Ser Asn Leu Gln Ala Val His Arg Thr Gln Ala
```

```
            20                  25                  30
Lys Ala Ala His Thr Ser Asn Pro Thr Leu Ser Thr Lys Leu Glu Leu
            35                  40                  45

Gly Arg Arg Gly Leu Val Leu Ser Thr Leu Ile Ala Thr Thr Gln Ile
        50                  55                  60

Pro Asp Ser Arg Thr Gln Leu Leu Gln Lys Tyr Gln Lys Lys Ser Glu
 65                  70                  75                  80

Glu Asn Lys Glu Lys Asn Asp Lys Glu Arg Leu Asp Ser Tyr Tyr Lys
                85                  90                  95

Arg Asn Tyr Lys Asp Tyr Phe Glu Leu Met Glu Gly Thr Leu Lys Arg
            100                 105                 110

Arg Asp Gly Gly Glu Val Ser Asp Thr Glu Lys Gly Ile Leu Asp Trp
        115                 120                 125

Leu Gln Lys Asn Lys
        130

<210> SEQ ID NO 29
<211> LENGTH: 125
<212> TYPE: PRT
<213> ORGANISM: Zostera marina
<220> FEATURE:
<221> NAME/KEY: MISC_FEATURE
<222> LOCATION: (1)..(125)
<223> OTHER INFORMATION: PsaN

<400> SEQUENCE: 29

Met Val Phe Ser His Val Phe Gln Asn Met Val Lys Pro Gln Pro Gln
 1               5                  10                  15

Val Ser Pro Ser Val Ala Leu Gly Arg Gln Thr Thr Ile Arg Ala Thr
            20                  25                  30

Thr Gln Arg Gln Asp Leu Gly Arg Arg His Val Phe Ser Leu Leu Val
            35                  40                  45

Ala Ser Val Ala Val Ala Thr Leu Pro Glu Thr Ser Asp Ser Lys Lys
        50                  55                  60

Ser Ile Leu Gln Glu Tyr Leu Lys Lys Ser Glu Lys Asn Lys Ala Lys
 65                  70                  75                  80

Asn Asp Lys Glu Arg Leu Asp Asp Tyr Tyr Lys Arg Asn Tyr Lys Asp
                85                  90                  95

Tyr Phe Gly Phe Val Asp Ser Thr Lys Ser Asp Asp Gln Leu Ser Asp
            100                 105                 110

Thr Glu Lys Glu Ile Arg Asp Trp Leu Arg Ala Asn Lys
        115                 120                 125

<210> SEQ ID NO 30
<211> LENGTH: 129
<212> TYPE: PRT
<213> ORGANISM: Arabidopsis thaliana
<220> FEATURE:
<221> NAME/KEY: MISC_FEATURE
<222> LOCATION: (1)..(129)
<223> OTHER INFORMATION: PsaN

<400> SEQUENCE: 30

Met Ser Ser Ile Ser Gln Ser Ile Leu Met Ala Leu Thr Val Thr Val
 1               5                  10                  15

Asn Lys Tyr Ala Ser Ser Asn Val Gln Ala Val Arg Arg Asn Asp Thr
            20                  25                  30

Lys Arg His Ser Leu Thr Ala Pro Pro Ala Asp Leu Gly Arg Arg Asn
            35                  40                  45
```

```
Ile Leu Phe Ser Ser Thr Ser Phe Ile Ala Ala Ala Leu Thr Ser Ser
 50                  55                  60

Asp Gln Leu Leu Gln Lys Tyr Leu Lys Lys Thr Glu Glu Asp Lys Ala
 65                  70                  75                  80

Lys Asn Asp Lys Glu Arg Leu Asp Ser Phe Tyr Lys Arg Asn Tyr Lys
                 85                  90                  95

Asp Tyr Phe Glu Phe Val Glu Gly Ser Ile Lys Gly Lys Thr Glu Ala
            100                 105                 110

Glu Leu Ser Glu Ser Glu Lys Arg Ile Leu Glu Trp Leu Lys Ala Asn
        115                 120                 125

Lys

<210> SEQ ID NO 31
<211> LENGTH: 138
<212> TYPE: PRT
<213> ORGANISM: Citrus clementina
<220> FEATURE:
<221> NAME/KEY: MISC_FEATURE
<222> LOCATION: (1)..(138)
<223> OTHER INFORMATION: PsaN

<400> SEQUENCE: 31

Met Ser Ser Ile Asp Gln Ser Ile Leu Met Ala Leu Thr Val Thr Val
 1               5                  10                  15

Asn Lys Tyr Ala Ser Leu Asn Val Gln Ala Val His Arg Arg Glu Ala
                 20                  25                  30

Lys Thr Pro Lys Thr Thr Gly Ala Lys Ala Lys Ala Ala Ala Ala Phe
             35                  40                  45

His Asp Ile Gly Arg Arg Gly Leu Leu Leu Ser Ser Val Val Ala Ala
 50                  55                  60

Pro Gln Val Asn Asn Asp Asp Ser Lys Thr Gln Leu Leu Gln Lys Tyr
 65                  70                  75                  80

Leu Lys Lys Ser Glu Glu Asn Lys Ala Lys Asn Asp Lys Glu Arg Met
                 85                  90                  95

Asp Ser Tyr Tyr Lys Arg Asn Tyr Lys Asp Tyr Phe Asp Phe Ile Glu
            100                 105                 110

Gly Ser Leu Lys Gly Lys Ser Glu Gln Glu Leu Ser Glu Ser Glu Lys
        115                 120                 125

Gly Ile Leu Glu Trp Leu Lys Thr Asn Lys
    130                 135

<210> SEQ ID NO 32
<211> LENGTH: 138
<212> TYPE: PRT
<213> ORGANISM: Citrus sinensis
<220> FEATURE:
<221> NAME/KEY: MISC_FEATURE
<222> LOCATION: (1)..(138)
<223> OTHER INFORMATION: PsaN

<400> SEQUENCE: 32

Met Ser Ser Ile Gly Gln Ser Ile Leu Met Ala Leu Thr Val Thr Val
 1               5                  10                  15

Asn Lys Tyr Ala Ser Leu Asn Val Gln Ala Val His Arg Arg Glu Ala
                 20                  25                  30

Lys Thr Pro Lys Thr Thr Gly Ala Lys Ala Lys Ala Ala Ala Ala Phe
             35                  40                  45

Gln Asp Ile Gly Arg Arg Gly Leu Leu Leu Ser Ser Val Val Ala Ala
```

```
                50                  55                  60
Pro Gln Val Asn Asn Asp Asp Ser Lys Thr Gln Leu Gln Lys Tyr
65                  70                  75                  80

Leu Lys Lys Ser Glu Glu Asn Lys Ala Lys Asn Asp Lys Glu Arg Met
                85                  90                  95

Asp Ser Tyr Tyr Lys Arg Asn Tyr Lys Asp Tyr Phe Asp Phe Ile Glu
            100                 105                 110

Gly Ser Leu Lys Gly Lys Ser Glu Gln Glu Leu Ser Glu Ser Glu Lys
            115                 120                 125

Gly Ile Leu Glu Trp Leu Lys Thr Asn Lys
        130                 135

<210> SEQ ID NO 33
<211> LENGTH: 129
<212> TYPE: PRT
<213> ORGANISM: Eutrema salsugineum
<220> FEATURE:
<221> NAME/KEY: MISC_FEATURE
<222> LOCATION: (1)..(129)
<223> OTHER INFORMATION: PsaN

<400> SEQUENCE: 33

Met Ser Ser Ile Gly Gln Ser Ile Leu Met Ala Leu Thr Val Thr Val
1               5                   10                  15

Asn Lys Tyr Ala Ser Ser Asn Val Gln Ala Val Arg Arg Asn Glu Ile
                20                  25                  30

Lys Arg Asp Ser Leu Thr Ala Ser Thr Thr Asp Leu Gly Arg Arg Asn
            35                  40                  45

Ile Leu Phe Ser Ser Ser Ser Phe Leu Ala Ala Ala Leu Thr Thr Ser
        50                  55                  60

Asp Gln Leu Leu Gln Lys Tyr Leu Lys Lys Thr Glu Gly Asn Arg Thr
65                  70                  75                  80

Lys Asn Asp Lys Glu Arg Leu Asp Ser Tyr Tyr Lys Arg Asn Tyr Lys
                85                  90                  95

Asp Tyr Phe Glu Phe Val Glu Gly Ser Ile Lys Gly Lys Thr Glu Ala
            100                 105                 110

Glu Leu Thr Glu Ser Glu Lys Arg Ile Leu Glu Trp Leu Lys Ser Asn
        115                 120                 125

Lys

<210> SEQ ID NO 34
<211> LENGTH: 92
<212> TYPE: PRT
<213> ORGANISM: Dorcoceras hygrometricum
<220> FEATURE:
<221> NAME/KEY: MISC_FEATURE
<222> LOCATION: (1)..(92)
<223> OTHER INFORMATION: PsaN

<400> SEQUENCE: 34

Met Ser Glu Ala Asn Lys Gly Gly Gly Gly Gly Gly Arg Arg Asp
1               5                   10                  15

Leu Leu Leu Leu Ser Thr Ala Leu Val Thr Arg Ser Gln Thr Asp Leu
                20                  25                  30

Leu Asn Lys Tyr Leu Lys Lys Ser Gln Glu Asn Lys Ala Lys Asn Asp
            35                  40                  45

Lys Glu Arg Leu Asp Ser Tyr Asn Lys Arg Asn Tyr Arg Asp Tyr Phe
        50                  55                  60
```

```
Gly Leu Leu Glu Gly Gly Leu Arg Gln Lys Lys Asp Leu Ser Glu Ser
65                  70                  75                  80

Glu Lys Gly Ile Leu Glu Trp Leu Asp Ala Asn Lys
                85                  90
```

<210> SEQ ID NO 35
<211> LENGTH: 117
<212> TYPE: PRT
<213> ORGANISM: Coffea canephora
<220> FEATURE:
<221> NAME/KEY: MISC_FEATURE
<222> LOCATION: (1)..(117)
<223> OTHER INFORMATION: PsaN

<400> SEQUENCE: 35

```
Met Ala Thr Ser Ala Thr Val Ser Ile Ser Ala Leu Ser Asn Ile Gln
1               5                   10                  15

Gly Gly Glu Thr Arg Glu Arg Lys Gly Asn Ile Asn Ser Ala Lys Asp
                20                  25                  30

Lys Gly Arg Arg Glu Leu Leu Phe Ser Ala Ala Thr Val Ala Gln
                35                  40                  45

Val Thr Asp Ser Arg Thr Asp Leu Leu Lys Lys Tyr Leu Lys Lys Ser
50                  55                  60

Glu Glu Asn Lys Thr Lys Asn Asp Lys Glu Arg Leu Asp Ser Tyr Tyr
65                  70                  75                  80

Lys Arg Asn Tyr Lys Asp Tyr Phe Gly Leu Glu Gly Thr Leu Lys
                85                  90                  95

Gln Lys Lys Glu Gln Leu Ser Gly Ser Glu Lys Gly Ile Leu Glu Trp
                100                 105                 110

Leu Glu Lys Asn Lys
        115
```

<210> SEQ ID NO 36
<211> LENGTH: 126
<212> TYPE: PRT
<213> ORGANISM: Cynara cardunculus
<220> FEATURE:
<221> NAME/KEY: MISC_FEATURE
<222> LOCATION: (1)..(126)
<223> OTHER INFORMATION: PsaN

<400> SEQUENCE: 36

```
Met Ala Ile Arg Ala Tyr Ile Thr Thr Leu Ile Ser Ser Ile Gln Ala
1               5                   10                  15

Ala Glu Asn Thr Gln Glu Lys Gly Asn Gly Leu Ser Phe Arg Arg Lys
                20                  25                  30

Met Val Thr Glu Ser Asn Gly Arg Gly Gly Glu Gly Arg Arg Thr Leu
                35                  40                  45

Leu Leu Ser Ala Met Ala Ala Thr Gln Val Asn Asp Ser Lys Thr
50                  55                  60

Glu Leu Leu Gln Lys Tyr Leu Lys Lys Ser Glu Glu Asn Lys Thr Lys
65                  70                  75                  80

Asn Asp Lys Glu Arg Leu Asp Ser Tyr Tyr Lys Arg Asn Tyr Lys Asp
                85                  90                  95

Tyr Phe Gly Leu Glu Gly Thr Leu Arg Gln Lys Lys Glu Leu Thr
                100                 105                 110

Glu Thr Glu Lys Ser Ile Leu Asp Trp Leu Gln Ala Asn Lys
115                 120                 125
```

<210> SEQ ID NO 37
<211> LENGTH: 117
<212> TYPE: PRT
<213> ORGANISM: Sesamum indicum
<220> FEATURE:
<221> NAME/KEY: MISC_FEATURE
<222> LOCATION: (1)..(117)
<223> OTHER INFORMATION: PsaN

<400> SEQUENCE: 37

Met Ala Thr Thr Pro Ala Arg Val Cys Thr Leu Val Ser Leu Lys Val
1               5                   10                  15

Gln Ala Ala His Asp Ser Ser Arg Arg Ala Gly Val Glu Pro Lys Ala
            20                  25                  30

Gln Arg Lys Gly Gly Arg Arg Glu Leu Leu Leu Leu Ser Thr Thr Ala
        35                  40                  45

Leu Val Ala Asp Ser Arg Ala Asp Leu Leu Asn Lys Tyr Leu Lys Lys
    50                  55                  60

Ser Glu Glu Asn Lys Ala Lys Asn Asp Lys Glu Arg Leu Glu Ser Tyr
65                  70                  75                  80

Tyr Lys Arg Asn Tyr Arg Asp Tyr Phe Gly Leu Leu Glu Gly Asp Leu
                85                  90                  95

Lys Gln Lys Lys Glu Leu Ser Glu Ser Glu Lys Gly Ile Leu Glu Trp
            100                 105                 110

Leu Glu Asn Asn Lys
        115

<210> SEQ ID NO 38
<211> LENGTH: 146
<212> TYPE: PRT
<213> ORGANISM: Gossypium arboreum
<220> FEATURE:
<221> NAME/KEY: MISC_FEATURE
<222> LOCATION: (1)..(146)
<223> OTHER INFORMATION: PsaN

<400> SEQUENCE: 38

Met Gly Ser Ile Ala Gln Ser Val Leu Met Ala Leu Thr Val Thr Val
1               5                   10                  15

Asn Gln Phe Ala Ser Ser Asn Val His Ala Val His Arg Lys Gln Gly
            20                  25                  30

Lys Ser Pro Ser Pro Thr Ser Lys Pro Lys Pro Thr Asn Thr Lys Thr
        35                  40                  45

Ile Thr Ala Ala Ala Ala Asn Ala Gly Asp Thr Gly Ile Ala Arg Arg
    50                  55                  60

Gly Leu Ile Leu Ser Ala Val Ala Ser Ala Pro Gln Leu Asn Asp Ser
65                  70                  75                  80

Arg Thr Glu Leu Leu Lys Lys Tyr Leu Lys Thr Glu Glu Asn Lys
                85                  90                  95

Ala Lys Asn Asp Lys Glu Arg Met Glu Asn Tyr Tyr Arg Arg Asn Tyr
            100                 105                 110

Lys Asp Tyr Phe Glu Phe Val Glu Gly Thr Leu Lys Gly Lys Asp Glu
        115                 120                 125

Gln Gln Leu Ser Glu Ala Glu Lys Gly Ile Leu Asp Trp Leu Lys Ala
    130                 135                 140

Asn Lys
145

<210> SEQ ID NO 39

```
<211> LENGTH: 132
<212> TYPE: PRT
<213> ORGANISM: Jatropha curcas
<220> FEATURE:
<221> NAME/KEY: MISC_FEATURE
<222> LOCATION: (1)..(132)
<223> OTHER INFORMATION: PsaN

<400> SEQUENCE: 39

Met Ser Ser Ile Ser Gln Ser Val Leu Met Ala Leu Thr Val Thr Val
1               5                   10                  15

Asn Lys Phe Ala Ser Ser Asn Val His Ala Val Gln Arg Arg Glu Thr
            20                  25                  30

Lys Arg Ser Ser Ala Thr Thr Pro Pro Ser Ser Ala Phe Gly Arg
        35                  40                  45

Arg Gly Ile Phe Phe Ser Thr Leu Val Ala Ala Tyr Pro Val Ala Thr
    50                  55                  60

Asp Ser Lys Thr Glu Leu Leu Asn Lys Tyr Leu Lys Ser Glu Glu
65                  70                  75                  80

Asn Lys Thr Lys Asn Asp Lys Glu Arg Leu Asp Ser Tyr Tyr Lys Arg
            85                  90                  95

Asn Tyr Lys Asp Tyr Phe Asp Tyr Val Glu Gly Ser Leu Arg Gly Lys
        100                 105                 110

Lys Glu Gln Asp Leu Ser Glu Ser Glu Lys Ser Ile Leu Asp Trp Leu
    115                 120                 125

Lys Asn Asn Lys
    130

<210> SEQ ID NO 40
<211> LENGTH: 129
<212> TYPE: PRT
<213> ORGANISM: Manihot esculenta
<220> FEATURE:
<221> NAME/KEY: MISC_FEATURE
<222> LOCATION: (1)..(129)
<223> OTHER INFORMATION: PsaN

<400> SEQUENCE: 40

Met Ser Ser Ile Ser Gln Ser Val Leu Met Ala Leu Ala Val Thr Val
1               5                   10                  15

Asn Lys Phe Ala Ser Ser Asn Val His Ala Val Gln Arg Lys Glu Ser
            20                  25                  30

Lys Thr Ser Pro Ala Thr Ser Pro Ala Ala Phe Pro Arg Arg Gly Phe
        35                  40                  45

Leu Leu Ser Thr Leu Val Ala Ala Tyr Pro Leu Thr Thr Asp Ser Lys
    50                  55                  60

Thr Gln Leu Leu Asn Lys Tyr Leu Lys Ser Glu Glu Asn Lys Ala
65                  70                  75                  80

Lys Asn Asp Lys Glu Arg Leu Asp Ser Tyr Tyr Lys Arg Asn Tyr Lys
            85                  90                  95

Asp Tyr Phe Asp Phe Val Glu Gly Ser Leu Lys Gly Lys Lys Glu Gln
        100                 105                 110

Asp Leu Thr Glu Ser Glu Lys Gly Ile Leu Asp Trp Leu Lys Thr His
    115                 120                 125

Lys

<210> SEQ ID NO 41
<211> LENGTH: 123
<212> TYPE: PRT
```

<213> ORGANISM: Erythranthe guttata
<220> FEATURE:
<221> NAME/KEY: MISC_FEATURE
<222> LOCATION: (1)..(123)
<223> OTHER INFORMATION: PsaN

<400> SEQUENCE: 41

Met Ala Ile Ile Gly Arg Ile Phe Ile Asn Val Gln Ala Ala
1               5                   10                  15

Ala Ala Thr Asn Asn Ile Asn Arg Lys Glu Thr Lys Asn Arg Ala Ile
            20                  25                  30

Ser Asn Asn Lys Gly Gly Gly Arg Arg Glu Leu Leu Leu Ser Ser Thr
            35                  40                  45

Leu Ile Thr Thr Thr Ala Ile Val Leu Asp Ser Gln Thr Gln Leu Leu
        50                  55                  60

Asn Lys Tyr Leu Lys Lys Ser Glu Glu Asn Lys Ala Lys Asn Asp Lys
65                  70                  75                  80

Glu Arg Met Asp Ser Tyr Tyr Lys Arg Asn Tyr Lys Asp Tyr Phe Gln
                85                  90                  95

Leu Leu Glu Gly Asp Leu Arg Gln Lys Lys Asp Leu Thr Glu Ser Glu
            100                 105                 110

Lys Gly Ile Leu Glu Trp Leu Asp Lys Asn Lys
        115                 120

<210> SEQ ID NO 42
<211> LENGTH: 132
<212> TYPE: PRT
<213> ORGANISM: Phaseolus vulgaris
<220> FEATURE:
<221> NAME/KEY: MISC_FEATURE
<222> LOCATION: (1)..(132)
<223> OTHER INFORMATION: PsaN

<400> SEQUENCE: 42

Met Ser Ser Ile Gly Gln Thr Ile Leu Met Ala Leu Thr Ile Thr Leu
1               5                   10                  15

Asn Lys Tyr Ala Ser Ser Asn Leu Gln Ala Val His Arg Thr Arg Gly
            20                  25                  30

Lys Ala Pro His Thr Ser Thr Pro Asn Leu Ser Thr Lys Ile Glu Leu
            35                  40                  45

Gly Arg Arg Gly Val Val Leu Ser Thr Leu Ile Ala Thr Thr Gln Ile
        50                  55                  60

Pro Asp Ser Arg Thr Gln Leu Leu Gln Lys Tyr Gln Lys Lys Ser Glu
65                  70                  75                  80

Glu Asn Lys Glu Lys Asn Asp Lys Arg Leu Asp Ser Tyr Tyr Lys
                85                  90                  95

Arg Asn Tyr Lys Asp Tyr Phe Glu Leu Met Glu Gly Thr Leu Lys Arg
            100                 105                 110

Arg Asp Gly Glu Leu Ser Asp Ala Glu Lys Asp Ile Leu Glu Trp Leu
        115                 120                 125

Gln Lys Asn Lys
130

<210> SEQ ID NO 43
<211> LENGTH: 122
<212> TYPE: PRT
<213> ORGANISM: Nelumbo nucifera
<220> FEATURE:
<221> NAME/KEY: MISC_FEATURE
<222> LOCATION: (1)..(122)

<223> OTHER INFORMATION: PsaN

<400> SEQUENCE: 43

Met Ala Ser Ile Val Thr Ala Val Asn Gly Cys Glu Val Ala Leu Ser
1               5                   10                  15

Ser Ala Asp Gly Gly Tyr Gly Ala Arg Pro Ala Thr Leu Phe Arg
            20                  25                  30

Arg Arg Gly Phe Leu Leu Ser Val Met Phe Ala Pro Ser Thr Ala Ala
            35                  40                  45

Val Ala Ala Pro Gln Val Asn Asp Ser Arg Thr Glu Leu Leu Gln Arg
    50                  55                  60

Tyr Leu Lys Lys Ser Lys Glu Asn Arg Ala Lys Asn Glu Lys Glu Arg
65                  70                  75                  80

Leu Asp Asp Tyr Tyr Lys Arg Asn Tyr Lys Asp Tyr Phe Glu Phe Leu
                85                  90                  95

Glu Gly Ser Ile Lys Ala Lys Lys Asp Lys Leu Ser Glu Ala Glu Lys
            100                 105                 110

Gly Ile Leu Asp Trp Leu Gln Thr Asn Lys
            115                 120

<210> SEQ ID NO 44
<211> LENGTH: 132
<212> TYPE: PRT
<213> ORGANISM: Vigna radiata
<220> FEATURE:
<221> NAME/KEY: MISC_FEATURE
<222> LOCATION: (1)..(132)
<223> OTHER INFORMATION: PsaN

<400> SEQUENCE: 44

Met Ser Ser Ile Gly Gln Ser Ile Leu Met Ala Leu Thr Val Thr Leu
1               5                   10                  15

Asn Lys Tyr Ala Ser Ser Asn Leu Gln Ala Val His Arg Thr Gln Gly
            20                  25                  30

Lys Gly Ala His Thr Ser Thr Pro Thr Leu Ser Thr Lys Leu Glu Leu
            35                  40                  45

Gly Arg Arg Gly Leu Val Leu Ser Thr Leu Ile Ala Thr Thr Gln Ile
    50                  55                  60

Pro Asp Ser Arg Thr Gln Leu Leu Gln Lys Tyr Gln Lys Lys Ser Glu
65                  70                  75                  80

Glu Asn Lys Glu Lys Asn Asp Lys Gly Arg Leu Asp Ser Tyr Tyr Lys
                85                  90                  95

Arg Asn Tyr Lys Asp Tyr Phe Glu Leu Met Glu Gly Thr Leu Lys Arg
                100                 105                 110

Arg Asp Gly Asn Val Ser Asp Thr Glu Lys Gly Ile Leu Asp Trp Leu
            115                 120                 125

Gln Lys Asn Lys
    130

<210> SEQ ID NO 45
<211> LENGTH: 131
<212> TYPE: PRT
<213> ORGANISM: Eucalyptus grandis
<220> FEATURE:
<221> NAME/KEY: MISC_FEATURE
<222> LOCATION: (1)..(131)
<223> OTHER INFORMATION: PsaN

<400> SEQUENCE: 45

Met Ala Ser Ile Ala Gln Asn Val Leu Met Ala Leu Thr Ala Thr Val
1               5                   10                  15

Asn Lys Phe Ala Ser Ser Asn Val Gln Ala Val Pro Arg Gly Glu Gly
            20                  25                  30

Trp Arg Arg Lys Pro Arg Ala Thr Pro Ala Asp Ser Cys Gln Ser Val
        35                  40                  45

Ala Gly Thr Arg Arg Cys Leu Leu Leu Ser Ala Val Ala Val Gly
    50                  55                  60

Asp Ser Arg Thr Glu Ile Leu Glu Lys Tyr Leu Lys Ser Glu Glu
65                  70                  75                  80

Asn Lys Ser Lys Asn Asp Lys Glu Arg Leu Glu Ser Tyr Tyr Lys Arg
                85                  90                  95

Asn Tyr Lys Asp Tyr Phe Glu Phe Val Glu Gly Ser Leu Arg Asn Lys
            100                 105                 110

Thr Asp Gln Leu Thr Glu Ser Glu Lys Gly Ile Leu Asp Trp Leu Lys
        115                 120                 125

Ser Asn Lys
    130

<210> SEQ ID NO 46
<211> LENGTH: 135
<212> TYPE: PRT
<213> ORGANISM: Populus trichocarpa
<220> FEATURE:
<221> NAME/KEY: MISC_FEATURE
<222> LOCATION: (1)..(135)
<223> OTHER INFORMATION: PsaN

<400> SEQUENCE: 46

Met Ser Ser Ile Ser Gln Ser Val Leu Met Ala Leu Thr Val Thr Phe
1               5                   10                  15

Asn Lys Phe Ala Ser Ser Asn Val Asn Ala Val His Lys Lys Glu Ser
            20                  25                  30

Lys Arg Ala Ala Ala Thr Thr Ala Lys Ala Ala Ser Arg Ala Ala
        35                  40                  45

Asp Ile Gly Arg Arg Gly Val Leu Leu Ser Thr Val Gly Val Tyr
    50                  55                  60

Ser Val Asn Asp Ser Arg Ile Glu Leu Leu Lys Lys Tyr Leu Lys Lys
65                  70                  75                  80

Ser Glu Asp Asn Lys Thr Lys Asn Asp Lys Glu Arg Met Asp Ser Tyr
                85                  90                  95

Tyr Lys Arg Asn Tyr Lys Asp Tyr Phe Asp Phe Val Glu Gly Ser Leu
            100                 105                 110

Lys Gly Lys Asn Glu Gln Asp Leu Thr Glu Ser Glu Lys Gly Ile Leu
        115                 120                 125

Asp Trp Leu Lys Lys Asn Lys
    130                 135

<210> SEQ ID NO 47
<211> LENGTH: 128
<212> TYPE: PRT
<213> ORGANISM: Brassica oleracea
<220> FEATURE:
<221> NAME/KEY: MISC_FEATURE
<222> LOCATION: (1)..(128)
<223> OTHER INFORMATION: PsaN

<400> SEQUENCE: 47

Met Ser Ser Val Gly Gln Ser Ile Leu Met Ala Leu Thr Val Thr Val

```
1               5                   10                  15
Asn Lys Tyr Ala Ser Ser Asn Val Gln Ala Val Arg Arg Asn Glu Ser
                20                  25                  30

Thr Ser Leu Thr Ala Ser Thr Thr Asp Leu Arg Arg Asn Ile Ile
            35                  40                  45

Phe Ser Ser Ser Ser Phe Leu Ala Ala Leu Thr Thr Ser Asp
        50                  55                  60

Gln Leu Leu Gln Lys Tyr Leu Lys Lys Ser Glu Glu Asn Lys Thr Lys
65                  70                  75                  80

Asn Asp Lys Glu Arg Leu Asp Ser Tyr Tyr Lys Arg Asn Tyr Lys Asp
                85                  90                  95

Tyr Phe Glu Phe Val Glu Gly Ser Thr Lys Gly Lys Thr Glu Ala Glu
                100                 105                 110

Leu Ser Glu Ser Glu Lys Arg Ile Leu Glu Trp Leu Lys Ala Asn Lys
            115                 120                 125
```

<210> SEQ ID NO 48
<211> LENGTH: 119
<212> TYPE: PRT
<213> ORGANISM: Solanum tuberosum
<220> FEATURE:
<221> NAME/KEY: MISC_FEATURE
<222> LOCATION: (1)..(119)
<223> OTHER INFORMATION: PsaN

<400> SEQUENCE: 48

```
Met Ala Leu Asn Ala Gly Asn Cys Thr Tyr Phe Phe Ser Arg Phe Tyr
1               5                   10                  15

Val Gln Ala Ile Asn Thr Lys Glu Ile Arg Val Lys Thr Lys Lys Glu
                20                  25                  30

Thr Trp Gln Gly Arg Arg Glu Leu Leu Phe Ser Thr Ile Ala Ile
            35                  40                  45

Val Gln Val Asn Asp Ser Gln Thr Glu Leu Leu Lys Arg Tyr Leu Lys
    50                  55                  60

Lys Ser Glu Glu Asn Lys Thr Lys Asn Asp Lys Glu Arg Leu Asp Ser
65                  70                  75                  80

Tyr Tyr Lys Arg Asn Tyr Arg Asp Tyr Phe Gly Tyr Leu Glu Gly Asn
                85                  90                  95

Leu Lys Asp Lys Lys Glu Glu Leu Thr Glu Ser Glu Gln Gly Ile Leu
                100                 105                 110

Asp Trp Leu Glu Lys Asn Lys
            115
```

<210> SEQ ID NO 49
<211> LENGTH: 130
<212> TYPE: PRT
<213> ORGANISM: Brassica napus
<220> FEATURE:
<221> NAME/KEY: MISC_FEATURE
<222> LOCATION: (1)..(130)
<223> OTHER INFORMATION: PsaN

<400> SEQUENCE: 49

```
Met Ser Ser Val Gly Gln Ser Ile Leu Met Ala Leu Thr Val Thr Val
1               5                   10                  15

Asn Lys Tyr Ala Ser Ser Asn Val Gln Ala Val Arg Arg Asn Glu Thr
                20                  25                  30

Lys Arg Thr Ser Leu Thr Ala Ser Thr Thr Asp Leu Arg Arg Arg Asn
            35                  40                  45
```

```
Ile Ile Phe Ser Ser Ser Ser Phe Leu Ala Ala Ala Leu Thr Thr
    50                  55                  60

Ser Asp Gln Leu Leu Gln Lys Tyr Leu Lys Lys Ser Glu Glu Asn Lys
65                  70                  75                  80

Thr Lys Asn Asp Lys Glu Arg Leu Asp Ser Tyr Tyr Lys Arg Asn Tyr
                85                  90                  95

Lys Asp Tyr Phe Glu Phe Val Glu Gly Ser Thr Lys Gly Lys Thr Glu
            100                 105                 110

Ala Glu Leu Ser Glu Ser Glu Lys Arg Ile Leu Glu Trp Leu Lys Ala
        115                 120                 125

Asn Lys
    130

<210> SEQ ID NO 50
<211> LENGTH: 132
<212> TYPE: PRT
<213> ORGANISM: Cicer arietinum
<220> FEATURE:
<221> NAME/KEY: MISC_FEATURE
<222> LOCATION: (1)..(132)
<223> OTHER INFORMATION: PsaN

<400> SEQUENCE: 50

Met Ser Ser Ser Ile Gly Gln Ser Ile Leu Met Ala Leu Thr Val Thr
1               5                   10                  15

Val Asn Lys Tyr Ala Ser Ser Asn Met His Leu Gln Ala Val His Lys
                20                  25                  30

Lys Gln Arg Gln Ala Thr Asn Ser Asn Leu Ser Thr Asn Ala Gly Phe
            35                  40                  45

Gly Arg Arg Gly Leu Val Leu Ser Thr Val Ile Ala Ala Thr Gln Val
        50                  55                  60

Pro Asp Ser Arg Thr Gln Leu Leu Gln Lys Tyr Leu Glu Lys Ser Glu
65                  70                  75                  80

Glu Asn Lys Asp Lys Asn Asp Lys Glu Arg Leu Asp Ser Tyr Tyr Lys
                85                  90                  95

Arg Asn Tyr Lys Asp Tyr Phe Glu Phe Ile Glu Gly Ser Leu Lys Gly
            100                 105                 110

Lys Asp Gly Lys Leu Ser Glu Ala Glu Lys Gly Ile Leu Asp Trp Leu
        115                 120                 125

Gln Thr Asn Lys
    130

<210> SEQ ID NO 51
<211> LENGTH: 135
<212> TYPE: PRT
<213> ORGANISM: Populus euphratica
<220> FEATURE:
<221> NAME/KEY: MISC_FEATURE
<222> LOCATION: (1)..(135)
<223> OTHER INFORMATION: PsaN

<400> SEQUENCE: 51

Met Ser Ser Val Ser Gln Ser Val Leu Met Ala Leu Thr Val Thr Phe
1               5                   10                  15

Asn Lys Phe Ala Ser Ser Asn Val Asn Ala Val His Lys Lys Glu Gly
                20                  25                  30

Lys Arg Ala Ala Ala Ala Thr Thr Ala Lys Ala Ala Ser Arg Ala Ala
            35                  40                  45
```

```
Asp Ile Gly Arg Arg Gly Val Leu Leu Ser Thr Val Gly Val Tyr
    50                  55                  60

Ser Val Asn Asp Ser Arg Thr Glu Leu Leu Lys Lys Tyr Leu Lys
65                  70                  75                  80

Ser Glu Asp Asn Lys Thr Lys Asn Asp Lys Glu Arg Thr Asp Ser Tyr
                    85                  90                  95

Tyr Lys Arg Asn Tyr Lys Asp Tyr Phe Asp Phe Val Glu Gly Ser Leu
                100                 105                 110

Lys Gly Lys Asn Glu Gln Asp Leu Thr Glu Ser Glu Lys Gly Ile Leu
            115                 120                 125

Asp Trp Leu Lys Lys Asn Lys
    130                 135

<210> SEQ ID NO 52
<211> LENGTH: 119
<212> TYPE: PRT
<213> ORGANISM: Solanum pennellii
<220> FEATURE:
<221> NAME/KEY: MISC_FEATURE
<222> LOCATION: (1)..(119)
<223> OTHER INFORMATION: PsaN

<400> SEQUENCE: 52

Met Ala Leu Asn Thr Gly Asn Cys Thr Tyr Ser Phe Ser Arg Phe His
1               5                   10                  15

Val Gln Ala Ile Asn Thr Lys Glu Ile Lys Val Lys Thr Lys Lys Glu
                20                  25                  30

Thr Trp Gln Gly Arg Arg Glu Phe Leu Phe Thr Thr Ile Ile Ala Ile
            35                  40                  45

Val Gln Val Asn Asp Ser Gln Thr Glu Leu Leu Lys Arg Tyr Leu Lys
    50                  55                  60

Lys Ser Glu Glu Asn Lys Thr Lys Asn Asp Lys Glu Arg Leu Asp Ser
65                  70                  75                  80

Tyr Tyr Lys Arg Asn Tyr Arg Asp Tyr Phe Gly Tyr Leu Glu Gly Thr
                85                  90                  95

Leu Lys Asp Lys Lys Glu Glu Leu Thr Glu Ser Glu Gln Gly Ile Leu
                100                 105                 110

Asp Trp Leu Glu Lys Asn Lys
            115

<210> SEQ ID NO 53
<211> LENGTH: 130
<212> TYPE: PRT
<213> ORGANISM: Brassica napus
<220> FEATURE:
<221> NAME/KEY: MISC_FEATURE
<222> LOCATION: (1)..(130)
<223> OTHER INFORMATION: PsaN

<400> SEQUENCE: 53

Met Ser Ser Val Gly Gln Ser Ile Leu Met Ala Leu Thr Val Thr Val
1               5                   10                  15

Asn Lys Tyr Ala Ser Ser Asn Val Gln Ala Val Arg Arg Asn Glu Thr
                20                  25                  30

Lys Arg Asp Ser Leu Thr Ala Ser Thr Thr Asp Leu Arg Arg Arg Asn
            35                  40                  45

Ile Ile Phe Ser Ser Ser Ser Phe Leu Ala Ala Ala Leu Thr Thr
    50                  55                  60

Ser Asp Gln Leu Leu Gln Lys Tyr Leu Lys Lys Ser Glu Glu Asn Lys
```

```
                65                   70                  75                  80
Thr Lys Asn Asp Lys Glu Arg Leu Asp Ser Tyr Tyr Lys Arg Asn Tyr
                    85                  90                  95

Lys Asp Tyr Phe Glu Phe Val Glu Gly Ser Thr Lys Gly Lys Thr Glu
            100                 105                 110

Ala Glu Leu Ser Glu Ser Glu Lys Arg Ile Leu Glu Trp Leu Lys Ala
        115                 120                 125

Asn Lys
    130

<210> SEQ ID NO 54
<211> LENGTH: 119
<212> TYPE: PRT
<213> ORGANISM: Solanum lycopersicum
<220> FEATURE:
<221> NAME/KEY: MISC_FEATURE
<222> LOCATION: (1)..(119)
<223> OTHER INFORMATION: PsaN

<400> SEQUENCE: 54

Met Ala Leu Asn Thr Gly Asn Cys Thr Tyr Ser Phe Ser Arg Phe His
1               5                   10                  15

Val Gln Ala Ile Asn Thr Lys Glu Ile Lys Val Lys Thr Lys Lys Glu
            20                  25                  30

Thr Trp Gln Gly Arg Arg Glu Phe Leu Phe Ser Thr Ile Ile Ala Ile
        35                  40                  45

Val Gln Val Asn Asp Ser Gln Thr Glu Leu Leu Lys Arg Tyr Leu Lys
    50                  55                  60

Lys Ser Glu Glu Asn Lys Thr Lys Asn Asp Lys Glu Arg Leu Asp Ser
65                  70                  75                  80

Tyr Tyr Lys Arg Asn Tyr Arg Asp Tyr Phe Gly Tyr Leu Glu Gly Thr
                85                  90                  95

Leu Lys Asp Lys Lys Glu Glu Leu Thr Glu Ser Glu Gln Gly Ile Leu
            100                 105                 110

Asp Trp Leu Glu Lys Asn Lys
        115

<210> SEQ ID NO 55
<211> LENGTH: 130
<212> TYPE: PRT
<213> ORGANISM: Brassica rapa
<220> FEATURE:
<221> NAME/KEY: MISC_FEATURE
<222> LOCATION: (1)..(130)
<223> OTHER INFORMATION: PsaN

<400> SEQUENCE: 55

Met Ser Ser Val Gly Gln Ser Ile Leu Met Ala Leu Thr Val Thr Val
1               5                   10                  15

Asn Lys Tyr Ala Ser Ser Asn Val Gln Ala Val Arg Arg Asn Glu Thr
            20                  25                  30

Lys Arg Thr Ser Leu Thr Ala Ser Thr Thr Asp Leu Arg Arg Arg Asn
        35                  40                  45

Ile Ile Phe Ser Ser Ser Ser Phe Leu Ala Ala Ala Leu Thr Thr
    50                  55                  60

Ser Asp Gln Leu Leu Gln Lys Tyr Leu Lys Lys Thr Glu Glu Asn Lys
65                  70                  75                  80

Thr Lys Asn Asp Lys Glu Arg Leu Asp Ser Tyr Tyr Lys Arg Asn Tyr
                85                  90                  95
```

Lys Asp Tyr Phe Glu Phe Val Glu Gly Ser Thr Lys Gly Lys Thr Glu
            100                 105                 110

Ala Glu Leu Ser Glu Ser Glu Lys Arg Ile Leu Glu Trp Leu Lys Ala
        115                 120                 125

Asn Lys
    130

<210> SEQ ID NO 56
<211> LENGTH: 131
<212> TYPE: PRT
<213> ORGANISM: Beta vulgaris
<220> FEATURE:
<221> NAME/KEY: MISC_FEATURE
<222> LOCATION: (1)..(131)
<223> OTHER INFORMATION: PsaN

<400> SEQUENCE: 56

Met Ala Leu Ala Ser Tyr Ser Cys Lys Leu Ile Leu Pro Ser Asn Ala
1               5                   10                  15

Gln Glu Leu His Asp Gln Gly Lys Asp Asn Thr Asp Glu Ser Thr Ala
            20                  25                  30

Lys Ser Val Gly Ser Asn Ile Thr Gly Arg Arg Leu Phe Ile Ser
        35                  40                  45

Ser Thr Ala Ala Thr Ala Leu Val Ala Ala Thr Ile Glu Ala Asn Asp
    50                  55                  60

Ser Lys Thr Ala Leu Leu Gln Arg Tyr Leu Lys Lys Ser Glu Glu Asn
65                  70                  75                  80

Lys Val Lys Asn Asp Lys Glu Arg Leu Asp Gly Tyr Tyr Lys Arg Asn
                85                  90                  95

Tyr Lys Asp Tyr Phe Gly Phe Ala Glu Gly Ser Leu Lys Ala Lys Asp
            100                 105                 110

Lys Glu Gln Leu Ser Glu Ser Glu Arg Gly Ile Leu Asp Trp Leu Glu
        115                 120                 125

Lys Asn Lys
    130

<210> SEQ ID NO 57
<211> LENGTH: 135
<212> TYPE: PRT
<213> ORGANISM: Ricinus communis
<220> FEATURE:
<221> NAME/KEY: MISC_FEATURE
<222> LOCATION: (1)..(135)
<223> OTHER INFORMATION: PsaN

<400> SEQUENCE: 57

Met Ser Ser Ile Ser Gln Ser Val Leu Met Ala Leu Thr Val Thr Val
1               5                   10                  15

Asn Lys Phe Ala Ser Ser Asn Val His Ser Val Gln Arg Arg Glu Ala
            20                  25                  30

Ser Lys Lys Ser Ser Pro Thr Ser Gly Ser Ala Thr Thr Ala Phe Pro
        35                  40                  45

Ile Phe Gly Arg Arg Gly Ile Leu Leu Ser Ala Leu Val Ala Ala Tyr
    50                  55                  60

Pro Val Asn Asp Ser Lys Thr Glu Leu Leu Lys Lys Tyr Leu Lys Lys
65                  70                  75                  80

Ser Glu Glu Asn Arg Thr Lys Asn Asp Lys Arg Leu Asp Ser Tyr
                85                  90                  95

```
Tyr Lys Arg Asn Tyr Lys Asp Tyr Phe Asp Leu Val Glu Gly Gly Leu
            100                 105                 110

Arg Gly Lys Lys Glu Gln Asp Leu Ser Glu Ser Glu Lys Gly Ile Leu
        115                 120                 125

Asp Trp Leu Lys Asn Asn Lys
    130                 135

<210> SEQ ID NO 58
<211> LENGTH: 202
<212> TYPE: PRT
<213> ORGANISM: Marchantia polymorpha
<220> FEATURE:
<221> NAME/KEY: MISC_FEATURE
<222> LOCATION: (1)..(202)
<223> OTHER INFORMATION: PsaN

<400> SEQUENCE: 58

Met Leu Thr Leu Ser Asn Ala Phe Gly Cys Pro Val Ser Cys Cys Ser
1               5                   10                  15

Gln Ala Ala Pro Ser Val Pro Ser Asp Asn Ser Val Thr Ser Arg Ile
            20                  25                  30

Thr Ser Ala Ala Ser Cys Arg Ala Ala Val Ser Val Gly Ser Gly Asn
        35                  40                  45

Gly Gln Asn Ser Glu Glu Arg Ser Arg Gly Ala Ser Ser Gly Arg Arg
    50                  55                  60

Leu Phe Ile Ser Met Met Ser Gly Thr Val Leu Leu Asn Tyr Leu Glu
65                  70                  75                  80

Lys Thr Ser Ala Ala Ala Glu Glu Val Asn Phe Asp Ser Val Ala Ser
                85                  90                  95

Glu Ser Leu Ala Thr Asp Pro Gln Val Thr Pro Pro Glu Leu Ala Leu
            100                 105                 110

Pro Asp Pro Pro Ala Val Glu Gly Ala Ala Thr Ala Glu Val Pro Ala
        115                 120                 125

Ala Ser Glu Ala Asn Ala Pro Ala Gly Asn Ala Leu Ile Gln Lys Leu
    130                 135                 140

Leu Ala Arg Ser Lys Ala Asn Lys Glu Lys Asn Asp Lys Ala Arg Leu
145                 150                 155                 160

Asp Asp Tyr Tyr Arg Arg Asn Tyr Lys Glu Tyr Phe Glu Phe Val Glu
                165                 170                 175

Gly Thr Ile Arg Asn Lys Lys Lys Glu Glu Leu Thr Glu Ala Glu Lys
            180                 185                 190

Gly Ile Ile Glu Trp Leu Ala Lys Asn Lys
        195                 200

<210> SEQ ID NO 59
<211> LENGTH: 130
<212> TYPE: PRT
<213> ORGANISM: Tarenaya hassleriana
<220> FEATURE:
<221> NAME/KEY: MISC_FEATURE
<222> LOCATION: (1)..(130)
<223> OTHER INFORMATION: PsaN

<400> SEQUENCE: 59

Met Ser Ser Met Arg Gln Ser Ile Leu Met Ala Leu Thr Val Thr Val
1               5                   10                  15

Asn Lys Tyr Ala Ser Ser Asn Val Gln Ala Val Arg Arg Asn Asp Ser
            20                  25                  30

Lys Ala Gly Ser Val Thr Ala Asn Ala Asn Ala Asp Phe Gly Pro Gln
```

```
                35                  40                  45
Arg Arg Asn Phe Leu Leu Ser Ser Phe Leu Ala Ala Val Asn Ala
 50                  55                  60

Arg Asp Gln Leu Leu Gln Lys Tyr Leu Lys Lys Ser Asp Glu Asn Lys
 65                  70                  75                  80

Ala Lys Asn Asp Lys Glu Arg Leu Glu Ser Tyr Tyr Lys Arg Asn Tyr
                 85                  90                  95

Lys Asp Tyr Phe Glu Phe Val Glu Gly Ser Ile Lys Gly Lys Arg Glu
            100                 105                 110

Glu Glu Leu Thr Gln Ser Glu Lys Ser Ile Leu Asp Trp Leu Lys Ser
            115                 120                 125

Asn Lys
    130

<210> SEQ ID NO 60
<211> LENGTH: 119
<212> TYPE: PRT
<213> ORGANISM: Vitis vinifera
<220> FEATURE:
<221> NAME/KEY: MISC_FEATURE
<222> LOCATION: (1)..(119)
<223> OTHER INFORMATION: PsaN

<400> SEQUENCE: 60

Met Ala Gln Ala Val Asn Ser Leu Ser Lys Phe Ala Ser Gln Asn Val
 1               5                  10                  15

Gln Ala Ile His Gly Gly Lys Gly Lys Gly Ser Ile Thr Thr Arg Thr
             20                  25                  30

Thr Glu Ile Gly Arg Arg Ser Gly Leu Leu Leu Ser Ser Val Leu Ala
         35                  40                  45

Ala Ser Gln Val Ser Asp Ser Arg Thr Glu Leu Leu Lys Lys Tyr Leu
 50                  55                  60

Lys Lys Ser Glu Glu Asn Lys Ala Lys Asn Asp Lys Glu Arg Leu Asp
 65                  70                  75                  80

Ser Phe Tyr Lys Arg Asn Tyr Lys Asp Tyr Phe Glu Phe Val Glu Gly
                 85                  90                  95

Ser Leu Ala Gly Lys Glu Gln Leu Ser Glu Ser Glu Lys Gly Ile Leu
            100                 105                 110

Asp Trp Leu Lys Lys Asn Lys
            115

<210> SEQ ID NO 61
<211> LENGTH: 131
<212> TYPE: PRT
<213> ORGANISM: Medicago truncatula
<220> FEATURE:
<221> NAME/KEY: MISC_FEATURE
<222> LOCATION: (1)..(131)
<223> OTHER INFORMATION: PsaN

<400> SEQUENCE: 61

Met Ser Ser Ile Gly Gln Thr Met Leu Met Ala Leu Thr Val Thr Val
 1               5                  10                  15

Asn Lys Tyr Ala Ser Ser Asn Val Gln Ala Val His Asn Arg Lys Gln
             20                  25                  30

Ala Asn Pro Thr Leu Arg Ser Thr Asn Leu Glu Phe Gly Arg Arg Gly
         35                  40                  45

Leu Val Leu Ser Thr Val Ile Ala Ala Thr Ala Thr Gln Asp Pro Glu
 50                  55                  60
```

```
Ser Arg Thr Leu Leu Gln Lys Tyr Leu Lys Thr Glu Glu Asn
 65                  70                  75                  80

Lys Glu Lys Asn Asp Lys Glu Arg Val Asp Ser Tyr Tyr Lys Arg Asn
                 85                  90                  95

Tyr Lys Asp Tyr Phe Glu Phe Val Glu Gly Leu Gln Gly Lys Glu
            100                 105                 110

Glu Gly Lys Leu Ser Glu Ala Glu Lys Gly Ile Leu Asp Trp Leu Lys
        115                 120                 125

Ala Asn Lys
    130

<210> SEQ ID NO 62
<211> LENGTH: 131
<212> TYPE: PRT
<213> ORGANISM: Pyrus x bretschneideri
<220> FEATURE:
<221> NAME/KEY: MISC_FEATURE
<222> LOCATION: (1)..(131)
<223> OTHER INFORMATION: PsaN

<400> SEQUENCE: 62

Met Ser Ser Ile Gly Gln Ser Ile Leu Met Ala Leu Thr Val Thr Val
  1               5                  10                  15

Asn Lys Phe Ala Ser Ser Asn Val His Ala Val His Arg Lys Gln Lys
                 20                  25                  30

Lys Ala Pro Lys Lys Ser Thr Ser Ala Thr Ser Thr Asn Asp Ile Gly
            35                  40                  45

Arg Arg Gly Leu Leu Leu Ser Ala Leu Val Ala Thr Pro Pro Leu Ser
 50                  55                  60

Asp Ser Gly Ala Glu Leu Leu Lys Lys Tyr Leu Lys Lys Ser Glu Glu
 65                  70                  75                  80

Asn Lys Ala Lys Asn Asp Lys Glu Arg Met Asp Ser Tyr Phe Lys Arg
                 85                  90                  95

Asn Tyr Lys Asp Tyr Phe Glu Phe Glu Glu Gly Thr Ile Arg Ala Lys
            100                 105                 110

Lys Gly Glu Leu Thr Glu Ser Glu Lys Gly Ile Leu Asp Trp Leu Gln
        115                 120                 125

Asn Asn Lys
    130

<210> SEQ ID NO 63
<211> LENGTH: 131
<212> TYPE: PRT
<213> ORGANISM: Malus domestica
<220> FEATURE:
<221> NAME/KEY: MISC_FEATURE
<222> LOCATION: (1)..(131)
<223> OTHER INFORMATION: PsaN

<400> SEQUENCE: 63

Met Ser Ser Ile Gly Gln Ser Ile Leu Met Ala Leu Thr Val Thr Val
  1               5                  10                  15

Asn Lys Phe Ala Ser Ser Asn Val Gln Ala Val His Arg Lys Gln Lys
                 20                  25                  30

Lys Ala Pro Lys Lys Ser Thr Ser Ala Thr Ser Thr Asn Asp Ile Gly
            35                  40                  45

Arg Arg Gly Leu Leu Leu Ser Ala Leu Val Ala Thr Pro Pro Leu Ser
 50                  55                  60
```

Asp Ser Gly Ala Glu Leu Leu Lys Lys Tyr Leu Lys Lys Ser Glu Glu
65                  70                  75                  80

Asn Lys Ala Lys Asn Asp Lys Glu Arg Met Asp Ser Tyr Phe Lys Arg
                85                  90                  95

Asn Tyr Lys Asp Tyr Phe Glu Phe Glu Glu Gly Thr Ile Arg Ala Lys
            100                 105                 110

Lys Gly Glu Leu Thr Glu Ser Glu Lys Gly Ile Leu Asp Trp Leu Gln
        115                 120                 125

Asn Asn Lys
    130

<210> SEQ ID NO 64
<211> LENGTH: 111
<212> TYPE: PRT
<213> ORGANISM: Daucus carota
<220> FEATURE:
<221> NAME/KEY: MISC_FEATURE
<222> LOCATION: (1)..(111)
<223> OTHER INFORMATION: PsaN

<400> SEQUENCE: 64

Met Ala Ile Ser Ala Thr Leu Thr Arg Ile Val Ser Ser Ile Val Lys
1               5                   10                  15

Val Val Ser Thr Lys Glu Asp Ser Thr Thr Ser Val Pro His Gln Pro
                20                  25                  30

Arg Arg Gly Ile Leu Leu Ser Thr Ile Phe Val Ala Ala Asp Ser Gln
            35                  40                  45

Thr Asp Leu Leu Gln Lys Tyr Leu Lys Lys Ser Glu Glu Asn Lys Ser
50                  55                  60

Lys Tyr Asp Lys Glu Arg Leu Asp Ser Tyr Tyr Lys Arg Asn Tyr Lys
65                  70                  75                  80

Asp Tyr Phe Gly Phe Ser Glu Gly Ala Leu Lys Glu Lys Lys Asp Leu
                85                  90                  95

Thr Glu Ser Glu Lys Gly Ile Leu Glu Trp Leu Glu Ala Asn Lys
            100                 105                 110

<210> SEQ ID NO 65
<211> LENGTH: 133
<212> TYPE: PRT
<213> ORGANISM: Amborella trichopoda
<220> FEATURE:
<221> NAME/KEY: MISC_FEATURE
<222> LOCATION: (1)..(133)
<223> OTHER INFORMATION: PsaN

<400> SEQUENCE: 65

Met Leu Ser Gln Lys Ser Tyr Ser Phe Met Ala Val Gly Leu Leu Ser
1               5                   10                  15

Leu Ser Thr Asn Pro Lys Ser Leu His Ser Tyr Ile Ser Pro Phe Asn
                20                  25                  30

Gly Trp Arg Ser Asn Ser Arg Pro Arg Pro Leu Lys Glu Val Gly Arg
            35                  40                  45

Arg Gly Phe Leu Ser Leu Leu Leu Thr Pro Thr Val Val Phe Ser Glu
50                  55                  60

Thr Asn Ser Ser Lys Asn Ala Leu Leu Gln Lys Tyr Leu Lys Lys Ser
65                  70                  75                  80

Glu Glu Asn Lys Ala Arg Asn Asp Lys Glu Arg Leu Asp Ser Tyr Tyr
                85                  90                  95

Lys Arg Asn Tyr Lys Asp Tyr Phe Glu Leu Phe Glu Gly Pro Ile Lys

```
                     100                 105                 110
Asp Lys Lys Glu Gly Leu Ser Glu Val Glu Lys Gly Ile Gln Glu Trp
            115                 120                 125

Leu Lys Ala Asn Lys
        130

<210> SEQ ID NO 66
<211> LENGTH: 130
<212> TYPE: PRT
<213> ORGANISM: Arabis alpina
<220> FEATURE:
<221> NAME/KEY: MISC_FEATURE
<222> LOCATION: (1)..(130)
<223> OTHER INFORMATION: PsaN

<400> SEQUENCE: 66

Met Ser Ser Ile Ser Gln Ser Ile Leu Met Ala Leu Thr Val Thr Val
1               5                   10                  15

Asn Lys Tyr Ala Ser Ser Asn Val Gln Ala Val Arg Arg Asn Asp Ser
            20                  25                  30

Lys Arg Asn Ser Leu Thr Ala Pro Asn Ala Asp Leu Gly Arg Arg Asn
        35                  40                  45

Ile Ile Leu Ser Ser Ser Ser Phe Leu Ala Ala Ala Leu Thr Thr
    50                  55                  60

Ser Asp Gln Leu Leu Gln Lys Tyr Leu Lys Lys Thr Glu Glu Asn Lys
65                  70                  75                  80

Ala Lys Asn Asp Lys Glu Arg Leu Asp Ser Phe Tyr Lys Arg Asn Tyr
                85                  90                  95

Lys Asp Tyr Phe Glu Phe Val Glu Gly Ser Leu Lys Gly Lys Thr Glu
            100                 105                 110

Ala Glu Leu Ser Glu Ser Glu Lys Lys Ile Leu Glu Trp Leu Lys Ala
        115                 120                 125

Asn Lys
    130

<210> SEQ ID NO 67
<211> LENGTH: 131
<212> TYPE: PRT
<213> ORGANISM: Medicago truncatula
<220> FEATURE:
<221> NAME/KEY: MISC_FEATURE
<222> LOCATION: (1)..(131)
<223> OTHER INFORMATION: PsaN

<400> SEQUENCE: 67

Met Ser Phe Ile Gly Gln Thr Met Leu Met Ala Leu Thr Val Thr Val
1               5                   10                  15

Asn Lys Tyr Thr Ser Ser Asn Val Gln Ala Val His Asn Arg Lys Gln
            20                  25                  30

Ala Asn Pro Thr Leu Arg Ser Thr Asn Met Glu Phe Gly Arg Arg Gly
        35                  40                  45

Leu Val Leu Ser Ile Val Ile Ala Ala Thr Ala Thr Gln Asp Pro Glu
    50                  55                  60

Ser Arg Thr Leu Leu Leu Gln Lys Tyr Leu Lys Lys Thr Gln Glu Asn
65                  70                  75                  80

Lys Glu Lys Asn Asp Lys Glu Arg Val Asp Ser Asn Tyr Lys Arg Asn
                85                  90                  95

Tyr Lys Asp Tyr Phe Glu Phe Ile Glu Gly Gly Leu Gln Ala Lys Glu
            100                 105                 110
```

```
Glu Gly Lys Leu Ser Glu Ala Glu Lys Gly Ile Leu Asp Trp Leu Lys
        115                 120                 125
Ala Asn Lys
    130

<210> SEQ ID NO 68
<211> LENGTH: 126
<212> TYPE: PRT
<213> ORGANISM: Cajanus cajan
<220> FEATURE:
<221> NAME/KEY: MISC_FEATURE
<222> LOCATION: (1)..(126)
<223> OTHER INFORMATION: PsaN

<400> SEQUENCE: 68

Met Ser Ser Ile Gly Gln Ser Ile Leu Met Ala Leu Thr Val Thr Val
1               5                   10                  15

Asn Lys Tyr Ala Ser Ser Asn Leu Gln Ala Val Gln Gly Lys Ala Pro
            20                  25                  30

Asn Lys Thr Thr Pro Thr Thr Leu Thr Thr Arg Arg Gly Leu Leu Leu
        35                  40                  45

Ser Ala Ala Ile Ala Thr Thr Gln Val Pro Asp Ser Arg Thr Gln Leu
    50                  55                  60

Leu Lys Lys Tyr Gln Lys Lys Ser Glu Glu Asn Lys Glu Lys Asn Asp
65                  70                  75                  80

Lys Glu Arg Leu Glu Ser Tyr Tyr Lys Arg Asn Tyr Lys Asp Tyr Phe
                85                  90                  95

Glu Leu Met Glu Gly Thr Leu Lys Arg Lys Glu Asp Gly Gln Leu Ser
            100                 105                 110

Asp Thr Glu Lys Gly Ile Leu Asp Trp Leu Gln Lys Asn Lys
        115                 120                 125

<210> SEQ ID NO 69
<211> LENGTH: 129
<212> TYPE: PRT
<213> ORGANISM: Cucumis sativus
<220> FEATURE:
<221> NAME/KEY: MISC_FEATURE
<222> LOCATION: (1)..(129)
<223> OTHER INFORMATION: PsaN

<400> SEQUENCE: 69

Met Ser Ser Ile Gly Gln Ser Ile Leu Met Ala Leu Ala Val Thr Leu
1               5                   10                  15

Asn Lys Phe Ala Ser Ser Asn Val Gln Ser Val Gln Arg Asn Lys Ala
            20                  25                  30

Thr Ala Thr Ala Thr Val Ser Ser Pro Ile Gly Arg Arg Ser Leu Leu
        35                  40                  45

Leu Ser Thr Leu Ala Pro Ala Ser Ala Ala Ala Ser Thr Val Asp
    50                  55                  60

Ser Arg Thr Glu Leu Leu Lys Arg Tyr Leu Lys Ser Glu Glu Asn
65                  70                  75                  80

Lys Glu Lys Asn Asp Lys Glu Arg Leu Glu Ser Tyr Tyr Lys Arg Asn
                85                  90                  95

Tyr Lys Asp Tyr Phe Glu Phe Val Glu Gly Ser Val Lys Asn Lys Asn
            100                 105                 110

Glu Leu Ser Glu Ala Glu Lys Gly Ile Val Glu Trp Leu Lys Arg Ser
        115                 120                 125
```

Lys

<210> SEQ ID NO 70
<211> LENGTH: 131
<212> TYPE: PRT
<213> ORGANISM: Prunus persica
<220> FEATURE:
<221> NAME/KEY: MISC_FEATURE
<222> LOCATION: (1)..(131)
<223> OTHER INFORMATION: PsaN

<400> SEQUENCE: 70

Met Ser Ser Ile Gly Gln Ser Ile Leu Met Ala Leu Thr Val Thr Val
1               5                   10                  15

Asn Lys Phe Ala Ser Ser Asn Val Gln Ala Val His Arg Arg Gln Arg
            20                  25                  30

Lys Asp Arg Arg Lys Thr Thr Ser Lys Ala Ala Asn Asp Phe Gly
        35                  40                  45

Arg Arg Gly Leu Leu Leu Ser Ala Ala Phe Ala Thr Pro Pro Val Ser
    50                  55                  60

Glu Ser Gly Ala Glu Leu Leu Lys Lys Tyr Leu Lys Lys Ser Glu Glu
65                  70                  75                  80

Asn Lys Ala Lys Asn Asp Lys Glu Arg Met Asp Ser Tyr Tyr Lys Arg
                85                  90                  95

Asn Tyr Lys Asp Tyr Phe Glu Phe Glu Glu Gly Thr Ile Arg Ala Lys
            100                 105                 110

Lys Gly Glu Leu Thr Lys Ser Glu Lys Gly Ile Leu Asp Trp Leu Glu
        115                 120                 125

Asn Asn Lys
        130

<210> SEQ ID NO 71
<211> LENGTH: 132
<212> TYPE: PRT
<213> ORGANISM: Lotus japonicus
<220> FEATURE:
<221> NAME/KEY: MISC_FEATURE
<222> LOCATION: (1)..(132)
<223> OTHER INFORMATION: PsaN

<400> SEQUENCE: 71

Met Ser Ser Val Gly Gln Ser Ile Leu Met Ala Leu Thr Val Thr Val
1               5                   10                  15

Asn Lys Tyr Ala Pro Ser Asn Leu Gln Ala Val His Arg Thr Gln Glu
            20                  25                  30

Lys Ala Gly Asn Gln Thr Thr Pro Thr Leu Ser Thr Asn Gly Glu Val
        35                  40                  45

Gly Arg Arg Gly Leu Ile Leu Ser Thr Ala Ile Ala Thr Thr Gln Val
    50                  55                  60

Pro Glu Ser Arg Thr Gln Leu Leu Lys Lys Tyr Gln Lys Lys Ser Glu
65                  70                  75                  80

Glu Asn Lys Glu Lys Asn Gly Lys Glu Arg Leu Asp Ser Tyr Tyr Lys
                85                  90                  95

Arg Asn Tyr Lys Asp Tyr Phe Glu Leu Met Glu Gly Thr Leu Lys Gly
            100                 105                 110

Lys Asp Gly Glu Leu Ser Glu Thr Glu Lys Gly Ile Arg Asp Trp Leu
        115                 120                 125

Gln Ser Asn Lys
        130

```
<210> SEQ ID NO 72
<211> LENGTH: 131
<212> TYPE: PRT
<213> ORGANISM: Pyrus x bretschneideri
<220> FEATURE:
<221> NAME/KEY: MISC_FEATURE
<222> LOCATION: (1)..(131)
<223> OTHER INFORMATION: PsaN

<400> SEQUENCE: 72

Met Ser Ser Ile Gly Gln Ser Ile Leu Met Ala Leu Thr Val Thr Val
1               5                   10                  15

Asn Lys Phe Ala Ser Ser Asn Val His Ala Val His Arg Lys Gln Lys
            20                  25                  30

Lys Ala Pro Lys Lys Ser Thr Ser Ala Thr Ser Thr Asn Asp Ile Gly
        35                  40                  45

Arg Arg Gly Leu Leu Leu Ser Ala Leu Val Ala Thr Pro Pro Leu Ser
50                  55                  60

Asp Ser Gly Ala Glu Leu Leu Lys Lys Tyr Leu Lys Lys Ser Glu Glu
65                  70                  75                  80

Asn Lys Ala Lys Asn Asp Lys Glu Arg Met Asp Ser Tyr Phe Lys Arg
                85                  90                  95

Asn Tyr Lys Glu Tyr Phe Glu Phe Glu Glu Gly Thr Ile Arg Ala Lys
            100                 105                 110

Lys Gly Glu Leu Thr Glu Ser Glu Lys Gly Ile Leu Asp Trp Leu Gln
        115                 120                 125

Asn Asn Lys
    130

<210> SEQ ID NO 73
<211> LENGTH: 128
<212> TYPE: PRT
<213> ORGANISM: Cucumis melo
<220> FEATURE:
<221> NAME/KEY: MISC_FEATURE
<222> LOCATION: (1)..(128)
<223> OTHER INFORMATION: PsaN

<400> SEQUENCE: 73

Met Ser Ser Ile Gly Gln Ser Ile Leu Met Ala Leu Ala Val Thr Leu
1               5                   10                  15

Asn Lys Phe Ala Ser Ser Asn Val Gln Ser Val Gln Arg Asn Lys Ala
            20                  25                  30

Thr Ala Thr Val Ser Ser Pro Ile Gly Arg Arg Asp Leu Leu Leu Ser
        35                  40                  45

Thr Val Ala Pro Ala Ser Thr Ala Ala Ala Ala Val Asp Ser
    50                  55                  60

Arg Thr Glu Leu Leu Lys Arg Tyr Leu Lys Lys Ser Glu Glu Asn Lys
65                  70                  75                  80

Glu Lys Asn Asp Lys Glu Arg Leu Glu Ser Tyr Tyr Lys Arg Asn Tyr
                85                  90                  95

Lys Asp Tyr Phe Glu Phe Val Glu Gly Ser Val Lys Asn Lys Asn Glu
            100                 105                 110

Leu Ser Glu Ala Glu Lys Gly Ile Val Glu Trp Leu Lys Arg Asn Lys
        115                 120                 125

<210> SEQ ID NO 74
<211> LENGTH: 119
```

```
<212> TYPE: PRT
<213> ORGANISM: Nicotiana sylvestris
<220> FEATURE:
<221> NAME/KEY: MISC_FEATURE
<222> LOCATION: (1)..(119)
<223> OTHER INFORMATION: PsaN

<400> SEQUENCE: 74

Met Ala Leu Thr Ala Gly Ser Asn Ala Tyr Ser Leu Ser Arg Phe Tyr
1               5                   10                  15

Val Gln Ala Ala Asp Thr Lys Glu Ile Lys Val Thr Thr Lys Lys Glu
            20                  25                  30

Thr Trp His Gly Arg Arg Glu Leu Ile Phe Ser Thr Val Ile Ala Ala
        35                  40                  45

Val Gln Val Asn Asp Ser Lys Thr Glu Leu Leu Gln Arg Tyr Leu Lys
    50                  55                  60

Lys Ser Glu Glu Asn Lys Ala Lys Asn Asp Lys Glu Arg Leu Asp Ser
65                  70                  75                  80

Tyr Tyr Lys Arg Asn Tyr Gly Asp Tyr Phe Gly Phe Leu Glu Gly Asp
                85                  90                  95

Leu Lys Gln Lys Lys Glu Gln Leu Thr Glu Ala Glu Gln Gly Ile Leu
            100                 105                 110

Lys Trp Leu Glu Thr Asn Lys
        115

<210> SEQ ID NO 75
<211> LENGTH: 131
<212> TYPE: PRT
<213> ORGANISM: Prunus mume
<220> FEATURE:
<221> NAME/KEY: MISC_FEATURE
<222> LOCATION: (1)..(131)
<223> OTHER INFORMATION: PsaN

<400> SEQUENCE: 75

Met Ser Ser Ile Gly Gln Ser Ile Leu Met Ala Leu Thr Val Thr Val
1               5                   10                  15

Asn Lys Phe Ala Ser Ser Asn Val Gln Ala Val His Arg Arg Gln Arg
            20                  25                  30

Lys Asp Arg Lys Lys Thr Ile Ser Ser Lys Ala Ala Asn Asp Phe Gly
        35                  40                  45

Arg Arg Gly Leu Leu Leu Ser Ala Ala Phe Ala Thr Pro Pro Val Ser
    50                  55                  60

Glu Ser Gly Ala Glu Leu Leu Lys Lys Tyr Leu Lys Lys Ser Glu Glu
65                  70                  75                  80

Asn Lys Ala Lys Asn Asp Lys Glu Arg Met Asp Ser Tyr Tyr Lys Arg
                85                  90                  95

Asn Tyr Lys Asp Tyr Phe Glu Phe Glu Gly Gly Thr Ile Arg Ala Lys
            100                 105                 110

Gln Gly Glu Leu Thr Lys Ser Glu Lys Gly Ile Leu Asp Trp Leu Glu
        115                 120                 125

Asn Asn Lys
    130

<210> SEQ ID NO 76
<211> LENGTH: 126
<212> TYPE: PRT
<213> ORGANISM: Morus notabilis
<220> FEATURE:
<221> NAME/KEY: MISC_FEATURE
```

<222> LOCATION: (1)..(126)
<223> OTHER INFORMATION: PsaN

<400> SEQUENCE: 76

Met Ser Ser Ile Gly Gln Ser Ile Leu Met Ala Leu Thr Val Thr Val
1               5                   10                  15

Asn Lys Tyr Ala Ser Ser Asn Val Gln Ala Val His Arg Lys Arg Lys
            20                  25                  30

Arg Pro Thr Thr Ala Thr Thr Thr Asp Ile Gly Arg Arg Gly Leu Phe
        35                  40                  45

Leu Ser Thr Val Val Ala Ala Leu Gln Val Ser Asp Ser Arg Thr Glu
    50                  55                  60

Leu Leu Lys Lys Tyr Leu Lys Ser Glu Glu Asn Lys Ala Lys Asn
65                  70                  75                  80

Asp Lys Glu Arg Leu Asn Ser Tyr Tyr Lys Arg Asn Tyr Lys Asp Tyr
                85                  90                  95

Phe Glu Leu Val Glu Gly Thr Leu Arg Gly Lys Glu Gly Leu Ser
            100                 105                 110

Glu Ala Glu Lys Gly Ile Arg Asp Trp Leu Gln Ser Asn Lys
        115                 120                 125

<210> SEQ ID NO 77
<211> LENGTH: 131
<212> TYPE: PRT
<213> ORGANISM: Fragaria vesca
<220> FEATURE:
<221> NAME/KEY: MISC_FEATURE
<222> LOCATION: (1)..(131)
<223> OTHER INFORMATION: PsaN

<400> SEQUENCE: 77

Met Ser Ser Ile Gly Gln Thr Ile Leu Met Ala Leu Thr Val Thr Val
1               5                   10                  15

Asn Lys Phe Ala Ser Ser Asn Val Gln Ala Val Gln Arg Lys Gln Arg
            20                  25                  30

Lys Gly Thr Lys Lys Thr Thr Pro Ser Gly Ala Thr Thr Asp Phe Gly
        35                  40                  45

Arg Arg Gly Leu Leu Leu Ser Ala Ala Val Ala Thr Pro Gln Leu Ser
    50                  55                  60

Asp Ser Ala Thr Glu Leu Leu Lys Lys Tyr Leu Lys Arg Ser Glu Asp
65                  70                  75                  80

Asn Lys Ala Lys Asn Asp Lys Gln Arg Met Asp Asp Tyr Tyr Lys Arg
                85                  90                  95

Asn Tyr Lys Asp Tyr Phe Gln Phe Glu Glu Gly Pro Leu Arg Ser Lys
            100                 105                 110

Lys Thr Pro Leu Thr Glu Ala Glu Lys Gly Ile Leu Asp Trp Leu Asp
        115                 120                 125

Ser Asn Lys
    130

<210> SEQ ID NO 78
<211> LENGTH: 119
<212> TYPE: PRT
<213> ORGANISM: Nicotiana tomentosiformis
<220> FEATURE:
<221> NAME/KEY: MISC_FEATURE
<222> LOCATION: (1)..(119)
<223> OTHER INFORMATION: PsaN

<400> SEQUENCE: 78

Met Ala Leu Thr Ala Gly Ser Ser Ala Tyr Ser Leu Ser Arg Phe Tyr
1               5                   10                  15

Val Gln Ala Ala Asp Thr Lys Glu Ile Lys Val Thr Thr Lys Lys Glu
            20                  25                  30

Thr Trp His Gly Arg Arg Glu Leu Leu Phe Ser Thr Val Ile Ala Ala
        35                  40                  45

Val Gln Val Asn Asp Ser Lys Thr Glu Leu Leu Lys Arg Tyr Leu Lys
    50                  55                  60

Lys Ser Glu Glu Asn Lys Ala Lys Asn Asp Lys Glu Arg Leu Asp Ser
65                  70                  75                  80

Tyr Tyr Lys Arg Asn Tyr Gly Asp Tyr Phe Gly Phe Leu Glu Gly Asp
                85                  90                  95

Leu Lys Gln Arg Lys Glu Gln Leu Thr Glu Ser Glu Gln Gly Ile Leu
            100                 105                 110

Lys Trp Leu Glu Ser Asn Lys
        115

<210> SEQ ID NO 79
<211> LENGTH: 136
<212> TYPE: PRT
<213> ORGANISM: Glycine max
<220> FEATURE:
<221> NAME/KEY: MISC_FEATURE
<222> LOCATION: (1)..(136)
<223> OTHER INFORMATION: PsaN

<400> SEQUENCE: 79

Met Ser Ser Ser Ile Gly Gln Ser Ile Leu Met Ala Leu Thr Val Thr
1               5                   10                  15

Val Asn Lys Tyr Ala Ser Ser Asn Leu Gln Ala Val Pro Arg Thr Gln
            20                  25                  30

Gly Lys Val Ala Thr Lys Lys Thr Thr Pro Thr Leu Ser Thr Asn Val
        35                  40                  45

Glu Met Gly Arg Arg Gly Leu Val Leu Ser Thr Val Ile Ala Thr Thr
    50                  55                  60

Gln Val Pro Glu Pro Asp Ser Arg Thr Gln Leu Leu Lys Lys Tyr Gln
65                  70                  75                  80

Lys Lys Ser Glu Glu Asn Lys Glu Lys Asn Asp Lys Glu Arg Leu Glu
                85                  90                  95

Ser Tyr Tyr Lys Arg Asn Tyr Lys Asp Tyr Phe Glu Leu Met Glu Gly
            100                 105                 110

Thr Leu Lys Ala Lys Asp Gly Lys Leu Ser Asp Thr Glu Lys Gly Ile
        115                 120                 125

Leu Asp Trp Leu Gln Lys Asn Lys
    130                 135

<210> SEQ ID NO 80
<211> LENGTH: 131
<212> TYPE: PRT
<213> ORGANISM: Ziziphus jujuba
<220> FEATURE:
<221> NAME/KEY: MISC_FEATURE
<222> LOCATION: (1)..(131)
<223> OTHER INFORMATION: PsaN

<400> SEQUENCE: 80

Met Ser Ser Ile Gly Gln Ser Ile Leu Met Ala Leu Thr Val Thr Val
1               5                   10                  15

```
Asn Lys Phe Ala Ser Ser Asn Val His Ala Val His Arg Arg Gln Thr
            20                  25                  30

His Pro Pro Asn Ser Thr Ser Thr Thr Asp Ala Asn Gly Arg Arg
        35                  40                  45

Gly Leu Leu Leu Ser Thr Leu Leu Ala Ala Ser Gln Leu Thr Glu Asp
50                  55                  60

Asp Ser Arg Thr Gln Leu Leu Lys Lys Tyr Leu Lys Lys Ser Glu Glu
65                  70                  75                  80

Asn Lys Ala Lys Asn Asp Lys Glu Arg Leu Asp Ser Tyr Tyr Lys Arg
                85                  90                  95

Asn Tyr Lys Asp Tyr Phe Glu Phe Glu Glu Gly Ala Leu Arg Ala Lys
            100                 105                 110

Arg Gly Glu Leu Ser Glu Ser Glu Lys Gly Ile Leu Asp Trp Leu Gln
        115                 120                 125

Thr Asn Arg
    130
```

<210> SEQ ID NO 81
<211> LENGTH: 278
<212> TYPE: PRT
<213> ORGANISM: Gossypium raimondii
<220> FEATURE:
<221> NAME/KEY: MISC_FEATURE
<222> LOCATION: (1)..(278)
<223> OTHER INFORMATION: PsaN
<220> FEATURE:
<221> NAME/KEY: MISC_FEATURE
<222> LOCATION: (46)..(136)
<223> OTHER INFORMATION: PsaN

<400> SEQUENCE: 81

```
Met Gly Ser Ile Ala Gln Ser Val Leu Met Ala Leu Thr Val Thr Val
1               5                   10                  15

Asn Gln Phe Ala Ser Ser Asn Val Leu Ala Val His Arg Lys Gln Gly
            20                  25                  30

Lys Ser Pro Ser Pro Thr Ser Lys Pro Lys Pro Thr Asn Thr Lys Thr
        35                  40                  45

Ile Thr Ala Ala Ala Ala Asn Ala Gly Asp Thr Gly Ile Ala Arg Arg
    50                  55                  60

Gly Leu Ile Leu Tyr Ala Val Ala Ser Ala Pro Gln Leu Asn Asp Ser
65                  70                  75                  80

Arg Thr Glu Leu Leu Lys Asn Tyr Leu Lys Lys Thr Glu Glu Asn Lys
                85                  90                  95

Ala Lys Asn Asp Lys Glu Arg Met Glu Asn Tyr Tyr Arg Arg Asn Tyr
            100                 105                 110

Lys Asp Tyr Phe Glu Phe Val Glu Gly Thr Leu Lys Gly Lys Asp Glu
        115                 120                 125

Gln Gln Leu Ser Glu Ala Glu Lys Ala Ser Lys Arg Val Pro Lys Ser
    130                 135                 140

Glu Glu Ser Ser Ser Pro Phe Lys Glu Leu Arg Thr Val Ala Cys Ala
145                 150                 155                 160

Leu Leu Ala Val Cys Thr Val Ala Thr Ala Ser Pro Val Ile Ala Ala
                165                 170                 175

Asn Gln Arg Leu Pro Pro Leu Ser Thr Glu Pro Asn Arg Cys Glu Arg
            180                 185                 190

Ala Phe Val Gly Asn Thr Ile Gly Gln Ala Asn Gly Val Tyr Asp Lys
        195                 200                 205
```

```
Pro Leu Asp Leu Arg Phe Cys Asp Tyr Thr Asn Glu Lys Ser Asn Leu
    210                 215                 220

Lys Gly Lys Ser Leu Ala Ala Ala Leu Met Ser Asp Ala Lys Phe Asp
225                 230                 235                 240

Gly Ala Asp Met Ser Glu Ala Val Met Ser Lys Ala Tyr Ala Val Gly
                245                 250                 255

Ala Ser Phe Lys Gly Lys Ser Ser Leu Cys Phe Ala Phe Ser Ala Ile
            260                 265                 270

Ile His Leu Ile Val Thr
        275

<210> SEQ ID NO 82
<211> LENGTH: 332
<212> TYPE: PRT
<213> ORGANISM: Gossypium raimondii
<220> FEATURE:
<221> NAME/KEY: MISC_FEATURE
<222> LOCATION: (1)..(332)
<223> OTHER INFORMATION: PsaN
<220> FEATURE:
<221> NAME/KEY: MISC_FEATURE
<222> LOCATION: (46)..(136)
<223> OTHER INFORMATION: PsaN

<400> SEQUENCE: 82

Met Gly Ser Ile Ala Gln Ser Val Leu Met Ala Leu Thr Val Thr Val
1               5                   10                  15

Asn Gln Phe Ala Ser Ser Asn Val Leu Ala Val His Arg Lys Gln Gly
                20                  25                  30

Lys Ser Pro Ser Pro Thr Ser Lys Pro Lys Pro Thr Asn Thr Lys Thr
            35                  40                  45

Ile Thr Ala Ala Ala Asn Ala Gly Asp Thr Gly Ile Ala Arg Arg
        50                  55                  60

Gly Leu Ile Leu Tyr Ala Val Ala Ser Ala Pro Gln Leu Asn Asp Ser
65                  70                  75                  80

Arg Thr Glu Leu Leu Lys Asn Tyr Leu Lys Lys Thr Glu Glu Asn Lys
                85                  90                  95

Ala Lys Asn Asp Lys Glu Arg Met Glu Asn Tyr Tyr Arg Arg Asn Tyr
            100                 105                 110

Lys Asp Tyr Phe Glu Phe Val Glu Gly Thr Leu Lys Gly Lys Asp Glu
        115                 120                 125

Gln Gln Leu Ser Glu Ala Glu Lys Ala Ser Lys Arg Val Pro Lys Ser
130                 135                 140

Glu Glu Ser Ser Ser Pro Phe Lys Glu Leu Arg Thr Val Ala Cys Ala
145                 150                 155                 160

Leu Leu Ala Val Cys Thr Val Thr Ala Ser Pro Val Ile Ala Ala
                165                 170                 175

Asn Gln Arg Leu Pro Pro Leu Ser Thr Glu Pro Asn Arg Cys Glu Arg
            180                 185                 190

Ala Phe Val Gly Asn Thr Ile Gly Gln Ala Asn Gly Val Tyr Asp Lys
        195                 200                 205

Pro Leu Asp Leu Arg Phe Cys Asp Tyr Thr Asn Glu Lys Ser Asn Leu
    210                 215                 220

Lys Gly Lys Ser Leu Ala Ala Ala Leu Met Ser Asp Ala Lys Phe Asp
225                 230                 235                 240

Gly Ala Asp Met Ser Glu Ala Val Met Ser Lys Ala Tyr Ala Val Gly
                245                 250                 255
```

```
Ala Ser Phe Lys Asp Phe Ser Asn Ala Val Leu Asp Arg Val Asn Phe
            260                 265                 270

Gly Lys Ala Asn Leu Gln Gly Ala Ile Phe Lys Asn Thr Val Leu Ser
            275                 280                 285

Gly Ser Thr Phe Asp Asn Ala Gln Leu Glu Asp Ala Val Phe Glu Asp
            290                 295                 300

Thr Ile Ile Gly Tyr Ile Asp Leu Gln Lys Leu Cys Thr Asn Thr Ser
305                 310                 315                 320

Ile Ser Ala Glu Gly Arg Val Glu Leu Gly Cys Arg
            325                 330

<210> SEQ ID NO 83
<211> LENGTH: 149
<212> TYPE: PRT
<213> ORGANISM: Picea sitchensis
<220> FEATURE:
<221> NAME/KEY: MISC_FEATURE
<222> LOCATION: (1)..(149)
<223> OTHER INFORMATION: PsaN

<400> SEQUENCE: 83

Met Ala Pro Ser Phe Ala Met Val Leu Pro Ser Ser Ile Ser Val Cys
1               5                   10                  15

Cys Ile Asn Asn His Asn Cys Lys Arg Glu Ile Ala Cys His His Pro
            20                  25                  30

Ser Pro Ile Ser Val Lys Pro Glu Pro Thr Tyr Phe Cys Lys Ser Thr
        35                  40                  45

Ser Ser Ser Leu His Cys Arg Arg Lys Val Leu Gln Ser Thr Ile Leu
    50                  55                  60

Ser Ala Leu Leu Leu Gln Pro Val Leu Ser Pro Asn Trp Val Ala Ala
65                  70                  75                  80

Glu Glu Glu Asn Ser Arg Lys Asn Asp Leu Ile Glu Arg Leu Leu Gln
                85                  90                  95

Lys Ser Lys Ala Asn Lys Ala Lys Tyr Ala Lys Glu Arg Leu Asp Asp
            100                 105                 110

Tyr Tyr Lys Arg Asn Tyr Lys Asp Tyr Phe Glu Phe Val Glu Gly Ser
        115                 120                 125

Val Lys Gln Gly Glu Leu Ser Glu Ala Glu Lys Gly Ile Leu Glu Trp
    130                 135                 140

Leu Arg Lys Asn Arg
145

<210> SEQ ID NO 84
<211> LENGTH: 153
<212> TYPE: PRT
<213> ORGANISM: Physcomitrella patens
<220> FEATURE:
<221> NAME/KEY: MISC_FEATURE
<222> LOCATION: (1)..(153)
<223> OTHER INFORMATION: PsaN

<400> SEQUENCE: 84

Met Ala Ser Leu Gly Gly Gln Leu Cys Ser Gly Ile His Ser Leu Ser
1               5                   10                  15

Cys Gln Gly Arg Ala Asn Thr Lys Leu His Pro Ile Val Val Lys Ser
            20                  25                  30

Arg Lys Cys Glu Val Ala Arg Ala Ser Tyr Asp Ala Gln Val Gln Thr
        35                  40                  45

Ser Arg Arg Glu Ala Ile Thr Arg Leu Ala Ile Ala Ser Gly Ala Ala
```

```
                50                  55                  60
Leu Leu Ser Leu Val Ala Ala Thr Asp Ala Ala His Ala Ala Ala Gly
 65                  70                  75                  80

Glu Ile Glu Thr Ala Glu Ala Ala Ser Asn Pro Leu Ile Gln Lys
                 85                  90                  95

Leu Leu Glu Thr Ser Arg Ala Asn Lys Ala Val Asn Asp Ala Ala Arg
                100                 105                 110

Leu Glu Asp Tyr Tyr Arg Arg Asn Phe Thr Tyr Phe Gln Phe Val
                115                 120                 125

Glu Gly Ser Val Arg Asn Lys Lys Glu Leu Thr Pro Ala Glu Lys Ala
                130                 135                 140

Ile Val Glu Trp Leu Ala Lys Asn Lys
145                 150

<210> SEQ ID NO 85
<211> LENGTH: 167
<212> TYPE: PRT
<213> ORGANISM: Klebsormidium flaccidum
<220> FEATURE:
<221> NAME/KEY: MISC_FEATURE
<222> LOCATION: (1)..(167)
<223> OTHER INFORMATION: PsaN

<400> SEQUENCE: 85

Met Leu Thr Leu Ser Gly Arg Thr Ser Asp Gly Val Arg Ala Arg Gln
  1               5                  10                  15

Cys Asn Ser Val Phe Gly Arg Gln Thr Arg Arg Ile Val Trp Gly Gln
                 20                  25                  30

His Arg Ala Glu Arg Ser Arg Glu Ala Pro Pro Arg Cys Leu Ser Ser
                 35                  40                  45

Glu Ser Pro Glu Tyr Lys Leu Gln Lys Val Glu Ile Asn Ala Pro Ala
                 50                  55                  60

Arg Arg Thr Ala Leu Leu Leu Ala Gly Ala Ala Phe Phe Ser Ser Leu
 65                  70                  75                  80

Thr Ala Leu Val Ala Asp Gln Ser Thr Ala His Ala Ala Pro Val Lys
                 85                  90                  95

Pro Pro Ala Val Glu Glu Val Pro Glu Ile Val Lys Glu Met Leu Glu
                100                 105                 110

Arg Ser Lys Leu Asn Lys Ala Lys Tyr Asp Lys Glu Arg Leu Asp Asp
                115                 120                 125

Tyr Asn Arg Arg Asn Phe Ser Asp Tyr Phe Glu Phe Thr Thr Gly Ser
                130                 135                 140

Lys Asn Pro Lys Lys Met Thr Glu Thr Asp Lys Ala Met Leu Lys Trp
145                 150                 155                 160

Leu Glu Ala Asn Arg Lys Lys
                165

<210> SEQ ID NO 86
<211> LENGTH: 146
<212> TYPE: PRT
<213> ORGANISM: Chlamydomonas reinhardtii
<220> FEATURE:
<221> NAME/KEY: MISC_FEATURE
<222> LOCATION: (1)..(146)
<223> OTHER INFORMATION: PsaN

<400> SEQUENCE: 86

Met Ser Ser Met Leu His His Arg Gln Ala Ser Thr Ser Val Val Gln
  1               5                  10                  15
```

Arg Gly Gln Ser Arg Arg Ala Val Ala Pro Met Cys Thr Leu Arg
            20                  25                  30

Val Asn Glu Pro Val Pro Val Gln Gln Arg Leu Leu Ser Ala Gly Ile
         35                  40                  45

Ala Ala Ala Thr Ser Leu Val Leu Leu Ala Ser Phe Pro Leu Ala Ser
     50                  55                  60

Ser Ala Ala Arg Leu Glu Leu Pro Asn Lys Glu Val Asp Asp Ala Thr
65                  70                  75                  80

Ser Pro Phe Val Gln Glu Leu Leu Lys Arg Ser Asn Glu Asn Arg Glu
                 85                  90                  95

Arg Tyr Gln Lys Glu Arg Leu Gln Asp Tyr Tyr Arg Arg Asn Phe Lys
            100                 105                 110

Glu Tyr Phe Glu Phe Glu Gly Ser Thr Ala Lys Val Gly Lys Ala Arg
        115                 120                 125

Gly Leu Ser Pro Glu Thr Gln Gln Ala Ile Ala Lys Trp Leu Glu Glu
    130                 135                 140

Asn Lys
145

<210> SEQ ID NO 87
<211> LENGTH: 126
<212> TYPE: PRT
<213> ORGANISM: Gonium pectorale
<220> FEATURE:
<221> NAME/KEY: MISC_FEATURE
<222> LOCATION: (1)..(126)
<223> OTHER INFORMATION: PsaN

<400> SEQUENCE: 87

Met Ala Pro Ile Val Pro Val Ser Asp Asp Ala Arg Ser Ser Pro
1               5                   10                  15

Glu Ala Lys Arg Arg Pro Pro Ala Leu Leu Phe Ala Gly Leu Ala Val
            20                  25                  30

Ala Ser Ser Phe Ala Leu Leu Ala Ser Ala Gly Pro Ala Met Ala Arg
         35                  40                  45

Leu Glu Leu Pro Asn Lys Glu Val Asp Asn Asp Thr Ser Pro Leu Val
     50                  55                  60

Gln Lys Leu Leu Gln Arg Thr Ala Glu Asn Lys Asp Arg Tyr Ala Lys
65                  70                  75                  80

Glu Arg Leu Gln Asp Tyr Tyr Lys Arg Asn Phe Lys Glu Tyr Phe Glu
                 85                  90                  95

Phe Glu Ala Ser Asn Ala Lys Val Ala Lys Ala Arg Gly Leu Ser Pro
            100                 105                 110

Glu Ser Ala Ala Ala Ile Gln Lys Trp Leu Glu Glu Asn Lys
        115                 120                 125

<210> SEQ ID NO 88
<211> LENGTH: 161
<212> TYPE: PRT
<213> ORGANISM: Fragaria vesca
<220> FEATURE:
<221> NAME/KEY: MISC_FEATURE
<222> LOCATION: (1)..(161)
<223> OTHER INFORMATION: PsaN

<400> SEQUENCE: 88

Met Ala Ala Met Asn Ser Ser Val Leu Ala Ser Asn Tyr Ala Ile Ser
1               5                   10                  15

Gly Ser Ser Ala Ile Leu Ala Glu Gly Asn Gly Lys Met Thr Ser Met
            20                  25                  30

Pro Gln Arg Val Ala Met Pro Val Ile Arg Ala Gln His Gln Glu Ser
        35                  40                  45

Gln Ser Val Gly Gly Arg Arg Ala Ala Leu Leu Phe Leu Thr Ala Thr
    50                  55                  60

Ala Ala Ala Val Ala Ser Asn Ser Ile Ala Asn Ala Gly Val Ile Asp
65                  70                  75                  80

Asp Tyr Leu Glu Lys Ser Lys Thr Asn Lys Glu Leu Asn Asp Lys Lys
                85                  90                  95

Arg Leu Ala Thr Ser Gly Ala Asn Phe Ala Arg Ala Phe Thr Val Gln
            100                 105                 110

Phe Gly Thr Cys Lys Phe Pro Glu Asn Phe Thr Gly Cys Gln Asp Leu
        115                 120                 125

Ala Lys Gln Lys Lys Val Pro Phe Leu Ser Asp Asp Leu Ser Leu Glu
    130                 135                 140

Cys Glu Gly Lys Asp Lys Tyr Lys Cys Gly Ser Asn Val Phe Trp Lys
145                 150                 155                 160

Trp

<210> SEQ ID NO 89
<211> LENGTH: 974
<212> TYPE: DNA
<213> ORGANISM: Zea mays
<220> FEATURE:
<221> NAME/KEY: promoter
<222> LOCATION: (1)..(974)
<223> OTHER INFORMATION: RbcS_Promoter+5'UTR

<400> SEQUENCE: 89
gagctccctt taatctggcg ctagatctgc atccgcggct tgcaaagata aatggcacat    60
ttagtgtgtt attttgcaat acctttcata gtagatatcc ttaaatgcag ttttaggcat   120
gtttgggtaa ttaaataaca ttttttaggag gagttttaga tttacctttc tttcgtgatg   180
actgatgaca gacgtgggga attcaaatgc aactctagcg aaagttcata tattttcat    240 aaatagctga ggctggggta attattttt ttgtagaaaa atagaatagg tggaatggtt   300
ggggaaggcg taggcgctcg tggacgacgc ccgataaaag acaagaggcg gaattgccat   360
gaattcgagg tagctaagta aggcgcatat atatgccaaa aaattctact gtcacttttcc   420 aatttcaatg cgctgccaaa caagccatcc tggaaactga cttgaattca gcccaattct   480
gtagatccaa acagggccgg cgtcagtgcc tcaggtgaga gagcagcaga cgatgcaaag   540
agccaaaact gcaagcagac gcagccgaag ccgaagccga agcccaagcc caaaactgtt   600
ttgtctttgc ccagaaccgc gacgagccta aactgcgctt cctcctatct acaagtccct   660
ggcacatcac gcatagtcca accatggcgc gcaggcgata aggcgcgcca cggggacgcg   720
acatgtggtg gcgacgcga tcaggatagg gccaggctgg ccgggcgcgg ccacgggaga   780
acggtggcca ctcgtcccac atccgcttcg tcctgtcctg tactgcgtcc tgccccaac    840 gagagccgga gccggccatc ccgtcgcaca ctctccccct ctatatatgc cgtcggtgtg   900
ggggagccta ctacaggacg acccaagcaa gcaagcaagc agcgagtaca tacatactag   960
gcagccaggc agcc                                                    974

<210> SEQ ID NO 90
<211> LENGTH: 439
<212> TYPE: DNA

```
<213> ORGANISM: Zea mays
<220> FEATURE:
<221> NAME/KEY: 3'UTR
<222> LOCATION: (1)..(439)
<223> OTHER INFORMATION: RbcS_3'UTR

<400> SEQUENCE: 90
accgcgcccg ccggccgccc cccgccggct agctagctag ctagctcctg cgtgagctag      60
tagctagtgc catgcgtcgt ctctgtcgtt cggttttgct tcgggtcacc gtgtacccctt    120 tgcttgcttg gtttcttctt tccttttttc cttttttttt cttcttttcc ccggccatgg    180
ttcctttgct ttccagcagt tctctgctgg atgtgatgta tccattgttg caatcatggc    240
cttgcattgg ctacctctat acctgctaca aaactactgc aacgcctata tatacttggg    300
gtgaggaaca tgtgaatgca agctccggct atcatataca tgtaatatgg atacaaacta    360
tatatataaa tccgccgagg cgccgacaat actatacgac accgtgttaa gttaatatat    420
aactggtgct ttttattta                                                  439

<210> SEQ ID NO 91
<211> LENGTH: 1647
<212> TYPE: DNA
<213> ORGANISM: Pisum sativum and Synechococcus sp. PCC 7942
<220> FEATURE:
<221> NAME/KEY: misc_feature
<222> LOCATION: (1)..(1647)
<223> OTHER INFORMATION: RbcS_signal_peptide-ictB
<220> FEATURE:
<221> NAME/KEY: sig_peptide
<222> LOCATION: (1)..(243)
<223> OTHER INFORMATION: RbcS_signal_peptide
<220> FEATURE:
<221> NAME/KEY: misc_feature
<222> LOCATION: (244)..(1647)
<223> OTHER INFORMATION: ictB

<400> SEQUENCE: 91
atggcttcta tgatttcttc ttctgctgtg acaacagtgt ctagggcttc tagggggccag     60 tctgctgctg tggctccttt cggcggcctc aagtctatga caggcttccc tgtgaagaag    120
gtgaatacag atattacatc tattacatct aatggcggca gggtgaagtg catgcaggtg    180
tggcctccta ttggcaagaa gaagttcgag acactctctt acctccctcc tctcacaagg    240
gatatgacag tgtggcagac actcacattc gctcattacc agcctcagca gtggggccat    300
tcttctttcc tccataggct cttcggctct ctcagggctt ggagggcttc ttctcagctc    360
ctcgtgtggt ctgaggctct cggcggcttc ctcctgctg tggtgtacgg ctctgctcct     420
ttcgtgcctt cttctgctct cggcctcggc ctcgctgcta ttgctgctta ctgggctctc    480
ctctctctca cagatattga tctcaggcag gctacaccta tcattggct cgtgctcctc     540 tactggggcg tggatgctct cgctacaggc ctctctcctg tgagggctgc tgctctcgtg    600
ggcctcgcta agctcacact ctacctcctc gtgttcgctc tcgctgctag ggtgctcagg    660
aatcctaggc tcaggtctct cctcttctct gtggtggtga ttacatctct cttcgtgtct    720
gtgtacggcc tcaatcagtg gatttacggc gtggaggagc tcgctacatg ggtggatagg    780
aattctgtgg ctgatttcac atctaggtg tactcttacc tcgcaatcc taatctcctc      840 gctgcttacc tcgtgcctac aacagctttc tctgctgctg ctattggcgt gtggaggggc    900
tggctcccta agctcctcgc tattgctgct acaggcgctt cttctctctg cctcattctc    960
acatactcta ggggcggctg gctcggcttc gtggctatga ttttcgtgtg ggctctcctc   1020
ggcctctact ggttccagcc taggctccct gctccttgga ggaggtggct cttccctgtg   1080
```

```
gtgctcggcg gcctcgtggc tgtgctcctc gtggctgtgc tcggcctcga gcctctcagg    1140
gtgagggtgc tctctatttt cgtgggcagg gaggattctt ctaataattt caggattaat    1200
gtgtggctcg ctgtgctcca gatgattcag gataggcctt ggctcggcat tggccctggc    1260
aatacagctt tcaatctcgt gtaccctctc taccagcagg ctaggttcac agctctctct    1320
gcttactctg tgcctctcga ggtggctgtg gagggcggcc tcctcggcct cacagctttc    1380
gcttggctcc tcctcgtgac agctgtgaca gctgtgcgcc aggtgtctag gctcaggagg    1440
gataggaatc ctcaggcttt ctggctcatg gcttctctcg ctggcctcgc tggcatgctc    1500
ggccatggcc tcttcgatac agtgctctac aggcctgagg cttctacact ctggtggctc    1560
tgcattggcg ctattgcttc tttctggcag cctcagcctt ctaagcagct ccctcctgag    1620
gctgagcatt ctgatgagaa gatgtga                                        1647
```

<210> SEQ ID NO 92
<211> LENGTH: 548
<212> TYPE: PRT
<213> ORGANISM: Pisum sativum and Synechococcus sp. PCC 7942
<220> FEATURE:
<221> NAME/KEY: MISC_FEATURE
<222> LOCATION: (1)..(548)
<223> OTHER INFORMATION: RbcS_signal_peptide-ictB
<220> FEATURE:
<221> NAME/KEY: MISC_FEATURE
<222> LOCATION: (1)..(81)
<223> OTHER INFORMATION: RbcS_signal_peptide
<220> FEATURE:
<221> NAME/KEY: MISC_FEATURE
<222> LOCATION: (82)..(548)
<223> OTHER INFORMATION: ictB

<400> SEQUENCE: 92

```
Met Ala Ser Met Ile Ser Ser Ala Val Thr Thr Val Ser Arg Ala
1               5                   10                  15

Ser Arg Gly Gln Ser Ala Ala Val Ala Pro Phe Gly Gly Leu Lys Ser
            20                  25                  30

Met Thr Gly Phe Pro Val Lys Lys Val Asn Thr Asp Ile Thr Ser Ile
        35                  40                  45

Thr Ser Asn Gly Gly Arg Val Lys Cys Met Gln Val Trp Pro Pro Ile
    50                  55                  60

Gly Lys Lys Lys Phe Glu Thr Leu Ser Tyr Leu Pro Pro Leu Thr Arg
65                  70                  75                  80

Asp Met Thr Val Trp Gln Thr Leu Thr Phe Ala His Tyr Gln Pro Gln
                85                  90                  95

Gln Trp Gly His Ser Ser Phe Leu His Arg Leu Phe Gly Ser Leu Arg
            100                 105                 110

Ala Trp Arg Ala Ser Ser Gln Leu Leu Val Trp Ser Glu Ala Leu Gly
        115                 120                 125

Gly Phe Leu Leu Ala Val Val Tyr Gly Ser Ala Pro Phe Val Pro Ser
    130                 135                 140

Ser Ala Leu Gly Leu Gly Leu Ala Ala Ile Ala Ala Tyr Trp Ala Leu
145                 150                 155                 160

Leu Ser Leu Thr Asp Ile Asp Leu Arg Gln Ala Thr Pro Ile His Trp
                165                 170                 175

Leu Val Leu Leu Tyr Trp Gly Val Asp Ala Leu Ala Thr Gly Leu Ser
            180                 185                 190

Pro Val Arg Ala Ala Ala Leu Val Gly Leu Ala Lys Leu Thr Leu Tyr
        195                 200                 205
```

```
Leu Leu Val Phe Ala Leu Ala Ala Arg Val Leu Arg Asn Pro Arg Leu
    210                 215                 220

Arg Ser Leu Leu Phe Ser Val Val Ile Thr Ser Leu Phe Val Ser
225                 230                 235                 240

Val Tyr Gly Leu Asn Gln Trp Ile Tyr Gly Val Glu Glu Leu Ala Thr
                245                 250                 255

Trp Val Asp Arg Asn Ser Val Ala Asp Phe Thr Ser Arg Val Tyr Ser
                260                 265                 270

Tyr Leu Gly Asn Pro Asn Leu Leu Ala Ala Tyr Leu Val Pro Thr Thr
                275                 280                 285

Ala Phe Ser Ala Ala Ala Ile Gly Val Trp Arg Gly Trp Leu Pro Lys
                290                 295                 300

Leu Leu Ala Ile Ala Ala Thr Gly Ala Ser Ser Leu Cys Leu Ile Leu
305                 310                 315                 320

Thr Tyr Ser Arg Gly Gly Trp Leu Gly Phe Val Ala Met Ile Phe Val
                325                 330                 335

Trp Ala Leu Leu Gly Leu Tyr Trp Phe Gln Pro Arg Leu Pro Ala Pro
                340                 345                 350

Trp Arg Arg Trp Leu Phe Pro Val Val Leu Gly Leu Val Ala Val
                355                 360                 365

Leu Leu Val Ala Val Leu Gly Leu Glu Pro Leu Arg Val Arg Val Leu
370                 375                 380

Ser Ile Phe Val Gly Arg Glu Asp Ser Ser Asn Asn Phe Arg Ile Asn
385                 390                 395                 400

Val Trp Leu Ala Val Leu Gln Met Ile Gln Asp Arg Pro Trp Leu Gly
                405                 410                 415

Ile Gly Pro Gly Asn Thr Ala Phe Asn Leu Val Tyr Pro Leu Tyr Gln
                420                 425                 430

Gln Ala Arg Phe Thr Ala Leu Ser Ala Tyr Ser Val Pro Leu Glu Val
                435                 440                 445

Ala Val Glu Gly Gly Leu Leu Gly Leu Thr Ala Phe Ala Trp Leu Leu
                450                 455                 460

Leu Val Thr Ala Val Thr Ala Val Arg Gln Val Ser Arg Leu Arg Arg
465                 470                 475                 480

Asp Arg Asn Pro Gln Ala Phe Trp Leu Met Ala Ser Leu Ala Gly Leu
                485                 490                 495

Ala Gly Met Leu Gly His Gly Leu Phe Asp Thr Val Leu Tyr Arg Pro
                500                 505                 510

Glu Ala Ser Thr Leu Trp Trp Leu Cys Ile Gly Ala Ile Ala Ser Phe
                515                 520                 525

Trp Gln Pro Gln Pro Ser Lys Gln Leu Pro Pro Glu Ala Glu His Ser
                530                 535                 540

Asp Glu Lys Met
545

<210> SEQ ID NO 93
<211> LENGTH: 1814
<212> TYPE: DNA
<213> ORGANISM: Zea mays
<220> FEATURE:
<221> NAME/KEY: promoter
<222> LOCATION: (1)..(1814)
<223> OTHER INFORMATION: ZmCA1 5'mod

<400> SEQUENCE: 93
```

```
ccccgcccat gtcagcaggc ctccgaggct tttggttgcc caaccagccc atgggctgaa      60
ttcataacag tgttggcaca cagtttcctc ttcactcgga agcttattat tatcgatcct     120
gaaccagaga ctagcagagc tagcatttcg acgacgcgtc tcaactctca acctccaagt     180
ccacctcgtg tacgtgctgc cttgccagtt gccactgggc actgctggcc cagtgaccaa     240
ccatgcgtta gatctgacag caccaccgaa ccatcctccc cggtgatcaa caaacgacgg     300
cagccacatc ttgcacccaa cgtgatgatg aatgatgcct agaacttttg acaacaaaac     360
gcagcacagg tagcaggttt aattcaacaa gactttctac tatatagagc cacaccatag     420
agataactaa tctgtgcgca aagccaaagt gctgacggca actgtggtgc agcctttttca    480 tctccgtttt taagttttttt gcccctcctt ttgttttctg tttttctggg aactctttaa     540
accgccgtgg cgccgtgtaa actttgctgt agccttttcg cgtgcaatgg cagagcgccc     600 tgttctttc ctgctaaaga aaaaaaaaa ggagcacctg atcgctggca ggcccacggc      660
ccacccaact gtgtctgtaa cgctcggcgt ccctgcattg catgccaagt gccaaccacc     720
agtccatagc agggtcaggg agaccgcaga tgaggccggg gcaacggtga tgccgcaaag     780
aggattcaga atccttttc ttttcttttc ttttaccacc gggctggcat cacagattac      840
acgcgcagta gagtaagcac gtctctctcg tagccaagaa caacagtcta cacagctcgc     900
tttctccgcc cttgtctggg cgttacggca ggcaagcccc ctcgtttttct tctgctcgcg    960 ttctccttcc atgtccacat ctcctgtgcc accgcacgca aggtgccaac gctccctcgc     1020
cgcagtagca tcgcgtccac acaaactgca cctccactag atacggcggt gatccggcga    1080
gagagcgcga cacgcacagg ccagctagcg tttctccgac gccgcgcgtt tcatcatttc    1140
ccgcttcccc tgcccccggc cgcgcgcgcg cgcccgtgtg gtccagacca ggacgcgcgc    1200
ggatgtgcat ccggcgcgcg cccgtcggcc acacggtgcc gccgcgcgtt atcccgagcc    1260
ctgtcctgtc ctgtcctgtt ccatctcgcg cgcgaggggg ggaggggagg gcagcgagtg    1320
gcgcgctggc ggatgaggcg ccgagtggcc cgcatccacc ggcgcaggcg agccgcacga    1380
cgccgccgcg ctcgcggaac gccgccgcca cacatgcgca cccccggccc gcggggctgt    1440
aacggccttg tcgccacgcg tgcgcccccgt gtgtataagg aggcagcgcg tacagggggc    1500
gacaacgata agcggcactc gcacgatcaa tctacacatt gcccgtccgc gccaccacat    1560
ccagcatcgt cgccagcctc gccaccccg cgccgtcctc ctcctccggc tccggctccg     1620 gccgcccag gccaggctc atccggaacg ccccgtctt cgccgcccc gccaccgtcg       1680 tgtaaacggg acggcgggca gctgaggagt caaacgagag agatcgagag aaagaaaggg    1740
agggcatcca ccagccgccg gcgataagag gggaggagag agaggccaga gaagaggagg    1800
agaagaagaa gaaa                                                      1814

<210> SEQ ID NO 94
<211> LENGTH: 1416
<212> TYPE: DNA
<213> ORGANISM: Oryza sativa
<220> FEATURE:
<221> NAME/KEY: promoter
<222> LOCATION: (1)..(1416)
<223> OTHER INFORMATION: OsCA promoter

<400> SEQUENCE: 94
atcttggcta tttcccatgg cttctccgct ctactcttgt ccctgtttgg atgacgccgt      60
ccagaccaag acatcaaaac ggggcgacac tgtgaggtta cggtgtcgcc attcgccaca     120
atgtgctcac catgtcacct tgtcgacatt tcgccgcata caagtcgctg tgcgaccgcc     180
```

```
aggtgggccc cactgtgagc agcacgagtg tggcgcgtat ataaatttgt cggatggaga      240
ggcagctgaa ggttttccgc catggcaact gcgtccttcg acatctgcgc gaaggttggg      300
ctcggaattt cgacaggata ctcacagcga aatcaatact ctgctatggc aaatggtacg      360
cactcgtttc gattgttctg ccttcttctg ttttattttt tttcccgtat gtagctgtag      420
ctgctgataa acgtgccatg tattccatct cgttcttgca agcagtttct tagatgagtt      480
aaaatatgta ttccatgtca actgttcact ttagttaggt agaactttct tacattatga      540
ttagttatct acttactctc tctgtccgat aataattatc gcattgattt tttttataat      600
gtttgatcat tcgtcttatt aaaaaaaatt atagaattat tttttttatt ttgtttgtga      660
cttgctttat tatcaaaaaa ataatttaaa tatggcatat ctttttttat atttacaata      720 attttttcaaa aaagatgaat ggtcaaacgt tacacgaaaa aatcaaagcg accactattt      780
tggaatggaa gtagtacctg tagagaaaaa ttaaatatta gttcttaagt gagtgtggac      840
cgaaaaaatt ccttatttat cataaacacg ttttccaaac ttttaaatga tatgtttttt      900
taaatatata aatgaacatg ttctttcaaa aatcaaataa atcacttttt caagtttgta      960
ctgattaata ctagactaat catttgctaa ttgtttatat tgttttactt gccatcataa     1020
ctcatgccaa attgcttttc caaacccacc attagccgct gtggcaagct cagttgctag     1080
cttgaggagg actatacaaa gttgcacaca cgccatggta ctaacgagaa ctggaaaata     1140
tgttgactgg aaaaattgta tcagttcata ttagaaacaa attactgtca gaatgaggaa     1200
aaactcagtc catgccacta aaggcatcag atgcgaattg cgctcctttt ctcctttcaa     1260
ggagtaggca taaacatagg ctctgcagta gtttcatctg agacagtcgg cacgcggggg     1320
cgcgggcgtc tatttgttgc gcgcgcgggc gcggcggcga gacgcgtgtg tagctactgc     1380
tataaggagc gcgccgtgca ccgcctctca catcga                               1416
```

<210> SEQ ID NO 95
<211> LENGTH: 1086
<212> TYPE: DNA
<213> ORGANISM: Zea mays
<220> FEATURE:
<221> NAME/KEY: misc_feature
<222> LOCATION: (1)..(1086)
<223> OTHER INFORMATION: transcription factor

<400> SEQUENCE: 95

```
atgggctcca acgatccaaa cacaccgtcc aaggcctcca aggcgagcga gcaggatcag        60
ccaccggcga caaccacctc cagcgggacc gccagcgtgt acccagagtg gccgtccttt       120
caagcgtatt ccgccattcc accgcacgcc ttttccccac cgaccgtcgc ggccaacccg       180
caggcgcatc cgtacatgtg gggcgcccaa ccaatcgtcc cgccatatgg gaccccacca       240
ccgccgccat atgtcatgta cccgccgggg accgtctatg cgcacccgtc cacaccacca       300
gcgatgcacc catttgggca ctatccgatg ccgacaaatg ccatgccga aacacacggg       360 gccgccccga gcgcgccaga aatgaacggc aaatccgagc caggccgcac aagcgcccca       420
agcgcgaacg gcattaccag ccactccgaa tccggcagcg aaagcgaatc cgaaggctcc       480
gatgacaatt cccaaaatga ttcccactcc aaggataacg acgggaagga agacgggaat       540
tcccaaaacg ggatgagcta ttccggctcc caggggtcg tgaatcagac catggcgatg       600
ctcccgatgc agccagggc gatggtcgg ggggtgccga gctccacagc cgccaatctg       660
aatatcgggg tggactactg ggccgcgccg gggtccgccg cggtcccggc ggcgcacggg       720
```

| aaggcccag | cggggagcgc | gaggggcgac | cagtgggatg | agcgcgagct | caaaaaacag | 780 |
| aaaaggaaac | aatccaatcg | cgaaagcgcg | cgcaggtccc | gcctcaggaa | gcaggccgag | 840 |
| tgtgaggaac | tggggcagcg | cgccgaagcg | ctgcgcagcg | aaaactccag | cctgcgcgcc | 900 |
| gagctcgagc | gcatcaggaa | agaatacgag | cagctcctct | cccagaatgc | gtccctcaaa | 960 |
| gagaagctgg | gggcggcgag | ctccgacagc | ctgccagaca | tgaatgaaca | aaatgatggc | 1020 |
| gacggcgatg | ggggctacag | gaaacaaccg | gattccgacg | ccaccaacc | gggcagcgaa | 1080 |
| tcctga | | | | | | 1086 |

<210> SEQ ID NO 96
<211> LENGTH: 361
<212> TYPE: PRT
<213> ORGANISM: Zea mays
<220> FEATURE:
<221> NAME/KEY: MISC_FEATURE
<222> LOCATION: (1)..(361)
<223> OTHER INFORMATION: transcription factor

<400> SEQUENCE: 96

```
Met Gly Ser Asn Asp Pro Asn Thr Pro Ser Lys Ala Ser Lys Ala Ser
1               5                   10                  15

Glu Gln Asp Gln Pro Pro Ala Thr Thr Thr Ser Ser Gly Thr Ala Ser
            20                  25                  30

Val Tyr Pro Glu Trp Pro Ser Phe Gln Ala Tyr Ser Ala Ile Pro Pro
        35                  40                  45

His Ala Phe Phe Pro Pro Thr Val Ala Ala Asn Pro Gln Ala His Pro
    50                  55                  60

Tyr Met Trp Gly Ala Gln Pro Ile Val Pro Tyr Gly Thr Pro Pro
65                  70                  75                  80

Pro Pro Pro Tyr Val Met Tyr Pro Pro Gly Thr Val Tyr Ala His Pro
                85                  90                  95

Ser Thr Pro Pro Ala Met His Pro Phe Gly His Tyr Pro Met Pro Thr
            100                 105                 110

Asn Gly His Ala Glu Thr His Gly Ala Ala Pro Ser Ala Pro Glu Met
        115                 120                 125

Asn Gly Lys Ser Glu Pro Gly Arg Thr Ser Ala Pro Ser Ala Asn Gly
    130                 135                 140

Ile Thr Ser His Ser Glu Ser Gly Ser Glu Ser Glu Ser Glu Gly Ser
145                 150                 155                 160

Asp Asp Asn Ser Gln Asn Asp Ser His Ser Lys Asp Asn Asp Gly Lys
                165                 170                 175

Glu Asp Gly Asn Ser Gln Asn Gly Met Ser Tyr Ser Gly Ser Gln Gly
            180                 185                 190

Val Val Asn Gln Thr Met Ala Met Leu Pro Met Gln Pro Gly Ala Met
        195                 200                 205

Val Gly Gly Val Pro Ser Ser Thr Ala Ala Asn Leu Asn Ile Gly Val
    210                 215                 220

Asp Tyr Trp Ala Ala Pro Gly Ser Ala Ala Val Pro Ala Ala His Gly
225                 230                 235                 240

Lys Ala Pro Ala Gly Ser Ala Arg Gly Asp Gln Trp Asp Glu Arg Glu
                245                 250                 255

Leu Lys Lys Gln Lys Arg Lys Gln Ser Asn Arg Glu Ser Ala Arg Arg
            260                 265                 270

Ser Arg Leu Arg Lys Gln Ala Glu Cys Glu Glu Leu Gly Gln Arg Ala
        275                 280                 285
```

Glu Ala Leu Arg Ser Glu Asn Ser Ser Leu Arg Ala Glu Leu Glu Arg
        290                 295                 300

Ile Arg Lys Glu Tyr Glu Gln Leu Leu Ser Gln Asn Ala Ser Leu Lys
305                 310                 315                 320

Glu Lys Leu Gly Ala Ala Ser Ser Asp Ser Leu Pro Asp Met Asn Glu
                325                 330                 335

Gln Asn Asp Gly Asp Gly Asp Gly Tyr Arg Lys Gln Pro Asp Ser
            340                 345                 350

Asp Gly His Gln Pro Gly Ser Glu Ser
        355                 360

<210> SEQ ID NO 97
<211> LENGTH: 315
<212> TYPE: DNA
<213> ORGANISM: Oryza sativa
<220> FEATURE:
<221> NAME/KEY: 3'UTR
<222> LOCATION: (1)..(315)
<223> OTHER INFORMATION: OsCA 3'UTR

<400> SEQUENCE: 97
gttcatccga ccgtccgtcc gttcagttcg tcagtttacg ccaacgcttt tgcataagta    60
ctacctgagg atatcgtccc cgatcatcga tgtgaacgcg tggagtacta ctacgtacgt   120
accggatggt tcgatatatg tgaatgctgt attaagtaat aacaagaaat atatctcctc   180 tacttttttcc tgacgcggag ttgtactgcc tatgatgcat aatttgatcg cagtgtgatc   240
aaaagacatc agctataatg tcttaataat attattatga gagtttacc tttttactac    300 cttttactct ggtaa                                                    315

<210> SEQ ID NO 98
<211> LENGTH: 912
<212> TYPE: DNA
<213> ORGANISM: Zea mays
<220> FEATURE:
<221> NAME/KEY: promoter
<222> LOCATION: (1)..(912)
<223> OTHER INFORMATION: ZmRbcS promoter

<400> SEQUENCE: 98
gagctccctt taatctggcg ctagatctgc atccgcggct tgcaaagata aatggcacat    60
ttagtgtgtt attttgcaat acctttcata gtagatatcc ttaaatgcag ttttaggcat   120
gtttgggtaa ttaaataaca ttttaggag gagttttaga tttaccttc tttcgtgatg    180 actgatgaca gacgtgggga attcaaatgc aactctagcg aaagttcata tattttttcat  240 aaatagctga ggctggggta attatttttt ttgtagaaaa atagaatagg tggaatggtt   300
ggggaaggcg taggcgctcg tggacgacgc ccgataaaag acaagaggcg gaattgccat   360
gaattcgagg tagctaagta aggcgcatat atatgccaaa aaattctact gtcactttcc   420
aatttcaatg cgctgccaaa caagccatcc tggaaactga cttgaattca gcccaattct   480
gtagatccaa acagggccgg cgtcagtgcc tcaggtgaga gagcagcaga cgatgcaaag   540
agccaaaact gcaagcagac gcagccgaag ccgaagccga agcccaagcc caaaactgtt   600
ttgtctttgc ccagaaccgc gacgagccta aactgcgctt cctcctatct acaagtccct   660
ggcacatcac gcatagtcca accatggcgc gcaggcgata aggcgcgcca cggggacgcg   720
acatgtggtg gcggacgcga tcaggatagg gccaggctgg ccgggcgcgg ccacgggaga   780
acggtggcca ctcgtcccac atccgcttcg tcctgtcctg tactgcgtcc tgcccccaac   840

-continued

```
gagagccgga gccggccatc ccgtcgcaca ctctccccct ctatatatgc cgtcggtgtg    900
ggggagccta ct                                                        912
```

<210> SEQ ID NO 99
<211> LENGTH: 1404
<212> TYPE: DNA
<213> ORGANISM: Synechococcus sp.
<220> FEATURE:
<221> NAME/KEY: misc_feature
<222> LOCATION: (1)..(1404)
<223> OTHER INFORMATION: ictB

<400> SEQUENCE: 99

```
atgacagtgt ggcagacact cacattcgct cattaccagc ctcagcagtg gggccattct     60
tctttcctcc ataggctctt cggctctctc agggcttgga gggcttcttc tcagctcctc    120
gtgtggtctg aggctctcgg cggcttcctc ctcgctgtgg tgtacggctc tgctcctttc    180
gtgccttctt ctgctctcgg cctcggcctc gctgctattg ctgcttactg ggctctcctc    240
tctctcacag atattgatct caggcaggct acacctattc attggctcgt gctcctctac    300
tggggcgtgg atgctctcgc tacaggcctc tctcctgtga gggctgctgc tctcgtgggc    360
ctcgctaagc tcacactcta cctcctcgtg ttcgctctcg ctgctagggt gctcaggaat    420
cctaggctca ggtctctcct cttctctgtg gtggtgatca catctctctt cgtgtctgtg    480
tacggcctca atcagtggat ttacggcgtg gaggagctcg ctacatgggt ggataggaat    540
tctgtggctg atttcacatc tagggtgtac tcttacctcg gcaatcctaa tctcctcgct    600
gcttacctcg tgcctacaac agctttctct gctgctgcta ttggcgtgtg gaggggctgg    660
ctccctaagc tcctcgctat tgctgctaca ggcgcttctt ctctctgcct cattctcaca    720
tactctaggg gcggctggct cggcttcgtg gctatgattt tcgtgtgggc tctcctcggc    780
ctctactggt tccagcctag gctccctgct ccttggagga ggtggctctt ccctgtggtg    840
ctcggcggcc tcgtggctgt gctcctcgtg gctgtgctcg gcctcgagcc tctcagggtg    900
agggtgctct ctattttcgt gggcagggag gattcttcta ataatttcag gattaatgtg    960
tggctcgctg tgctccagat gattcaggat aggccttggc tcggcattgg ccctggcaat   1020
acagctttca atctcgtgta ccctctctac cagcaggcta ggttcacagc tctctctgct   1080
tactctgtgc ctctcgaggt ggctgtggag ggcggcctcc tcggcctcac agctttcgct   1140
tggctcctcc tcgtgacagc tgtgacagct gtgcgccagg tgtctaggct caggagggat   1200
aggaatcctc aggctttctg gctcatggct tctctcgctg gcctcgctgg catgctcggc   1260
catggcctct tcgatacagt gctctacagg cctgaggctt ctacactctg gtggctctgc   1320
attggcgcta ttgcttcttt ctggcagcct cagccttcta gcagctccc tcctgaggct   1380 gagcattctg atgagaagat gtga                                          1404
```

<210> SEQ ID NO 100
<211> LENGTH: 467
<212> TYPE: PRT
<213> ORGANISM: Synechococcus sp.
<220> FEATURE:
<221> NAME/KEY: MISC_FEATURE
<222> LOCATION: (1)..(467)
<223> OTHER INFORMATION: ictB

<400> SEQUENCE: 100

```
Met Thr Val Trp Gln Thr Leu Thr Phe Ala His Tyr Gln Pro Gln Gln
1               5                   10                  15
```

```
Trp Gly His Ser Ser Phe Leu His Arg Leu Phe Gly Ser Leu Arg Ala
             20                  25                  30

Trp Arg Ala Ser Ser Gln Leu Leu Val Trp Ser Glu Ala Leu Gly Gly
         35                  40                  45

Phe Leu Leu Ala Val Val Tyr Gly Ser Ala Pro Phe Val Pro Ser Ser
 50                  55                  60

Ala Leu Gly Leu Gly Leu Ala Ala Ile Ala Ala Tyr Trp Ala Leu Leu
 65                  70                  75                  80

Ser Leu Thr Asp Ile Asp Leu Arg Gln Ala Thr Pro Ile His Trp Leu
                 85                  90                  95

Val Leu Leu Tyr Trp Gly Val Asp Ala Leu Ala Thr Gly Leu Ser Pro
            100                 105                 110

Val Arg Ala Ala Ala Leu Val Gly Leu Ala Lys Leu Thr Leu Tyr Leu
            115                 120                 125

Leu Val Phe Ala Leu Ala Ala Arg Val Leu Arg Asn Pro Arg Leu Arg
130                 135                 140

Ser Leu Leu Phe Ser Val Val Ile Thr Ser Leu Phe Val Ser Val
145                 150                 155                 160

Tyr Gly Leu Asn Gln Trp Ile Tyr Gly Val Glu Glu Leu Ala Thr Trp
            165                 170                 175

Val Asp Arg Asn Ser Val Ala Asp Phe Thr Ser Arg Val Tyr Ser Tyr
            180                 185                 190

Leu Gly Asn Pro Asn Leu Leu Ala Ala Tyr Leu Val Pro Thr Thr Ala
            195                 200                 205

Phe Ser Ala Ala Ala Ile Gly Val Trp Arg Gly Trp Leu Pro Lys Leu
            210                 215                 220

Leu Ala Ile Ala Ala Thr Gly Ala Ser Ser Leu Cys Leu Ile Leu Thr
225                 230                 235                 240

Tyr Ser Arg Gly Gly Trp Leu Gly Phe Val Ala Met Ile Phe Val Trp
                245                 250                 255

Ala Leu Leu Gly Leu Tyr Trp Phe Gln Pro Arg Leu Pro Ala Pro Trp
            260                 265                 270

Arg Arg Trp Leu Phe Pro Val Val Leu Gly Gly Leu Val Ala Val Leu
            275                 280                 285

Leu Val Ala Val Leu Gly Leu Glu Pro Leu Arg Val Arg Val Leu Ser
290                 295                 300

Ile Phe Val Gly Arg Glu Asp Ser Ser Asn Asn Phe Arg Ile Asn Val
305                 310                 315                 320

Trp Leu Ala Val Leu Gln Met Ile Gln Asp Arg Pro Trp Leu Gly Ile
                325                 330                 335

Gly Pro Gly Asn Thr Ala Phe Asn Leu Val Tyr Pro Leu Tyr Gln Gln
            340                 345                 350

Ala Arg Phe Thr Ala Leu Ser Ala Tyr Ser Val Pro Leu Glu Val Ala
            355                 360                 365

Val Glu Gly Gly Leu Leu Gly Leu Thr Ala Phe Ala Trp Leu Leu Leu
            370                 375                 380

Val Thr Ala Val Thr Ala Val Arg Gln Val Ser Arg Leu Arg Arg Asp
385                 390                 395                 400

Arg Asn Pro Gln Ala Phe Trp Leu Met Ala Ser Leu Ala Gly Leu Ala
                405                 410                 415

Gly Met Leu Gly His Gly Leu Phe Asp Thr Val Leu Tyr Arg Pro Glu
            420                 425                 430
```

-continued

```
Ala Ser Thr Leu Trp Trp Leu Cys Ile Gly Ala Ile Ala Ser Phe Trp
        435                 440                 445

Gln Pro Gln Pro Ser Lys Gln Leu Pro Pro Glu Ala Glu His Ser Asp
    450                 455                 460

Glu Lys Met
465
```

US 11,060,102 B2

INCREASING PLANT GROWTH AND YIELD BY USING A PSAN SEQUENCE

CROSS-REFERENCE TO RELATED APPLICATIONS

This application is a national stage filing under 35 U.S.C. 371 of PCT/IB2017/053547 filed Jun. 14, 2017, which International Application was published by the International Bureau in English on Dec. 28, 2017, and claims priority from U.S. Provisional Application No. 62/353,866, filed Jun. 23, 2016 which applications are hereby incorporated by reference in their entirety in this application.

FIELD OF THE INVENTION

The invention is drawn to compositions and methods for increasing plant growth and yield through expression of a photosystem I reaction center subunit N (PSAN) gene in a plant.

BACKGROUND OF THE INVENTION

The ever-increasing world population and the dwindling supply of arable land available for agriculture fuels research towards developing plants with increased biomass and yield. Conventional means for crop and horticultural improvements utilize selective breeding techniques to identify plants having desirable characteristics. However, such selective breeding techniques have several drawbacks, namely that these techniques are typically labor intensive and result in plants that often contain heterogeneous genetic components that may not always result in the desirable trait being passed on from parent plants. Advances in molecular biology provide means to modify the germplasm of plants. Genetic engineering of plants entails the isolation and manipulation of genetic material (typically in the form of DNA or RNA) and the subsequent introduction of that genetic material into a plant. Such technology has the capacity to deliver crops or plants having various improved economic, agronomic or horticultural traits.

Traits of interest include plant biomass and yield. Yield is normally defined as the measurable produce of economic value from a crop. This may be defined in terms of quantity and/or quality. Yield is directly dependent on several factors, for example, the number and size of the organs, plant architecture (for example, the number of branches), seed production, leaf senescence and more. Root development, nutrient uptake, stress tolerance and early vigor may also be important factors in determining yield. Optimizing the abovementioned factors may therefore contribute to increasing crop yield.

An increase in seed yield is a particularly important trait since the seeds of many plants are important for human and animal consumption. Crops such as corn, rice, wheat, canola and soybean account for over half the total human caloric intake, whether through direct consumption of the seeds themselves or through consumption of meat products raised on processed seeds. They are also a source of sugars, oils and many kinds of metabolites used in industrial processes. Seeds contain an embryo (the source of new shoots and roots) and an endosperm (the source of nutrients for embryo growth during germination and during early growth of seedlings). The development of a seed involves many genes, and requires the transfer of metabolites from the roots, leaves and stems into the growing seed. The endosperm, in particular, assimilates the metabolic precursors of carbohydrates, oils and proteins and synthesizes them into storage macromolecules to fill out the grain. An increase in plant biomass is important for forage crops like alfalfa, silage corn and hay. Many genes are involved in plant growth and development. Modulating the expression of one or more such genes in a plant can produce a plant with improved growth and development relative to a control plant, but often can produce a plant with impaired growth and development relative to a control plant. Therefore, methods to improve plant growth and development are needed.

SUMMARY OF THE INVENTION

Compositions and methods for regulating gene expression in a plant are provided. The methods increase plant growth and higher crop yield. Such methods include increasing the expression of at least one photosystem I reaction center subunit N (PSAN) gene in a plant of interest. The invention also encompasses constructs comprising a promoter that drives expression in a plant cell operably linked to a PSAN coding sequence. Compositions further comprise plants, plant seeds, plant organs, plant cells, and other plant parts that have increased expression of a PSAN sequence. The invention includes methods that can be utilized to increase expression of a PSAN gene in a plant. Such PSAN gene may be a native sequence or alternatively, may be a sequence that is heterologous to the plant of interest.

Embodiments of the invention include:
1. A method for increasing crop yield comprising transforming a plant with at least one PSAN protein-encoding sequence.
2. The method of embodiment 1, wherein said PSAN protein-encoding sequence comprises SEQ ID NO:1, or encodes a protein selected from the group consisting of SEQ ID NOs:2 and 7-88.
3. The method of embodiment 1, wherein said PSAN protein-encoding sequence encodes a protein with at least 80%, 90%, 95%, 96%, 97%, 98%, or 99% sequence identity to a sequence selected from the group consisting of SEQ ID NOs:2 and 7-88, and that has PSAN function.
4. The method of embodiment 1, wherein said PSAN protein-encoding sequence encodes a protein with at least 80%, 85%, 90%, 95%, 96%, 97%, 98%, or 99% sequence positives relative to a sequence selected from the group consisting of SEQ ID NOs:2 and 7-88, and that has PSAN function.
5. A plant having stably incorporated into its genome a promoter that drives expression in a plant operably linked to a PSAN protein-encoding sequence, wherein said promoter is heterologous to said PSAN protein-encoding sequence.
6. The plant of embodiment 5, wherein said PSAN protein-encoding sequence comprises SEQ ID NO:1, or encodes a protein selected from the group consisting of SEQ ID NOs: 2 and 7-88.
7. The plant of embodiment 5, wherein said PSAN protein-encoding sequence encodes a protein with at least 80%, 85%, 90%, 95%, 96%, 97%, 98%, or 99% sequence identity to a sequence selected from the group consisting of SEQ ID NOs:2 and 7-88, and that has PSAN function.
8. The plant of embodiment 5, wherein said PSAN protein-encoding sequence encodes a protein with at least 80%, 85%, 90%, 95%, 96%, 97%, 98%, or 99% sequence positives relative to a sequence selected from the group consisting of SEQ ID NOs:2 and 7-88, and that has PSAN function.
9. Transformed seed of any one of the plants of embodiments 5-8.
10. The plant of any one of embodiments 5-8 wherein said plant is a monocot.
11. The plant of embodiment 10 wherein said plant is from the genus *Zea, Oryza, Triticum, Sorghum, Secale, Eleusine, Setaria, Saccharum, Miscanthus, Panicum, Pennisetum, Megathyrsus, Cocos, Ananas, Musa, Elaeis, Avena*, or *Hordeum*.
12. The plant of any one of embodiments 5-8 wherein said plant is a dicot.
13. The plant of embodiment 12 wherein said plant is from the genus *Glycine, Brassica, Medicago, Helianthus, Carthamus, Nicotiana, Solanum, Gossypium, Ipomoea, Manihot, Coffea, Citrus, Theobroma, Camellia, Persea, Ficus, Psidium, Mangifera, Olea, Carica, Anacardium, Macadamia, Prunus, Beta, Populus*, or *Eucalyptus*.
14. The plant of any one of embodiments 5-8 wherein said plant exhibits increased growth relative to a control plant.
15. The plant of any one of embodiments 5-8 wherein said plant exhibits increased biomass yield relative to a control plant.
16. The plant of any one of embodiments 5-8 wherein said plant exhibits increased seed yield relative to a control plant.
17. The method of any one of embodiments 1-4, wherein said PSAN protein-encoding sequence is expressed from a constitutive promoter.
18. The method of embodiment 17, wherein said constitutive promoter comprises SEQ ID NO:3.
19. The method of any one of embodiments 1-4, wherein said PSAN protein-encoding sequence is expressed from a mesophyll-preferred promoter.
20. The method of embodiment 19, wherein said mesophyll-preferred promoter comprises SEQ ID NO:5.
21. The plant of any one of embodiments 5-8, wherein said promoter that drives expression in a plant is a constitutive promoter.
22. The plant of embodiment 21, wherein said constitutive promoter comprises SEQ ID NO:3.
23. The plant of any one of embodiments 5-8, wherein said promoter that drives expression in a plant is a mesophyll-preferred promoter.
24. The plant of embodiment 23, wherein said mesophyll-preferred comprises SEQ ID NO:5.
25. A DNA construct comprising, in operable linkage,
    a. A promoter that is functional in a plant cell and,
    b. A nucleic acid sequence encoding a PSAN protein.
26. The DNA construct of embodiment 25, wherein said nucleic acid sequence encoding a PSAN protein comprises SEQ ID NO:1, or encodes a protein selected from the group consisting of SEQ ID NOs:2 and 7-88.
27. The DNA construct of embodiment 25 or 26, wherein said nucleic acid sequence encoding a PSAN protein encodes a protein with at least 80%, 85%, 90%, 95%, 96%, 97%, 98%, or 99% sequence identity to a sequence selected from the group consisting of SEQ ID NOs:2 and 7-88, and that has PSAN function.
28. The DNA construct of embodiment 25 or 26, wherein said nucleic acid sequence encoding a PSAN protein encodes a protein with at least 80%, 85%, 90%, 95%, 96%, 97%, 98%, or 99% sequence positives relative to a sequence selected from the group consisting of SEQ ID NOs:2 and 7-88, and that has PSAN function.
29. The DNA construct of any one of embodiments 25-28, wherein said promoter that is functional in a plant cell is selected from the group of SEQ ID NOs:3 and 5.
30. The DNA construct of any one of embodiments 25-29, wherein said promoter that is functional in a plant cell is heterologous to said nucleic acid sequence encoding a PSAN protein.
31. A method for increasing crop yield comprising modulating the expression of at least one PSAN protein-encoding sequence in a plant.
32. The method of embodiment 31 wherein said modulating the expression comprises increasing the expression of at least one PSAN protein-encoding sequence in a plant.
33. The method of embodiment 32, wherein said increasing the expression comprises increasing the expression of a native PSAN sequence in said plant or increasing the expression of a native PSAN protein-encoding sequence in said plant.
34. The plant of embodiment 5, wherein said promoter that drives expression in a plant is a promoter that is active in leaf tissue.
35. The plant of embodiment 34, wherein said promoter that is active in leaf tissue comprises SEQ ID NO:5.
36. The method of any one of embodiments 1-4, wherein said PSAN protein-encoding sequence is expressed from a promoter that is active in leaf tissue.
37. The method of embodiment 36, wherein said promoter that is active in leaf tissue comprises SEQ ID NO:5.
38. The DNA construct of embodiment 25, wherein said promoter that is functional in a plant cell is a promoter that is active in leaf tissue.
39. The DNA construct of embodiment 38, wherein said promoter that is active in leaf tissue comprises SEQ ID NO:5.
40. The method of any one of embodiments 1-4, further comprising transforming a plant with at least one additional protein-encoding sequence.
41. The method of embodiment 40 wherein said additional protein-encoding sequence shares at least 70% identity with a sequence selected from the group of SEQ ID NOs:91, 95, and 99, or encodes a protein that shares at least 80% identity with a sequence selected from the group of SEQ ID NOs:92, 96, and 100.
42. The method of embodiment 41 wherein said additional protein-encoding sequence comprises a sequence selected from the group of SEQ ID NOs:91, 95, and 99, or encodes a protein that comprises a sequence selected from the group of SEQ ID NOs:92, 96, and 100.
43. The plant of any one of embodiments 5-8, wherein said plant has stably incorporated into its genome a second promoter that drives expression of at least one additional coding sequence, wherein said second promoter is heterologous to said additional coding sequence.
44. The plant of embodiment 43, wherein said additional coding sequence shares at least 70% identity with a sequence selected from the group of SEQ ID NOs:91, 95, and 99, or encodes a protein that shares at least 80% identity with a sequence selected from the group of SEQ ID NOs:92, 96, and 100.
45. The plant of embodiment 44, wherein said additional coding sequence comprises a sequence selected from the group of SEQ ID NOs:91, 95, and 99, or encodes a protein that comprises a sequence selected from the group of SEQ ID NOs:92, 96, and 100.

46. The DNA construct of any one of embodiments 25-30, further comprising, in operable linkage,
    a. A second promoter that is functional in a plant cell and,
    b. A nucleic acid sequence encoding an additional protein, wherein said second promoter is heterologous to said nucleic acid sequence encoding an additional protein.

47. The DNA construct of embodiment 46, wherein said nucleic acid sequence encoding an additional protein shares at least 70% identity with a sequence selected from the group of SEQ ID NOs:91, 95, and 99, or encodes a protein that shares at least 80% identity with a sequence selected from the group of SEQ ID NOs:92, 96, and 100.

48. The DNA construct of embodiment 47, wherein said nucleic acid sequence encoding an additional protein comprises a sequence selected from the group of SEQ ID NOs:91, 95, and 99, or encodes a protein that comprises a sequence selected from the group of SEQ ID NOs:92, 96, and 100.

DETAILED DESCRIPTION OF THE INVENTION

Compositions and methods for increasing crop biomass and yield are provided. The methods include increasing the expression of at least one photosystem I reaction center subunit N (PSAN) gene in a plant of interest. Crop yield is an extremely complex trait that results from the growth of a crop plant through all stages of its development and allocation of plant resources to the harvestable portions of the plant. In some crops including but not limited to maize and soybean, the primary harvestable portions may include seeds, with secondary applications from the remainder of the biomass (e.g., leaves and stems). In other crops including but not limited to sugarcane and alfalfa, the primary harvestable portions of the plant consist of the stems or entire above-ground portion of the plant. In other crops including but not limited to potato and carrot, the primary harvestable portions of the plant are found below-ground. Regardless of the harvested portion(s) of the crop plant, the accumulation of harvestable biomass results from plant growth and allocation of photosynthetically fixed carbon to the harvested portion(s) of the plant. Plant growth may be manipulated by modulating the expression of one or more plant genes. This modulation can alter the function of one or more metabolic pathways that contributes to plant growth and accumulation of harvestable biomass.

Methods of the invention include the manipulation of plant growth for increased yield through modulation of the expression of one or more genes encoding a PSAN protein. In a preferred embodiment, the expression of a PSAN-encoding gene is upregulated relative to PSAN expression levels in a control plant, resulting in increased harvestable biomass in plants with increased PSAN expression relative to control plants. Any methods for increasing the activity or expression of a PSAN-encoding sequence in a plant are encompassed by the present invention.

The compositions of the invention include constructs comprising the coding sequence set forth in SEQ ID NO:1 or variants thereof as well as a coding sequence encoding a protein selected from the group of SEQ ID NOs:2 and 7-88 or variants thereof, operably linked to a promoter that is functional in a plant cell. By "promoter" is intended to mean a regulatory region of DNA that is capable of driving expression of a sequence in a plant or plant cell. It is recognized that having identified the PSAN protein sequences disclosed herein, it is within the state of the art to isolate and identify additional PSAN protein sequences and nucleotide sequences encoding PSAN protein sequences, for instance through BLAST searches, PCR assays, and the like.

The coding sequences of the present invention, when assembled within a DNA construct such that a promoter is operably linked to the coding sequence of interest, enable expression and accumulation of PSAN protein in the cells of a plant stably transformed with this DNA construct. "Operably linked" is intended to mean a functional linkage between two or more elements. For example, an operable linkage between a promoter of the present invention and a heterologous nucleotide of interest is a functional link that allows for expression of the heterologous nucleotide sequence of interest. Operably linked elements may be contiguous or non-contiguous. When used to refer to the joining of two protein coding regions, by operably linked is intended that the coding regions are in the same reading frame. The cassette may additionally contain at least one additional gene to be co-transformed into the plant. Alternatively, the additional gene(s) can be provided on multiple expression cassettes or DNA constructs. The expression cassette may additionally contain selectable marker genes.

In this manner, the nucleotide sequences encoding the PSAN proteins of the invention are provided in expression cassettes or expression constructs along with a promoter sequence of interest, typically a heterologous promoter sequence, for expression in the plant of interest. By "heterologous promoter sequence" is intended to mean a sequence that is not naturally operably linked with the PSAN protein-encoding nucleotide sequence. While the PSAN-encoding nucleotide sequence and the promoter sequence are heterologous to each other, either the PSAN-encoding nucleotide sequence or the heterologous promoter sequence may be homologous, or native, or heterologous, or foreign, to the plant host. It is recognized that the promoter may also drive expression of its homologous or native nucleotide sequence. In this case, the transformed plant will have a change in phenotype.

Fragments and variants of the polynucleotides and amino acid sequences of the present invention may also be expressed by promoters that are operable in plant cells. By "fragment" is intended a portion of the polynucleotide or a portion of the amino acid sequence. "Variants" is intended to mean substantially similar sequences. For polynucleotides, a variant comprises a polynucleotide having deletions (i.e., truncations) at the 5' and/or 3' end; deletion and/or addition of one or more nucleotides at one or more internal sites in the native polynucleotide; and/or substitution of one or more nucleotides at one or more sites in the native polynucleotide. As used herein, a "native" polynucleotide or polypeptide comprises a naturally occurring nucleotide sequence or amino acid sequence, respectively. Generally, variants of a particular polynucleotide of the invention will have at least about 75%, 80%, 85%, 90%, 91%, 92%, 93%, 94%, 95%, 96%, 97%, 98%, 99% or more sequence identity to that particular polynucleotide as determined by sequence alignment programs and parameters as described elsewhere herein. Fragments and variants of the polynucleotides disclosed herein can encode proteins that retain PSAN function.

"Variant" amino acid or protein is intended to mean an amino acid or protein derived from the native amino acid or protein by deletion (so-called truncation) of one or more amino acids at the N-terminal and/or C-terminal end of the native protein; deletion and/or addition of one or more amino acids at one or more internal sites in the native protein; or substitution of one or more amino acids at one or more sites in the native protein. Variant proteins encompassed by the present invention are biologically active, that is they continue to possess the desired biological activity of the native protein, such as an ability to interact with other photosystem I proteins to form a functional protein complex. Biologically active variants of a native polypeptide will have at least about 80%, 85%, 90%, 91%, 92%, 93%, 94%, 95%, 96%, 97%, 98%, 99% or more sequence identity to the amino acid sequence for the native sequence as determined by sequence alignment programs and parameters described herein. In some embodiments, the variant polypeptide sequences will comprise conservative amino acid substitutions. The number of such conservative amino acid substitutions, summed with the number of amino acid identities, can be used to calculate the sequence positives when this sum is divided by the total number of amino acids in the sequence of interest. Sequence positive calculations are performed on the NCBI BLAST server that can be accessed on the world wide web at blast.ncbi.nlm.nih.gov/Blast.cgi. A biologically active variant of a protein of the invention may differ from that protein by as few as 1-15 amino acid residues, as few as 1-10, such as 6-10, as few as 5, as few as 4, 3, 2, or even 1 amino acid residue.

Amino acids can be generally categorized as aliphatic, hydroxyl or sulfur/selenium-containing, cyclic, aromatic, basic, or acidic and their amide. Without being limited by theory, conservative amino acid substitutions may be preferable in some cases to non-conservative amino acid substitutions for the generation of variant protein sequences, as conservative substitutions may be more likely than non-conservative substitutions to allow the variant protein to retain its biological activity. Polynucleotides encoding a polypeptide having one or more amino acid substitutions in the sequence are contemplated within the scope of the present invention. Table 1 below provides a listing of examples of amino acids belong to each class.

TABLE 1

Classes of Amino Acids

| Amino Acid Class | Example Amino Acids |
| --- | --- |
| Aliphatic | Gly, Ala, Val, Leu, Ile |
| Hydroxyl or sulfur/selenium-containing | Ser, Cys, Thr, Met, Sec |
| Cyclic | Pro |
| Aromatic | Phe, Tyr, Trp |
| Basic | His, Lys, Arg |
| Acidic and their Amide | Asp, Glu, Asn, Gln |

Variant sequences may also be identified by analysis of existing databases of sequenced genomes. In this manner, corresponding sequences can be identified and used in the methods of the invention.

Methods of alignment of sequences for comparison are well known in the art. Thus, the determination of percent sequence identity between any two sequences can be accomplished using a mathematical algorithm. Non-limiting examples of such mathematical algorithms are the algorithm of Myers and Miller (1988) *CABIOS* 4:11-17; the local alignment algorithm of Smith et al. (1981) *Adv. Appl. Math.* 2:482; the global alignment algorithm of Needleman and Wunsch (1970) *J. Mol. Biol.* 48:443-453; the search-for-local alignment method of Pearson and Lipman (1988) *Proc. Natl. Acad. Sci.* 85:2444-2448; the algorithm of Karlin and Altschul (1990) *Proc. Natl. Acad. Sci. USA* 87:2264-2268, modified as in Karlin and Altschul (1993) *Proc. Natl. Acad. Sci. USA* 90:5873-5877.

Computer implementations of these mathematical algorithms can be utilized for comparison of sequences to determine sequence identity. Such implementations include, but are not limited to: CLUSTAL in the PC/Gene program (available from Intelligenetics, Mountain View, Calif.); the ALIGN program (Version 2.0) and GAP, BESTFIT, BLAST, FASTA, and TFASTA in the GCG Wisconsin Genetics Software Package, Version 10 (available from Accelrys Inc., 9685 Scranton Road, San Diego, Calif., USA). Alignments using these programs can be performed using the default parameters. The CLUSTAL program is well described by Higgins et al. (1988) *Gene* 73:237-244 (1988); Higgins et al. (1989) *CABIOS* 5:151-153; Corpet et al. (1988) *Nucleic Acids Res.* 16:10881-90; Huang et al. (1992) *CABIOS* 8:155-65; and Pearson et al. (1994) *Meth. Mol. Biol.* 24:307-331. The ALIGN program is based on the algorithm of Myers and Miller (1988) supra. A PAM120 weight residue table, a gap length penalty of 12, and a gap penalty of 4 can be used with the ALIGN program when comparing amino acid sequences. The BLAST programs of Altschul et al (1990) *J. Mol. Biol.* 215:403 are based on the algorithm of Karlin and Altschul (1990) supra. BLAST nucleotide searches can be performed with the BLASTN program, score=100, wordlength=12, to obtain nucleotide sequences homologous to a nucleotide sequence encoding a protein of the invention. BLAST protein searches can be performed with the BLASTX program, score=50, wordlength=3, to obtain amino acid sequences homologous to a protein or polypeptide of the invention. To obtain gapped alignments for comparison purposes, Gapped BLAST (in BLAST 2.0) can be utilized as described in Altschul et al. (1997) *Nucleic Acids Res.* 25:3389. Alternatively, PSI-BLAST (in BLAST 2.0) can be used to perform an iterated search that detects distant relationships between molecules. See Altschul et al. (1997) supra. When utilizing BLAST, Gapped BLAST, PSI-BLAST, the default parameters of the respective programs (e.g., BLASTN for nucleotide sequences, BLASTX for proteins) can be used. See—the website located at ncbi.nlm-.nih.gov. Alignment may also be performed manually by inspection.

Such genes and coding regions can be codon optimized for expression in a plant of interest. A "codon-optimized gene" is a gene having its frequency of codon usage designed to mimic the frequency of preferred codon usage of the host cell. Nucleic acid molecules can be codon optimized, either wholly or in part. Because any one amino acid (except for methionine and tryptophan) is encoded by a number of codons, the sequence of the nucleic acid molecule may be changed without changing the encoded amino acid. Codon optimization is when one or more codons are altered at the nucleic acid level such that the amino acids are not changed but expression in a particular host organism is increased. Those having ordinary skill in the art will recognize that codon tables and other references providing preference information for a wide range of organisms are available in the art (see, e.g., Zhang et al. (1991) *Gene* 105:61-72; Murray et al. (1989) *Nucl. Acids Res.* 17:477-508). Methodology for optimizing a nucleotide sequence for expression in a plant is provided, for example, in U.S. Pat. No. 6,015,891, and the references cited therein, as well as in WO 2012/142,371, and the references cited therein.

The nucleotide sequences of the invention may be used in recombinant polynucleotides. A "recombinant polynucleotide" comprises a combination of two or more chemically linked nucleic acid segments which are not found directly joined in nature. By "directly joined" is intended the two nucleic acid segments are immediately adjacent and joined to one another by a chemical linkage. In specific embodiments, the recombinant polynucleotide comprises a polynucleotide of interest or active variant or fragment thereof such that an additional chemically linked nucleic acid segment is located either 5', 3' or internal to the polynucleotide of interest. Alternatively, the chemically-linked nucleic acid segment of the recombinant polynucleotide can be formed by deletion of a sequence. The additional chemically linked nucleic acid segment or the sequence deleted to join the linked nucleic acid segments can be of any length, including for example, 1, 2, 3, 4, 5, 6, 7, 8, 9, 10, 15, 20 or greater nucleotides. Various methods for making such recombinant polynucleotides are disclosed herein, including, for example, by chemical synthesis or by the manipulation of isolated segments of polynucleotides by genetic engineering techniques. In specific embodiments, the recombinant polynucleotide can comprise a recombinant DNA sequence or a recombinant RNA sequence. A "fragment of a recombinant polynucleotide" comprises at least one of a combination of two or more chemically linked amino acid segments which are not found directly joined in nature.

By "altering" or "modulating" the expression level of a gene is intended that the expression of the gene is upregulated or downregulated. It is recognized that in some instances, plant growth and yield are increased by increasing the expression levels of one or more genes encoding PSAN proteins, i.e. upregulating expression. Likewise, in some instances, plant growth and yield may be increased by decreasing the expression levels of one or more genes encoding PSAN proteins, i.e. downregulating expression. Thus, the invention encompasses the upregulation or downregulation of one or more genes encoding PSAN proteins. Further, the methods include the upregulation of at least one gene encoding a PSAN protein and the downregulation of at least one gene encoding a second PSAN protein in a plant of interest. By modulating the concentration and/or activity of at least one of the genes encoding a PSAN protein in a transgenic plant is intended that the concentration and/or activity is increased or decreased by at least about 1%, about 5%, about 10%, about 20%, about 30%, about 40%, about 50%, about 60%, about 70%, about 80%, or about 90% or greater relative to a native control plant, plant part, or cell which did not have the sequence of the invention introduced.

It is recognized that the expression levels of the genes encoding PSAN proteins of the present invention can be controlled by the use of one or more promoters that are functional in a plant cell. The expression level of the PSAN protein-encoding gene of interest may be measured directly, for example, by assaying for the level of the photosynthetic gene transcript or of the encoded protein in the plant. Methods for such assays are well-known in the art. For example, Northern blotting or quantitative reverse transcriptase-PCR (qRT-PCR) may be used to assess transcript levels, while western blotting, ELISA assays, or enzyme assays may be used to assess protein levels.

A "subject plant or plant cell" is one in which genetic alteration, such as transformation, has been effected as to a PSAN protein-encoding gene of interest, or is a plant or plant cell which is descended from a plant or cell so altered and which comprises the alteration. A "control" or "control plant" or "control plant cell" provides a reference point for measuring changes in phenotype of the subject plant or plant cell. Thus, the expression levels of a PSAN protein-encoding gene of interest are higher or lower than those in the control plant depending on the methods of the invention.

A control plant or plant cell may comprise, for example: (a) a wild-type plant or cell, i.e., of the same genotype as the starting material for the genetic alteration which resulted in the subject plant or cell; (b) a plant or plant cell of the same genotype as the starting material but which has been transformed with a null construct (i.e. with a construct which has no known effect on the trait of interest, such as a construct comprising a marker gene); (c) a plant or plant cell which is a non-transformed segregant among progeny of a subject plant or plant cell; (d) a plant or plant cell genetically identical to the subject plant or plant cell but which is not exposed to conditions or stimuli that would induce expression of the gene of interest; or (e) the subject plant or plant cell itself, under conditions in which the gene of interest is not expressed.

While the invention is described in terms of transformed plants, it is recognized that transformed organisms of the invention also include plant cells, plant protoplasts, plant cell tissue cultures from which plants can be regenerated, plant calli, plant clumps, and plant cells that are intact in plants or parts of plants such as embryos, pollen, ovules, seeds, leaves, flowers, branches, fruit, kernels, ears, cobs, husks, stalks, roots, root tips, anthers, and the like. Grain is intended to mean the mature seed produced by commercial growers for purposes other than growing or reproducing the species. Progeny, variants, and mutants of the regenerated plants are also included within the scope of the invention, provided that these parts comprise the introduced polynucleotides.

To downregulate expression of a PSAN protein-encoding gene of interest, antisense constructions, complementary to at least a portion of the messenger RNA (mRNA) for the sequences of a gene of interest, particularly a gene encoding a PSAN protein of interest can be constructed. Antisense nucleotides are designed to hybridize with the corresponding mRNA. Modifications of the antisense sequences may be made as long as the sequences hybridize to and interfere with expression of the corresponding mRNA. In this manner, antisense constructions having 70%, optimally 80%, more optimally 85%, 90%, 95% or greater sequence identity to the corresponding sequences to be silenced may be used. Furthermore, portions of the antisense nucleotides may be used to disrupt the expression of the target gene.

The polynucleotides of the invention can be used to isolate corresponding sequences from other plants. In this manner, methods such as PCR, hybridization, and the like can be used to identify such sequences based on their sequence homology or identity to the sequences set forth herein. Sequences isolated based on their sequence identity to the entire sequences set forth herein or to variants and fragments thereof are encompassed by the present invention. Such sequences include sequences that are orthologs of the disclosed sequences. "Orthologs" is intended to mean genes derived from a common ancestral gene and which are found in different species as a result of speciation. Genes found in different species are considered orthologs when their nucleotide sequences and/or their encoded protein sequences share at least 75%, 80%, 85%, 90%, 91%, 92%, 93%, 94%, 95%, 96%, 97%, 98%, 99%, or greater sequence identity. Functions of orthologs are often highly conserved among species. Thus, isolated polynucleotides that have transcription activation or enhancer activities and which share at least 75% sequence identity to the sequences disclosed herein, or to variants or fragments thereof, are encompassed by the present invention.

Variant sequences can be isolated by PCR. Methods for designing PCR primers and PCR cloning are generally known in the art and are disclosed in Sambrook et al. (1989) Molecular Cloning: A Laboratory Manual (2d ed., Cold Spring Harbor Laboratory Press, Plainview, N.Y.). See also Innis et al., eds. (1990) PCR Protocols: A Guide to Methods and Applications (Academic Press, New York); Innis and Gelfand, eds. (1995) PCR Strategies (Academic Press, New York); and Innis and Gelfand, eds. (1999) PCR Methods Manual (Academic Press, New York).

Variant sequences may also be identified by analysis of existing databases of sequenced genomes. In this manner, corresponding sequences encoding PSAN proteins can be identified and used in the methods of the invention. The variant sequences will retain the biological function of a PSAN protein. PSAN proteins associate with photosystem I on the lumenal side of the thylakoid membrane and have been shown to make contacts with multiple photosystem I protein subunits, likely including PsaG and PsaF (Amunts et al. (2007) *Nature* 447:58-63). These contacts allow for the proper assembly of a fully active photosystem I complex, and it has been proposed that PSAN is required for the efficient interaction of photosystem I with plastocyanin.

The expression cassette will include in the 5'-3' direction of transcription, a transcriptional and translational initiation region, a polynucleotide encoding a PSAN protein of the present invention, and a transcriptional and translational termination region (i.e., termination region) functional in plants.

A number of promoters may be used in the practice of the invention. The polynucleotides encoding a PSAN protein of the invention may be expressed from a promoter with a constitutive expression profile. Constitutive promoters include the CaMV 35S promoter (Odell et al. (1985) *Nature* 313:810-812); rice actin (McElroy et al. (1990) *Plant Cell* 2:163-171); ubiquitin (Christensen et al. (1989) *Plant Mol. Biol.* 12:619-632 and Christensen et al. (1992) *Plant Mol. Biol.* 18:675-689); pEMU (Last et al. (1991) *Theor. Appl. Genet.* 81:581-588); MAS (Velten et al. (1984) *EMBO J.* 3:2723-2730); ALS promoter (U.S. Pat. No. 5,659,026), and the like.

Polynucleotides of the invention encoding PSAN proteins of the invention may be expressed from tissue-preferred promoters. Tissue-preferred promoters include Yamamoto et al. (1997) *Plant J.* 12(2):255-265; Kawamata et al. (1997) *Plant Cell Physiol.* 38(7):792-803; Hansen et al. (1997) *Mol. Gen Genet.* 254(3):337-343; Russell et al. (1997) *Transgenic Res.* 6(2):157-168; Rinehart et al. (1996) *Plant Physiol.* 112(3):1331-1341; Van Camp et al. (1996) *Plant Physiol.* 112(2):525-535; Canevascini et al. (1996) *Plant Physiol.* 112(2):513-524; Yamamoto et al. (1994) *Plant Cell Physiol.* 35(5):773-778; Lam (1994) *Results Probl. Cell Differ.* 20:181-196; Orozco et al. (1993) *Plant Mol Biol.* 23(6):1129-1138; Matsuoka et al. (1993) *Proc Natl. Acad. Sci. USA* 90(20):9586-9590; and Guevara-Garcia et al. (1993) *Plant J.* 4(3):495-505. Leaf-preferred promoters are also known in the art. See, for example, Yamamoto et al. (1997) *Plant J.* 12(2):255-265; Kwon et al. (1994) *Plant Physiol.* 105:357-67; Yamamoto et al. (1994) *Plant Cell Physiol.* 35(5):773-778; Gotor et al. (1993) *Plant J.* 3:509-18; Orozco et al. (1993) *Plant Mol. Biol.* 23(6):1129-1138; and Matsuoka et al. (1993) *Proc. Natl. Acad. Sci. USA* 90(20): 9586-9590.

Developmentally-regulated promoters may be desirable for the expression of a polynucleotide encoding a PSAN protein. Such promoters may show a peak in expression at a particular developmental stage. Such promoters have been described in the art, e.g., U.S. 62/029,068; Gan and Amasino (1995) *Science* 270: 1986-1988; Rinehart et al. (1996) *Plant Physiol* 112: 1331-1341; Gray-Mitsumune et al. (1999) *Plant Mol Biol* 39: 657-669; Beaudoin and Rothstein (1997) *Plant Mol Biol* 33: 835-846; Genschik et al. (1994) *Gene* 148: 195-202, and the like.

Promoters that are induced following the application of a particular biotic and/or abiotic stress may be desirable for the expression of a polynucleotide encoding a PSAN protein. Such promoters have been described in the art, e.g., Yi et al. (2010) *Planta* 232: 743-754; Yamaguchi-Shinozaki and Shinozaki (1993) *Mol Gen Genet* 236: 331-340; U.S. Pat. No. 7,674,952; Rerksiri et al. (2013) *Sci World J* 2013: Article ID 397401; Khurana et al. (2013) *PLoS One* 8: e54418; Tao et al. (2015) *Plant Mol Biol Rep* 33: 200-208, and the like.

Cell-preferred promoters may be desirable for the expression of a polynucleotide encoding a PSAN protein. Such promoters may preferentially drive the expression of a downstream gene in a particular cell type such as a mesophyll or a bundle sheath cell. Such cell-preferred promoters have been described in the art, e.g., Viret et al. (1994) *Proc Natl Acad USA* 91: 8577-8581; U.S. Pat. Nos. 8,455,718; 7,642,347; Sattarzadeh et al. (2010) *Plant Biotechnol J* 8: 112-125; Engelmann et al. (2008) *Plant Physiol* 146: 1773-1785; Matsuoka et al. (1994) *Plant J* 6: 311-319, and the like.

It is recognized that a specific, non-constitutive expression profile may provide an improved plant phenotype relative to constitutive expression of a gene or genes of interest. For instance, many plant genes are regulated by light conditions, the application of particular stresses, the circadian cycle, or the stage of a plant's development. These expression profiles may be important for the function of the gene or gene product in planta. One strategy that may be used to provide a desired expression profile is the use of synthetic promoters containing cis-regulatory elements that drive the desired expression levels at the desired time and place in the plant. Cis-regulatory elements that can be used to alter gene expression in planta have been described in the scientific literature (Vandepoele et al. (2009) *Plant Physiol* 150: 535-546; Rushton et al. (2002) *Plant Cell* 14: 749-762). Cis-regulatory elements may also be used to alter promoter expression profiles, as described in Venter (2007) *Trends Plant Sci* 12: 118-124.

Plant terminators are known in the art and include those available from the Ti-plasmid of *A. tumefaciens*, such as the octopine synthase and nopaline synthase termination regions. See also Guerineau et al. (1991) *Mol. Gen. Genet.* 262:141-144; Proudfoot (1991) *Cell* 64:671-674; Sanfacon et al. (1991) *Genes Dev.* 5:141-149; Mogen et al. (1990) *Plant Cell* 2:1261-1272; Munroe et al. (1990) *Gene* 91:151-158; Ballas et al. (1989) *Nucleic Acids Res.* 17:7891-7903; and Joshi et al. (1987) *Nucleic Acids Res.* 15:9627-9639.

As indicated, the nucleotides encoding PSAN proteins of the present invention can be used in expression cassettes to transform plants of interest. Transformation protocols as well as protocols for introducing polypeptides or polynucleotide sequences into plants may vary depending on the type of plant or plant cell, i.e., monocot or dicot, targeted for transformation. The term "transform" or "transformation" refers to any method used to introduce polypeptides or polynucleotides into plant cells. Suitable methods of introducing polypeptides and polynucleotides into plant cells include microinjection (Crossway et al. (1986) *Biotechniques* 4:320-334), electroporation (Riggs et al. (1986) *Proc. Natl. Acad. Sci. USA* 83:5602-5606, *Agrobacterium*-mediated transformation (U.S. Pat. Nos. 5,563,055 and 5,981, 840), direct gene transfer (Paszkowski et al. (1984) *EMBO J.* 3:2717-2722), and ballistic particle acceleration (see, for example, U.S. Pat. Nos. 4,945,050; 5,879,918; 5,886,244; and, 5,932,782; Tomes et al. (1995) in Plant Cell, Tissue, and Organ Culture: Fundamental Methods, ed. Gamborg and Phillips (Springer-Verlag, Berlin); McCabe et al. (1988) *Biotechnology* 6:923-926); and Lec1 transformation (WO 00/28058). Also see Weissinger et al. (1988) *Ann. Rev. Genet.* 22:421-477; Sanford et al. (1987) *Particulate Science and Technology* 5:27-37 (onion); Christou et al. (1988) *Plant Physiol.* 87:671-674 (soybean); McCabe et al. (1988) *Bio/Technology* 6:923-926 (soybean); Finer and McMullen (1991) *In Vitro Cell Dev. Biol.* 27P:175-182 (soybean); Singh et al. (1998) *Theor. Appl. Genet.* 96:319-324 (soybean); Datta et al. (1990) *Biotechnology* 8:736-740 (rice); Klein et al. (1988) *Proc. Natl. Acad. Sci. USA* 85:4305-4309 (maize); Klein et al. (1988) *Biotechnology* 6:559-563 (maize); U.S. Pat. Nos. 5,240,855; 5,322,783; and, 5,324, 646; Klein et al. (1988) *Plant Physiol.* 91:440-444 (maize); Fromm et al. (1990) *Biotechnology* 8:833-839 (maize); Hooykaas-Van Slogteren et al. (1984) *Nature* (London) 311:763-764; U.S. Pat. No. 5,736,369 (cereals); Bytebier et al. (1987) *Proc. Natl. Acad. Sci. USA* 84:5345-5349 (*Liliaceae*); De Wet et al. (1985) in The Experimental Manipulation of Ovule Tissues, ed. Chapman et al. (Longman, N.Y.), pp. 197-209 (pollen); Kaeppler et al. (1990) *Plant Cell Reports* 9:415-418 and Kaeppler et al. (1992) *Theor. Appl. Genet.* 84:560-566 (whisker-mediated transformation); D'Halluin et al. (1992) *Plant Cell* 4:1495-1505 (electroporation); Li et al. (1993) *Plant Cell Reports* 12:250-255 and Christou and Ford (1995) *Annals of Botany* 75:407-413 (rice); Osjoda et al. (1996) *Nature Biotechnology* 14:745-750 (maize via *Agrobacterium tumefaciens*); all of which are herein incorporated by reference. "Stable transformation" is intended to mean that the nucleotide construct introduced into a plant integrates into the genome of the plant and is capable of being inherited by the progeny thereof.

The cells that have been transformed may be grown into plants in accordance with conventional ways. See, for example, McCormick et al. (1986) *Plant Cell Reports* 5:81-84. In this manner, the present invention provides transformed seed (also referred to as "transgenic seed") having a polynucleotide of the invention, for example, an expression cassette of the invention, stably incorporated into their genome.

The present invention may be used for transformation of any plant species, including, but not limited to, monocots and dicots. Examples of plant species of interest include, but are not limited to, corn (*Zea mays*), Brassica sp. (e.g., *B. napus, B. rapa, B. juncea*), particularly those Brassica species useful as sources of seed oil, alfalfa (*Medicago sativa*), rice (*Oryza sativa*), rye (*Secale cereale*), sorghum (*Sorghum bicolor, Sorghum vulgare*), millet (e.g., pearl millet (*Pennisetum glaucum*), proso millet (*Panicum miliaceum*), foxtail millet (*Setaria italica*), finger millet (*Eleusine coracana*)), sunflower (*Helianthus annuus*), safflower (*Carthamus tinctorius*), wheat (*Triticum aestivum*), soybean (*Glycine max*), tobacco (*Nicotiana tabacum*), potato (*Solanum tuberosum*), peanuts (*Arachis hypogaea*), cotton (*Gossypium barbadense, Gossypium hirsutum*), sweet potato (*Ipomoea batatus*), cassava (*Manihot esculenta*), coffee (*Coffea* spp.), coconut (*Cocos nucifera*), pineapple (*Ananas comosus*), citrus trees (*Citrus* spp.), cocoa (*Theobroma cacao*), tea (*Camellia sinensis*), banana (*Musa* spp.), avocado (*Persea americana*), fig (*Ficus* casica), guava (*Psidium guajava*), mango (*Mangifera indica*), olive (*Olea europaea*), papaya (*Carica papaya*), cashew (*Anacardium occidentale*), macadamia (*Macadamia integrifolia*), almond (*Prunus amygdalus*), sugar beets (*Beta vulgaris*), sugarcane (*Saccharum* spp.), oil palm (*Elaeis guineensis*), poplar (*Populus* spp.), eucalyptus (*Eucalyptus* spp.), oats (*Avena sativa*), barley (*Hordeum vulgare*), vegetables, ornamentals, and conifers.

In one embodiment, a construct containing a promoter that is operable in a plant cell, operably linked to a coding sequence encoding a PSAN protein of the present invention is used to transform a plant cell or cells. The transformed plant cell or cells are regenerated to produce transformed plants. These plants transformed with a construct comprising a functional promoter driving expression of a PSAN protein-encoding polynucleotide of the invention demonstrated increased plant yield, i.e., increased above-ground biomass and increased seed yield.

Now that it has been demonstrated that upregulation of PSAN increases plant yield, other methods for increasing expression of an endogenous PSAN sequence in a plant of interest can be used. The expression of a PSAN gene present in a plant's genome can be altered by inserting a transcriptional enhancer upstream of the PSAN gene present in the plant's genome. This strategy will allow the PSAN gene's expression to retain its normal developmental profile, while showing elevated transcript levels. This strategy will occur through the insertion of an enhancer element upstream of a PSAN gene of interest using a meganuclease designed against the genomic sequence of interest. Alternatively, a Cas9 endonuclease coupled with a guide RNA (gRNA) designed against the genomic sequence of interest, or a cpf1 endonuclease coupled with a gRNA designed against the genomic sequence of interest, is used to effect the insertion of an enhancer element upstream of a PSAN gene of interest. Alternatively, a deactivated Cas9 endonuclease fused to a transcriptional enhancer element is targeted to a genomic location near the transcription start site for a PSAN gene of interest, thereby modulating the expression of said PSAN gene of interest (Piatek et al. (2015) *Plant Biotechnol J* 13:578-589).

Alteration of the expression of a PSAN protein-encoding gene may be achieved through the use of precise genome-editing technologies to modulate the expression of the endogenous sequence. In this manner, a nucleic acid sequence will be inserted proximal to a native plant sequence encoding the PSAN through the use of methods available in the art. Such methods include, but are not limited to, meganucleases designed against the plant genomic sequence of interest (D'Halluin et al (2013) *Plant Biotechnol J* 11: 933-941); CRISPR-Cas9, CRISPR-Cpf1, TALENs, and other technologies for precise editing of genomes (Feng et al. (2013) *Cell Research* 23:1229-1232, Podevin et al. (2013) *Trends Biotechnology* 31: 375-383, Wei et al. (2013) *J Gen Genomics* 40: 281-289, Zhang et al (2013) WO 2013/026740, Zetsche et al. (2015) *Cell* 163: 759-771, U.S. Provisional Patent Application 62/295,325); *N. gregoryi* Argonaute-mediated DNA insertion (Gao et al. (2016) *Nat Biotechnol* doi:10.1038/nbt.3547); Cre-lox site-specific recombination (Dale et al. (1995) *Plant J* 7:649-659; Lyznik, et al. (2007) *Transgenic Plant J* 1:1-9; FLP-FRT recombination (Li et al. (2009) *Plant Physiol* 151:1087-1095); Bxb1-mediated integration (Yau et al. (2011) *Plant J* 701:147-166); zinc-finger mediated integration (Wright et al. (2005) *Plant J* 44:693-705); Cai et al. (2009) *Plant Mol Biol* 69:699-709); and homologous recombination (Lieberman-Lazarovich and Levy (2011) *Methods Mol Biol* 701: 51-65; Puchta (2002) *Plant Mol Biol* 48:173-182). The insertion of said nucleic acid sequences will be used to achieve the desired result of overexpression and/or altered expression profile of a PSAN gene.

Enhancers include any molecule capable of enhancing gene expression when inserted into the genome of a plant. Thus, an enhancer can be inserted in a region of the genome upstream or downstream of a PSAN sequence of interest to enhance expression. Enhancers may be cis-acting, and can be located anywhere within the genome relative to a gene for which expression will be enhanced. For example, an enhancer may be positioned within about 1 Mbp, within about 100 kbp, within about 50 kbp, about 30 kbp, about 20 kbp, about 10 kbp, about 5 kbp, about 3 kbp, or about 1 kbp of a coding sequence for which it enhances expression. An enhancer may also be located within about 1500 bp of a gene for which it enhances expression, or may be directly proximal to or located within an intron of a gene for which it enhances expression. Enhancers for use in modulating the expression of an endogenous gene encoding a PSAN protein or homolog according to the present invention include classical enhancer elements such as the CaMV 35S enhancer element, cytomegalovirus (CMV) early promoter enhancer element, and the SV40 enhancer element, and also intron-mediated enhancer elements that enhance gene expression such as the maize shrunken-1 enhancer element (Clancy and Hannah (2002) *Plant Physiol.* 130(2):918-29). Further examples of enhancers which may be introduced into a plant genome to modulate expression include a PetE enhancer (Chua et al. (2003) *Plant Cell* 15:11468-1479), or a rice α-amylase enhancer (Chen et al. (2002) *J. Biol. Chem.* 277:13641-13649), or any enhancer known in the art (Chudalayandi (2011) *Methods Mol. Biol.* 701:285-300). In some embodiments, the present invention comprises a subdomain, fragment, or duplicated enhancer element (Benfrey et al. (1990) *EMBO J* 9:1677-1684).

Alteration of PSAN gene expression may also be achieved through the modification of DNA in a way that does not alter the sequence of the DNA. Such changes could include modifying the chromatin content or structure of the PSAN gene of interest and/or of the DNA surrounding the PSAN gene. It is well known that such changes in chromatin content or structure can affect gene transcription (Hirschhorn et al. (1992) *Genes and Dev* 6:2288-2298; Narlikar et al. (2002) *Cell* 108: 475-487). Such changes could also include altering the methylation status of the PSAN gene of interest and/or of the DNA surrounding the PSAN gene of interest. It is well known that such changes in DNA methylation can alter transcription (Hsieh (1994) *Mol Cell Biol* 14: 5487-5494). Targeted epigenome editing has been shown to affect the transcription of a gene in a predictable manner (Hilton et al. (2015) 33: 510-517). It will be obvious to those skilled in the art that other similar alterations (collectively termed "epigenetic alterations") to the DNA that regulates transcription of the PSAN gene of interest may be applied in order to achieve the desired result of an altered PSAN gene expression profile.

Alteration of PSAN gene expression may also be achieved through the use of transposable element technologies to alter gene expression. It is well understood that transposable elements can alter the expression of nearby DNA (McGinnis et al. (1983) *Cell* 34:75-84). Alteration of the expression of a gene encoding PSAN may be achieved by inserting a transposable element upstream of the PSAN gene of interest, causing the expression of said gene to be altered.

Alteration of PSAN gene expression may also be achieved through expression of a transcription factor or transcription factors that regulate the expression of the PSAN gene of interest. It is well understood that alteration of transcription factor expression can in turn alter the expression of the target gene(s) of said transcription factor (Hiratsu et al. (2003) *Plant J* 34:733-739). Alteration of PSAN gene expression may be achieved by altering the expression of transcription factor(s) that interact with the PSAN gene of interest and regulate its expression.

Alteration of PSAN gene expression may also be achieved through the insertion of a promoter upstream of the open reading frame encoding a native PSAN in the plant species of interest. This will occur through the insertion of a promoter of interest upstream of a PSAN protein-encoding open reading frame using a meganuclease designed against the genomic sequence of interest. This strategy is well-understood and has been demonstrated previously to insert a transgene at a predefined location in the cotton genome (D'Halluin et al. (2013) *Plant Biotechnol J* 11: 933-941). It will be obvious to those skilled in the art that other technologies can be used to achieve a similar result of insertion of genetic elements at a predefined genomic locus by causing a double-strand break at said predefined genomic locus and providing an appropriate DNA template for insertion (e.g., CRISPR-Cas9, CRISPR-cpf1, TALENs, and other technologies for precise editing of genomes).

The following examples are offered by way of illustration and not by way of limitation. All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

EXPERIMENTAL

Example 1—Construction of PSAN Plant Transformation Vectors

An open reading frame encoding a maize PSAN protein was synthesized. This open reading frame comprised SEQ ID NO:1, encoding the protein sequence of SEQ ID NO:2. Appropriate restriction sites were included at the 5' and 3' ends of the coding sequence to allow this DNA to be cloned into plant transformation vectors that contained genetic elements suitable for controlling gene expression. In each plant transformation construct, the PSAN open reading frame was located downstream of a plant promoter and 5' untranslated region (5'UTR) and upstream of a 3'UTR. Table 2 summarizes the plant transformation constructs that were built containing a PSAN open reading frame.

TABLE 2

PSAN plant transformation constructs

| Construct ID | Promoter + 5'UTR | ORF | 3'UTR |
|---|---|---|---|
| 130620 | 2X 35S (SEQ ID NO: 3) | PSAN (SEQ ID NO: 1, encoding SEQ ID NO: 2) | 35S poly A (SEQ ID NO: 4) |
| 131105 | 4xRGCGR (SEQ ID NO: 5) | PSAN (SEQ ID NO: 1, encoding SEQ ID NO: 2) | ZmCA (SEQ ID NO: 6) |
| 131808 | 4xRGCGR (SEQ ID NO: 5) | PSAN (SEQ ID NO: 1, encoding SEQ ID NO: 2) | ZmCA (SEQ ID NO: 6) |
| 131897 | ZmCA1 5'mod (SEQ ID NO: 93) | PSAN (SEQ ID NO: 1, encoding SEQ ID NO: 2) | ZmCA (SEQ ID NO: 6) |

In addition to the single-genic PSAN plant transformation constructs listed in Table 2, a multigenic plant transformation construct containing a PSAN gene cassette and a second linked cassette was also built. Table 3 summarizes the multigenic PSAN plant transformation construct.

TABLE 3

PSAN multigenic plant transformation constructs

| Construct ID | Promoter1 | ORF #1 | 3'UTR | Promoter2 | ORF #2 | 3'UTR 2 |
|---|---|---|---|---|---|---|
| 131807 | 4xRGCGR (SEQ ID NO: 5) | PSAN (SEQ ID NO: 1, encoding SEQ ID NO: 2) | ZmCA (SEQ ID NO: 6) | ZmRbcS (SEQ ID NO: 89) | RbcS-ictB (SEQ ID NO: 91, encoding SEQ ID NO: 92) | ZmRbcS (SEQ ID NO: 90) |
| 131833 | 4xRGCGR (SEQ ID NO: 5) | PSAN (SEQ ID NO: 1, encoding SEQ ID NO: 2) | ZmCA (SEQ ID NO: 6) | OsCA (SEQ ID NO: 94) | Maize transcription factor (SEQ ID NO: 95, encoding SEQ ID NO: 96) | OsCA (SEQ ID NO: 97) |
| 132191 | 4xRGCGR (SEQ ID NO: 5) | PSAN (SEQ ID NO: 1, encoding SEQ ID NO: 2) | ZmCA (SEQ ID NO: 6) | ZmRbcS (SEQ ID NO: 98) | ictB (SEQ ID NO: 99, encoding SEQ ID NO: 100) | ZmRbcS (SEQ ID NO: 90) |

In addition to the gene cassettes described in Tables 2 and 3, each plant transformation construct listed in Tables 2 and 3 also contained a selectable marker cassette suitable for the selection of transformed plant cells and regeneration of plants following the introduction of the plant transformation vector, as described below. Each transformation vector was built in a plasmid that contained sequences suitable for plasmid maintenance in *E. coli* and in *Agrobacterium tumefaciens*. Following verification that the plant transformation constructs listed in Tables 2 and 3 contained the desired sequences, they were transformed into *A. tumefaciens* cells for plant transformation.

Example 2—Transformation of *Setaria viridis*

*A. tumefaciens* cells harboring PSAN plant transformation vectors were used to transform *S. viridis* cells according to a previously described method (PCT/US2015/43989, herein incorporated by reference). Following transformation of the *S. viridis* cells with the relevant plant transformation vectors and regeneration of *S. viridis* plants, PCR analyses were performed to confirm the presence of the gene(s) of interest in the *S. viridis* genome. Table 4 summarizes the transformation constructs used to transform *S. viridis*, along with the number of PCR-verified transgenic plants that resulted from transformation with each construct.

TABLE 4

Summary of *S. viridis* transformation with PSAN plant transformation vectors

| Construct | # Events |
|---|---|
| 130620 | 41 |
| 131105 | 29 |
| 131833 | 39 |

Example 3—Transformation of Maize (*Zea mays*)

*A. tumefaciens* cells harboring PSAN plant transformation vectors are used to transform maize (*Zea mays* cv. B104) cells suitable for regeneration on tissue culture medium. Following transformation of the maize cells with the relevant plant transformation vectors and regeneration of maize plants, PCR analyses are performed to confirm the presence of the gene(s) of interest in the maize genome.

Construct 131808 was used to transform maize (*Zea mays* cv. B104) cells. This transformation resulted in the production of three rooted plantlets that were transferred to soil and confirmed to contain the PSAN gene cassette as described in Table 2.

Example 4—Transformation of Rice (*Oryza sativa*)

*A. tumefaciens* cells harboring PSAN plant transformation vectors are used to transform rice (*Oryza sativa* cv. Kitaake) cells suitable for regeneration on tissue culture medium. Following transformation of the rice cells with the relevant plant transformation vectors and regeneration of rice plants, PCR analyses are performed to confirm the presence of the gene(s) of interest in the rice genome.

Example 5—Characterization of Transgenic *S. viridis*

Following the transformation and regeneration of *S. viridis* plants transformed with a PSAN plant transformation vector, the T0-generation plants were cultivated to maturity to produce T1-generation seeds by self-pollination of the T0-generation plants. T1-generation *S. viridis* plants harboring the PSAN gene cassette of interest were grown in a greenhouse setting to assess the effects of PSAN gene expression on plant growth and terminal above-ground biomass and seed yield. A randomized block design was used with a wild-type *S. viridis* border row to eliminate edge effects from the analysis. Null segregant plants were grown alongside the transgenic *S. viridis* plants in identical environmental conditions. Table 5 summarizes the results of the biomass and seed yield determinations made from experiments with T1-generation *S. viridis* plants harboring a PSAN gene cassette as a result of transformation. It should be noted that growth conditions (e.g., temperature and light conditions) likely changed between the experiment used to test the 130620 events and the experiment used to test the 131105 events, and thus there were differences in growth between these two experiments; comparisons were made between transgenic and null segregants grown under identical environmental conditions. This table indicates the construct used for transformation, as described in Tables 2 and 3, followed by the T0 event number from which the T1 seed was harvested.

TABLE 5

Summary of *S. viridis* greenhouse observations with T1-generation plants

| | DW (g) | Seed Yield (g) | DW Change (%) | Seed Change (%) |
|---|---|---|---|---|
| 131105-18 | 3.39 ± 0.25 | 0.33 ± 0.01 | 9.7% | 6.5% |
| 131105-19 | 3.17 ± 0.33 | 0.34 ± 0.04 | 2.6% | 9.7% |
| 131105-2 | 3.43 ± 0.29 | 0.34 ± 0.02 | 11.0% | 9.7% |
| 131105-21 | 4.15 ± 0.15 | 0.39 ± 0.02 | 34.3% | 25.8% |
| 131105-null | 3.09 ± 0.3 | 0.31 ± 0.02 | n/a | n/a |
| 130620-12A | 1.78 ± 0.21 | 0.21 ± 0.03 | −22.9% | −19.2% |
| 130620-14 | 2.12 ± 0.25 | 0.17 ± 0.03 | −8.2% | −34.6% |
| 130620-7 | 1.88 ± 0.33 | 0.24 ± 0.06 | −18.6% | −7.7% |
| 130620-8A | 2.02 ± 0.25 | 0.25 ± 0.05 | −12.6% | −3.8% |
| 130620-9 | 1.99 ± 0.25 | 0.14 ± 0.03 | −13.9% | −46.2% |
| Null | 2.31 ± 0.33 | 0.26 ± 0.05 | n/a | n/a |

In Table 5, the dry weight of the above-ground biomass is indicated in the DW column in grams. Similarly, the dry weight of the harvested seeds is indicated in grams in the Seed Yield column. The DW Change and Seed Change columns indicate the percent change in above-ground biomass and seed yield, respectively, relative to the null segregants from the appropriate construct. As this table shows, all four of the 131105 events tested displayed increased biomass accumulation and increased seed yield relative to null segregant controls, with biomass increases of up to 34.3% and seed yield increases of up to 25.8%. All five of the 130620 events tested showed a decrease in both biomass accumulation and seed yield relative to null segregant controls.

Example 6—Characterization of Transgenic Maize

T0-generation maize plants transformed with the PSAN plant transformation vector of interest and confirmed to contain the gene(s) of interest are grown to maturity in a greenhouse. When the T0 plants reach reproductive stages, they are pollinated by an appropriate inbred maize line to produce hybrid maize seeds. Alternatively, or in addition to pollination of the T0 transgenic maize plant, the pollen from the T0 is used to pollinate one or more inbred maize lines to produce hybrid maize seeds. The F1-generation hybrid seed resulting from these pollinations are planted in a field setting in two- or four-row plots and cultivated using standard agronomic practices. Plants are genotyped to determine which plants do and which do not contain the PSAN gene cassette and any other relevant gene cassettes (e.g., a selectable marker gene cassette) that were included in the PSAN plant transformation vector. Following the maturation of the maize plants, the seed is harvested. Seeds from the plants containing the PSAN gene cassette are pooled, as are seeds from the null segregant plants lacking the PSAN gene cassette. The seeds are weighed, and seed yields are calculated for the plants containing the PSAN gene cassette as well as for the null segregant plants lacking the PSAN gene cassette. Appropriate statistical analyses are performed to determine whether plants containing a PSAN gene cassette produced higher yields than those plants that lacked a PSAN gene cassette.

Alternatively, T0-generation maize plants transformed with the PSAN plant transformation vector of interest and confirmed to contain the gene(s) of interest are grown to maturity in a greenhouse, then self-pollinated. The resulting T1 seeds are planted in a greenhouse and the T1 plants are cultivated. T1 plants are genotyped to identify homozygous, heterozygous, and null segregant plants. Pollen from homozygous T1 plants is used to pollinate one or more inbred maize lines to produce hybrid maize seeds. Pollen from null segregant plants is also used to pollinate one or more inbred maize lines to produce hybrid maize seeds. The resulting hybrid seeds are planted in a field setting in two- or four-row plots and cultivated using standard agronomic practices. Following the maturation of the maize plants, the seed is harvested. Seeds from the plants containing the PSAN gene cassette are pooled, as are seeds from the null segregant plants lacking the PSAN gene cassette. The seeds are weighed, and seed yields are calculated for the plants containing the PSAN gene cassette as well as for the null segregant plants lacking the PSAN gene cassette. Appropriate statistical analyses are performed to determine whether plants containing a PSAN gene cassette produced higher yields than those plants that lacked a PSAN gene cassette.

Example 7—Characterization of Transgenic Rice

T0-generation rice plants transformed with the PSAN plant transformation vector of interest and confirmed to contain the gene(s) of interest are grown to maturity in a greenhouse, then self-pollinated. The resulting T1 seeds are planted in a greenhouse and the T1 plants are cultivated. T1 plants are genotyped to identify homozygous, heterozygous, and null segregant plants. The plants from each group are grown to maturity and allowed to self-pollinate to produce T2 seed. The T2 seed resulting from this self-pollination is harvested and weighed, and seed yields from homozygous, heterozygous, and null segregant plants are calculated. Appropriate statistical analyses are performed to determine whether plants containing a PSAN gene cassette produced higher yields than those plants that lacked a PSAN gene cassette.

T1-generation plants grown from seed that resulted from self-pollination of T0-generation plants, or T2-generation plants grown from seed that resulted from self-pollination of homozygous T1-generation plants, are grown in a field setting. In the case of T2-generation plants, null-segregant T1-generation plants are also self-pollinated to produce T2-generation null plants as negative controls. The plants are cultivated using standard agronomic practices and allowed to reach maturity. Upon reaching maturity, the plants are allowed to self-pollinate. The seed resulting from these self-pollinations is harvested and weighed, and seed yields from homozygous, heterozygous, and null segregant plants are calculated. Appropriate statistical analyses are performed to determine whether plants containing a PSAN gene cassette produced higher yields than those plants that lacked a PSAN gene cassette.

We claim:

1. A method for increasing crop yield comprising transforming a plant with at least one PSAN protein-encoding sequence, wherein said PSAN protein-encoding sequence shares at least 95% identity with SEQ ID NO:1 and encodes a protein having PSAN function, or encodes a variant protein that shares at least 95% identity with SEQ ID NO:2, wherein said variant protein retains PSAN function, and wherein said PSAN protein-encoding sequence is expressed from a promoter comprising the nucleic acid sequence set forth in SEQ ID NO: 5.

2. A plant having stably incorporated into its genome a promoter that drives expression in a plant operably linked to a PSAN protein-encoding sequence, wherein said promoter is heterologous to said PSAN protein-encoding sequence, wherein said PSAN protein-encoding sequence shares at least 95% identity with SEQ ID NO:1 and encodes a protein having PSAN function, or encodes a variant protein that shares at least 95% identity with SEQ ID NO:2, wherein said variant protein retains PSAN function, and wherein said promoter comprises the nucleic acid sequence set forth in SEQ ID NO: 5.

3. Seed of the plant of claim 2, wherein said seed comprises said PSAN protein-encoding sequence.

4. The plant of claim 2 wherein said plant is a monocot.

5. The plant of claim 2 wherein said plant is a dicot.

6. A DNA construct comprising, in operable linkage,
   a. A promoter that is functional in a plant cell, wherein said promoter comprises the nucleic acid sequence set forth in SEQ ID NO:5 and,
   b. A nucleic acid sequence encoding a PSAN protein, wherein said nucleic acid sequence encoding a PSAN protein shares at least 95% identity with SEQ ID NO:1 and encodes a protein with PSAN function, or encodes a variant protein that shares at least 95% identity with SEQ ID NO:2, wherein said variant protein retains PSAN function, and wherein said promoter that is functional in a plant cell is a mesophyll-preferred promoter that is heterologous to said nucleic acid sequence encoding a PSAN protein.

* * * * *